United States Patent
Dunki-Jacobs et al.

(10) Patent No.: US 11,871,927 B2
(45) Date of Patent: Jan. 16, 2024

(54) END EFFECTORS, SURGICAL STAPLING DEVICES, AND METHODS OF USING SAME

(71) Applicant: Standard Bariatrics, Inc., Cincinnati, OH (US)

(72) Inventors: Adam R. Dunki-Jacobs, Cincinnati, OH (US); Jonathan R. Thompson, Cincinnati, OH (US); Richard P. Nuchols, Williamsburg, OH (US)

(*) Notice: Subject to any disclaimer, the term of this patent is extended or adjusted under 35 U.S.C. 154(b) by 0 days.

(21) Appl. No.: 16/872,609

(22) Filed: May 12, 2020

(65) Prior Publication Data
US 2020/0268385 A1 Aug. 27, 2020

Related U.S. Application Data

(63) Continuation of application No. 16/103,644, filed on Aug. 14, 2018.
(Continued)

(51) Int. Cl.
*A61B 17/072* (2006.01)
*A61B 17/32* (2006.01)
(Continued)

(52) U.S. Cl.
CPC .... *A61B 17/07207* (2013.01); *A61B 17/0644* (2013.01); *A61B 17/0686* (2013.01);
(Continued)

(58) Field of Classification Search
CPC .. A61B 2017/07214; A61B 2017/0725; A61B 2017/07257; A61B 17/07292
See application file for complete search history.

(56) References Cited

U.S. PATENT DOCUMENTS

| 848,126 A | 3/1907 | Roosevelt |
| 1,413,896 A | 4/1922 | Brix |

(Continued)

FOREIGN PATENT DOCUMENTS

| CA | 2663002 A1 | 10/2009 |
| EP | 140552 A2 | 5/1985 |

(Continued)

OTHER PUBLICATIONS

International Search Report and Written Opinion of the International Searching Authority received in International Patent Appln. No. PCT/US2022/021250; dated Jun. 10, 2022; 12 pages.
(Continued)

*Primary Examiner* — Gloria R Weeks

(57) ABSTRACT

Embodiments include an end effector including an anvil, the anvil having an anvil face, an anvil blade channel defined by the anvil face, a first pocket row of first row staple pockets, a second pocket row of second row staple pockets, a third pocket row of third row staple pockets, a fourth pocket row of fourth row staple pockets, a fifth pocket row of fifth row staple pockets, a sixth pocket row of sixth row staple pockets, a cartridge having a a cartridge face defining a cartridge blade channel, the cartridge being configured to retain a plurality of staples, and a blade, the blade having a cutting edge, where the blade is movable from a first position at a distal end of the cartridge to a second position at a proximal end of the cartridge.

56 Claims, 48 Drawing Sheets

Related U.S. Application Data

(60) Provisional application No. 62/676,493, filed on May 25, 2018, provisional application No. 62/672,996, filed on May 17, 2018, provisional application No. 62/662,517, filed on Apr. 25, 2018, provisional application No. 62/579,703, filed on Oct. 31, 2017, provisional application No. 62/545,324, filed on Aug. 14, 2017.

(51) Int. Cl.
| | |
|---|---|
| *A61B 17/28* | (2006.01) |
| *A61B 17/064* | (2006.01) |
| *A61B 17/26* | (2006.01) |
| *A61B 17/115* | (2006.01) |
| *A61B 17/068* | (2006.01) |
| *A61B 17/00* | (2006.01) |
| *A61B 1/313* | (2006.01) |
| *A61F 5/00* | (2006.01) |
| *A61B 17/29* | (2006.01) |

(52) U.S. Cl.
CPC ...... *A61B 17/072* (2013.01); *A61B 17/07292* (2013.01); *A61B 17/1155* (2013.01); *A61B 17/26* (2013.01); *A61B 17/28* (2013.01); *A61B 17/32* (2013.01); *A61B 1/3132* (2013.01); *A61B 2017/00017* (2013.01); *A61B 2017/0046* (2013.01); *A61B 2017/00115* (2013.01); *A61B 2017/00199* (2013.01); *A61B 2017/00393* (2013.01); *A61B 2017/00398* (2013.01); *A61B 2017/00407* (2013.01); *A61B 2017/00477* (2013.01); *A61B 2017/00818* (2013.01); *A61B 2017/07214* (2013.01); *A61B 2017/07235* (2013.01); *A61B 2017/07242* (2013.01); *A61B 2017/07257* (2013.01); *A61B 2017/07264* (2013.01); *A61B 2017/07271* (2013.01); *A61B 2017/07285* (2013.01); *A61B 2017/2916* (2013.01); *A61F 5/0083* (2013.01)

(56) References Cited

U.S. PATENT DOCUMENTS

| | | | |
|---|---|---|---|
| 2,659,371 A | 11/1953 | Schnee | |
| 2,686,520 A | 8/1954 | Jarvis et al. | |
| 3,017,637 A | 1/1962 | Sampson | |
| 3,490,675 A | 1/1970 | Green et al. | |
| 3,551,987 A | 1/1971 | Wilkinson | |
| 3,877,434 A | 4/1975 | Ferguson | |
| 4,216,891 A * | 8/1980 | Behlke | A61B 17/072 227/19 |
| 4,269,190 A | 5/1981 | Behney | |
| 4,319,576 A | 3/1982 | Rothfuss | |
| 4,354,628 A | 10/1982 | Green | |
| 4,442,964 A | 4/1984 | Becht | |
| 4,458,681 A | 7/1984 | Hopkins | |
| 4,494,057 A | 1/1985 | Hotta | |
| 4,520,817 A | 6/1985 | Green | |
| 4,527,724 A | 7/1985 | Chow et al. | |
| 4,558,699 A | 12/1985 | Bashour | |
| 4,605,001 A | 8/1986 | Rothfuss et al. | |
| 4,605,004 A | 8/1986 | Di Giovanni et al. | |
| 4,608,981 A | 9/1986 | Rothfuss et al. | |
| 4,610,383 A | 9/1986 | Rothfuss et al. | |
| 4,617,928 A | 10/1986 | Alfranca | |
| 4,632,290 A | 12/1986 | Green et al. | |
| 4,633,861 A | 1/1987 | Chow et al. | |
| 4,676,774 A | 6/1987 | Semm et al. | |
| 4,679,557 A | 7/1987 | Opie et al. | |
| 4,705,038 A | 11/1987 | Sjostrom et al. | |
| 4,784,137 A | 11/1988 | Kulik et al. | |
| 4,803,985 A | 2/1989 | Hill | |
| 4,819,853 A | 4/1989 | Green | |
| 4,848,637 A | 7/1989 | Pruitt | |
| 4,930,503 A | 6/1990 | Pruitt | |
| 4,935,006 A | 6/1990 | Hasson | |
| 4,941,623 A | 7/1990 | Pruitt | |
| 4,951,861 A | 8/1990 | Schulze et al. | |
| 4,976,721 A | 12/1990 | Blasnik et al. | |
| 4,978,049 A | 12/1990 | Green | |
| 5,040,715 A | 8/1991 | Green et al. | |
| 5,136,220 A | 8/1992 | Philipp | |
| 5,152,744 A | 10/1992 | Krause et al. | |
| 5,176,651 A | 1/1993 | Allgood et al. | |
| 5,205,459 A | 4/1993 | Brinkerhoff et al. | |
| 5,219,111 A | 6/1993 | Bilotti et al. | |
| 5,221,036 A | 6/1993 | Takase | |
| 5,222,961 A | 6/1993 | Nakao et al. | |
| 5,258,009 A | 11/1993 | Conners | |
| 5,307,976 A | 5/1994 | Olson et al. | |
| 5,308,576 A | 5/1994 | Green et al. | |
| 5,312,410 A | 5/1994 | Miller et al. | |
| 5,327,914 A | 7/1994 | Shlain | |
| 5,333,772 A | 8/1994 | Rothfuss et al. | |
| 5,345,949 A | 9/1994 | Shlain | |
| 5,389,098 A | 2/1995 | Tsuruta et al. | |
| 5,395,030 A | 3/1995 | Kuramoto et al. | |
| 5,395,034 A | 3/1995 | Allen et al. | |
| 5,413,267 A * | 5/1995 | Solyntjes | A61B 17/072 227/175.4 |
| 5,415,334 A | 5/1995 | Williamson et al. | |
| 5,431,323 A | 7/1995 | Smith et al. | |
| 5,443,475 A | 8/1995 | Auerbach et al. | |
| 5,452,836 A | 9/1995 | Huitema et al. | |
| 5,452,837 A | 9/1995 | Williamson et al. | |
| 5,456,401 A | 10/1995 | Green et al. | |
| 5,465,895 A | 11/1995 | Knodel et al. | |
| 5,465,896 A | 11/1995 | Allen et al. | |
| 5,469,840 A | 11/1995 | Tanii et al. | |
| 5,470,006 A * | 11/1995 | Rodak | A61B 17/072 227/176.1 |
| 5,470,009 A | 11/1995 | Rodak | |
| 5,480,089 A | 1/1996 | Blewett | |
| 5,485,952 A | 1/1996 | Fontayne | |
| 5,487,500 A | 1/1996 | Knodel et al. | |
| 5,496,333 A | 3/1996 | Sackier et al. | |
| 5,503,638 A | 4/1996 | Cooper et al. | |
| 5,507,426 A | 4/1996 | Young et al. | |
| 5,507,773 A | 4/1996 | Huitema et al. | |
| 5,514,098 A | 5/1996 | Pfoslgraf et al. | |
| 5,531,744 A | 7/1996 | Nardella et al. | |
| 5,549,621 A | 8/1996 | Bessler et al. | |
| 5,551,622 A | 9/1996 | Yoon | |
| 5,554,169 A | 9/1996 | Green et al. | |
| 5,560,530 A | 10/1996 | Bolanos et al. | |
| 5,562,702 A | 10/1996 | Huitema et al. | |
| 5,571,116 A | 11/1996 | Bolanos et al. | |
| 5,571,131 A | 11/1996 | Ek et al. | |
| 5,586,711 A | 12/1996 | Plyley et al. | |
| 5,597,107 A | 1/1997 | Knodel et al. | |
| 5,630,540 A | 5/1997 | Blewett | |
| 5,632,432 A | 5/1997 | Schulze et al. | |
| 5,636,780 A | 6/1997 | Green et al. | |
| 5,655,698 A | 8/1997 | Yoon | |
| 5,662,667 A | 9/1997 | Knodel | |
| 5,676,674 A | 10/1997 | Bolanos et al. | |
| 5,689,159 A | 11/1997 | Culp et al. | |
| 5,697,542 A | 12/1997 | Knodel et al. | |
| 5,702,409 A | 12/1997 | Rayburn et al. | |
| 5,704,534 A | 1/1998 | Huitema et al. | |
| 5,707,369 A | 1/1998 | Vaitekunas et al. | |
| 5,732,871 A | 3/1998 | Clark et al. | |
| 5,762,256 A | 6/1998 | Mastri et al. | |
| 5,779,130 A | 7/1998 | Alesi et al. | |
| 5,779,132 A | 7/1998 | Knodel et al. | |
| 5,782,396 A | 7/1998 | Mastri et al. | |
| 5,797,538 A | 8/1998 | Heaton et al. | |
| 5,810,240 A | 9/1998 | Robertson | |
| 5,814,055 A | 9/1998 | Knodel et al. | |
| 5,819,240 A | 10/1998 | Kara | |
| 5,820,009 A | 10/1998 | Melling et al. | |

(56) References Cited

U.S. PATENT DOCUMENTS

| | | | |
|---|---|---|---|
| 5,865,361 A | 2/1999 | Milliman et al. | |
| 5,868,760 A | 2/1999 | McGuckin, Jr. | |
| 5,871,135 A * | 2/1999 | Williamson, IV | A61B 17/07207 227/178.1 |
| 5,901,895 A | 5/1999 | Heaton et al. | |
| 5,902,312 A | 5/1999 | Frater et al. | |
| 5,954,259 A | 9/1999 | Viola et al. | |
| 5,964,394 A | 10/1999 | Robertson | |
| 5,980,248 A | 11/1999 | Kusakabe et al. | |
| 5,988,479 A | 11/1999 | Palmer | |
| 6,032,849 A | 3/2000 | Mastri et al. | |
| 6,099,551 A | 8/2000 | Gabbay | |
| 6,264,087 B1 | 7/2001 | Whitman | |
| 6,270,507 B1 | 8/2001 | Callicrate | |
| 6,315,184 B1 | 11/2001 | Whitman | |
| 6,325,810 B1 | 12/2001 | Hamilton et al. | |
| 6,345,754 B1 | 2/2002 | Jeng | |
| 6,488,196 B1 | 12/2002 | Fenton | |
| 6,505,768 B2 | 1/2003 | Whitman | |
| 6,511,490 B2 | 1/2003 | Robert | |
| 6,616,446 B1 | 9/2003 | Schmid | |
| 6,716,233 B1 | 4/2004 | Whitman | |
| 6,769,590 B2 | 8/2004 | Vresh et al. | |
| 6,793,652 B1 | 9/2004 | Whitman et al. | |
| 6,835,199 B2 | 12/2004 | McGuckin et al. | |
| RE38,708 E * | 3/2005 | Bolanos | A61B 17/07207 227/180.1 |
| 6,953,138 B1 | 10/2005 | Dworak et al. | |
| 6,978,921 B2 | 12/2005 | Shelton, IV et al. | |
| 6,986,451 B1 | 1/2006 | Mastri et al. | |
| 6,988,649 B2 | 1/2006 | Shelton, IV et al. | |
| 7,025,791 B2 | 4/2006 | Levine et al. | |
| 7,032,799 B2 | 4/2006 | Viola et al. | |
| 7,037,344 B2 | 5/2006 | Kagan et al. | |
| 7,044,353 B2 | 5/2006 | Mastri et al. | |
| 7,070,083 B2 | 7/2006 | Jankowski | |
| 7,128,253 B2 | 10/2006 | Mastri et al. | |
| 7,134,587 B2 | 11/2006 | Schwemberger et al. | |
| 7,175,648 B2 | 2/2007 | Nakao | |
| 7,207,472 B2 | 4/2007 | Wukusick et al. | |
| 7,225,964 B2 | 6/2007 | Mastri et al. | |
| 7,229,428 B2 | 6/2007 | Gannoe et al. | |
| 7,235,089 B1 | 6/2007 | McGuckin, Jr. | |
| 7,258,262 B2 | 8/2007 | Mastri et al. | |
| 7,278,562 B2 | 10/2007 | Mastri et al. | |
| 7,278,563 B1 | 10/2007 | Green | |
| 7,288,100 B2 | 10/2007 | Molina Trigueros | |
| 7,308,998 B2 | 12/2007 | Mastri et al. | |
| RE40,237 E * | 4/2008 | Bilotti | A61B 17/115 227/180.1 |
| 7,398,908 B2 | 7/2008 | Holsten et al. | |
| 7,401,721 B2 | 7/2008 | Holsten et al. | |
| 7,404,508 B2 | 7/2008 | Smith et al. | |
| 7,407,075 B2 | 8/2008 | Holsten et al. | |
| 7,407,076 B2 | 8/2008 | Racenet et al. | |
| 7,422,138 B2 | 9/2008 | Bilotti et al. | |
| 7,434,716 B2 | 10/2008 | Viola | |
| 7,434,717 B2 | 10/2008 | Shelton, IV et al. | |
| 7,438,209 B1 | 10/2008 | Hess et al. | |
| 7,455,676 B2 | 11/2008 | Holsten et al. | |
| 7,467,740 B2 | 12/2008 | Shelton, IV et al. | |
| 7,472,815 B2 | 1/2009 | Shelton, IV et al. | |
| 7,481,349 B2 | 1/2009 | Holsten et al. | |
| 7,500,979 B2 | 3/2009 | Hueil et al. | |
| 7,506,791 B2 | 3/2009 | Omaits et al. | |
| 7,510,107 B2 | 3/2009 | Timm et al. | |
| 7,549,564 B2 | 6/2009 | Boudreaux | |
| 7,549,654 B2 | 6/2009 | Anderson et al. | |
| 7,565,993 B2 | 7/2009 | Milliman et al. | |
| 7,588,175 B2 | 9/2009 | Timm et al. | |
| 7,588,176 B2 | 9/2009 | Timm et al. | |
| 7,588,177 B2 | 9/2009 | Racenet | |
| 7,604,151 B2 | 10/2009 | Hess et al. | |
| 7,617,961 B2 | 11/2009 | Viola | |
| 7,635,074 B2 * | 12/2009 | Olson | A61B 17/07207 227/176.1 |
| 7,641,091 B2 | 1/2010 | Olson et al. | |
| 7,645,285 B2 | 1/2010 | Cosgrove et al. | |
| 7,658,312 B2 | 2/2010 | Vidal et al. | |
| 7,665,647 B2 | 2/2010 | Shelton, IV et al. | |
| 7,669,746 B2 | 3/2010 | Shelton, IV | |
| 7,669,747 B2 | 3/2010 | Weisenburgh, II et al. | |
| 7,673,781 B2 | 3/2010 | Swayze et al. | |
| 7,673,782 B2 | 3/2010 | Hess et al. | |
| 7,690,547 B2 | 4/2010 | Racenet et al. | |
| 7,694,864 B2 | 4/2010 | Okada et al. | |
| 7,704,264 B2 | 4/2010 | Ewers et al. | |
| 7,708,684 B2 | 5/2010 | Demarais et al. | |
| 7,717,312 B2 | 5/2010 | Beetel | |
| 7,726,537 B2 | 6/2010 | Olson et al. | |
| 7,726,538 B2 | 6/2010 | Holsten et al. | |
| 7,726,539 B2 | 6/2010 | Holsten et al. | |
| 7,731,072 B2 | 6/2010 | Timm et al. | |
| 7,735,703 B2 | 6/2010 | Morgan et al. | |
| 7,744,613 B2 | 6/2010 | Ewers et al. | |
| 7,758,493 B2 | 7/2010 | Gingras | |
| 7,770,774 B2 | 8/2010 | Mastri et al. | |
| 7,775,967 B2 | 8/2010 | Gertner | |
| D624,182 S | 9/2010 | Thouement | |
| 7,793,812 B2 | 9/2010 | Moore et al. | |
| 7,794,475 B2 | 9/2010 | Hess et al. | |
| 7,815,092 B2 | 10/2010 | Whitman et al. | |
| 7,819,896 B2 | 10/2010 | Racenet | |
| 7,828,188 B2 | 11/2010 | Jankowski | |
| 7,837,079 B2 | 11/2010 | Holsten et al. | |
| 7,846,149 B2 | 12/2010 | Jankowski | |
| 7,857,184 B2 | 12/2010 | Viola | |
| 7,866,525 B2 | 1/2011 | Scirica | |
| 7,866,528 B2 * | 1/2011 | Olson | A61B 17/105 227/178.1 |
| 7,871,416 B2 | 1/2011 | Phillips | |
| 7,891,531 B1 | 2/2011 | Ward | |
| 7,891,533 B2 | 2/2011 | Green et al. | |
| 7,913,893 B2 | 3/2011 | Mastri et al. | |
| 7,918,869 B2 | 4/2011 | Saadat et al. | |
| 7,934,630 B2 | 5/2011 | Shelton, IV et al. | |
| 7,955,340 B2 | 6/2011 | Michlitsch et al. | |
| 7,959,050 B2 | 6/2011 | Smith et al. | |
| 7,963,907 B2 | 6/2011 | Gertner | |
| 7,966,799 B2 | 6/2011 | Morgan et al. | |
| 7,992,757 B2 | 8/2011 | Wheeler et al. | |
| 7,997,469 B2 * | 8/2011 | Olson | A61B 17/068 227/176.1 |
| 8,016,176 B2 | 9/2011 | Kasvikis et al. | |
| 8,020,741 B2 | 9/2011 | Cole et al. | |
| 8,028,884 B2 | 10/2011 | Sniffin et al. | |
| 8,033,442 B2 | 10/2011 | Racenet et al. | |
| 8,034,077 B2 | 10/2011 | Smith et al. | |
| 8,052,697 B2 | 11/2011 | Phillips | |
| 8,056,788 B2 | 11/2011 | Mastri et al. | |
| 8,061,577 B2 | 11/2011 | Racenet et al. | |
| 8,062,236 B2 | 11/2011 | Soltz | |
| 8,066,168 B2 | 11/2011 | Vidal et al. | |
| 8,070,034 B1 | 12/2011 | Knodel | |
| 8,070,036 B1 | 12/2011 | Knodel | |
| 8,087,563 B2 | 1/2012 | Milliman et al. | |
| 8,091,756 B2 * | 1/2012 | Viola | A61B 17/07292 227/178.1 |
| 8,096,459 B2 * | 1/2012 | Ortiz | A61B 17/072 227/176.1 |
| 8,113,406 B2 | 2/2012 | Holsten et al. | |
| 8,132,704 B2 | 3/2012 | Whitman et al. | |
| 8,141,762 B2 | 3/2012 | Bedi et al. | |
| 8,147,506 B2 | 4/2012 | Ortiz et al. | |
| 8,167,186 B2 | 5/2012 | Racenet et al. | |
| 8,172,122 B2 * | 5/2012 | Kasvikis | A61B 17/072 227/176.1 |
| 8,186,560 B2 | 5/2012 | Hess et al. | |
| 8,196,795 B2 | 6/2012 | Moore et al. | |
| 8,205,780 B2 | 6/2012 | Sorrentino et al. | |
| 8,210,415 B2 * | 7/2012 | Ward | A61B 17/07207 227/178.1 |
| 8,216,159 B1 | 7/2012 | Leiboff | |

(56) References Cited

U.S. PATENT DOCUMENTS

| | | | |
|---|---|---|---|
| 8,220,690 B2 | 7/2012 | Hess et al. |
| 8,226,602 B2 | 7/2012 | Quijana et al. |
| 8,245,898 B2 | 8/2012 | Smith et al. |
| 8,252,009 B2 | 8/2012 | Weller et al. |
| 8,256,655 B2 | 9/2012 | Sniffin et al. |
| 8,276,801 B2 | 10/2012 | Zemlok et al. |
| 8,292,153 B2 | 10/2012 | Jankowski |
| 8,308,725 B2 | 11/2012 | Bell et al. |
| 8,317,070 B2 | 11/2012 | Hueil et al. |
| 8,322,455 B2 | 12/2012 | Shelton, IV et al. |
| 8,328,061 B2 | 12/2012 | Kasvikis |
| 8,328,064 B2 | 12/2012 | Racenet et al. |
| 8,343,175 B2 | 1/2013 | Ewers et al. |
| 8,348,127 B2 | 1/2013 | Marczyk |
| 8,348,129 B2 | 1/2013 | Bedi et al. |
| 8,348,130 B2 | 1/2013 | Shah et al. |
| 8,348,131 B2 | 1/2013 | Omaits et al. |
| 8,353,436 B2 | 1/2013 | Kasvikis |
| 8,360,297 B2 | 1/2013 | Shelton, IV et al. |
| 8,365,973 B1 | 2/2013 | White et al. |
| 8,365,976 B2 | 2/2013 | Hess et al. |
| 8,382,775 B1 | 2/2013 | Bender et al. |
| 8,393,513 B2 | 3/2013 | Jankowski |
| 8,393,514 B2 | 3/2013 | Shelton, IV et al. |
| 8,403,956 B1 | 3/2013 | Thompson et al. |
| 8,408,442 B2 | 4/2013 | Racenet et al. |
| 8,424,739 B2 | 4/2013 | Racenet et al. |
| 8,439,244 B2 | 5/2013 | Holcomb et al. |
| 8,439,246 B1 | 5/2013 | Knodel |
| 8,449,560 B2 | 5/2013 | Roth et al. |
| 8,453,912 B2 | 6/2013 | Mastri et al. |
| 8,453,914 B2 | 6/2013 | Laurent et al. |
| 8,464,923 B2 | 6/2013 | Shelton, IV |
| 8,465,507 B2 | 6/2013 | Cosgrove et al. |
| 8,469,252 B2 | 6/2013 | Holcomb et al. |
| 8,469,977 B2* | 6/2013 | Balbierz ............ A61B 17/072 |
| | | | 606/153 |
| 8,479,969 B2 | 7/2013 | Shelton, IV |
| 8,485,412 B2 | 7/2013 | Shelton, IV et al. |
| 8,496,155 B2 | 7/2013 | Knodel |
| 8,496,156 B2 | 7/2013 | Sniffin et al. |
| 8,499,993 B2 | 8/2013 | Shelton, IV et al. |
| 8,523,041 B2 | 9/2013 | Ishitsuki et al. |
| 8,529,585 B2 | 9/2013 | Jacobs et al. |
| 8,540,128 B2 | 9/2013 | Shelton, IV et al. |
| 8,540,130 B2 | 9/2013 | Moore et al. |
| 8,544,712 B2 | 10/2013 | Jankowski |
| 8,561,872 B2 | 10/2013 | Wheeler et al. |
| 8,573,465 B2 | 11/2013 | Shelton, IV |
| 8,574,243 B2 | 11/2013 | Saadat et al. |
| 8,579,176 B2 | 11/2013 | Smith et al. |
| 8,579,178 B2 | 11/2013 | Holsten et al. |
| 8,590,762 B2 | 11/2013 | Hess et al. |
| 8,596,513 B2 | 12/2013 | Olson et al. |
| 8,608,043 B2 | 12/2013 | Scirica |
| 8,608,046 B2* | 12/2013 | Laurent ............ A61B 17/072 |
| | | | 227/175.2 |
| 8,613,384 B2 | 12/2013 | Pastorelli et al. |
| 8,616,431 B2 | 12/2013 | Timm et al. |
| 8,617,185 B2 | 12/2013 | Bonutti et al. |
| 8,628,544 B2 | 1/2014 | Farascioni |
| 8,628,547 B2 | 1/2014 | Weller et al. |
| 8,647,350 B2 | 2/2014 | Mohan et al. |
| 8,663,245 B2 | 3/2014 | Francischelli et al. |
| 8,668,130 B2 | 3/2014 | Hess et al. |
| 8,672,208 B2 | 3/2014 | Hess et al. |
| 8,672,830 B2 | 3/2014 | Dlugos, Jr. et al. |
| 8,701,958 B2 | 4/2014 | Shelton, IV et al. |
| 8,714,429 B2 | 5/2014 | Demmy |
| 8,720,766 B2 | 5/2014 | Hess et al. |
| 8,727,197 B2 | 5/2014 | Hess et al. |
| 8,727,199 B2 | 5/2014 | Wenchell |
| 8,733,613 B2 | 5/2014 | Huitema et al. |
| 8,740,035 B2 | 6/2014 | Mastri et al. |
| 8,758,392 B2 | 6/2014 | Crainich |
| 8,763,875 B2 | 7/2014 | Morgan et al. |
| 8,800,838 B2 | 8/2014 | Shelton, IV |
| 8,800,840 B2 | 8/2014 | Jankowski |
| 8,801,732 B2 | 8/2014 | Harris et al. |
| 8,808,161 B2 | 8/2014 | Gregg et al. |
| 8,808,325 B2 | 8/2014 | Hess et al. |
| 8,840,004 B2 | 9/2014 | Holsten et al. |
| 8,852,218 B2 | 10/2014 | Hughett, Sr. et al. |
| 8,864,009 B2 | 10/2014 | Shelton, IV et al. |
| 8,882,766 B2 | 11/2014 | Couture et al. |
| 8,899,465 B2 | 12/2014 | Shelton, IV et al. |
| 8,925,788 B2 | 1/2015 | Hess et al. |
| 8,945,163 B2 | 2/2015 | Voegele et al. |
| 8,956,390 B2 | 2/2015 | Shah et al. |
| 8,973,804 B2 | 3/2015 | Hess et al. |
| 8,978,956 B2 | 3/2015 | Schall et al. |
| 8,991,676 B2 | 3/2015 | Hess et al. |
| 8,991,677 B2 | 3/2015 | Moore et al. |
| 8,998,058 B2 | 4/2015 | Moore et al. |
| 9,011,437 B2 | 4/2015 | Woodruff et al. |
| 9,016,541 B2 | 4/2015 | Viola et al. |
| 9,033,203 B2 | 5/2015 | Woodard, Jr. et al. |
| 9,050,084 B2* | 6/2015 | Schmid ............ A61B 17/0686 |
| 9,066,721 B2 | 6/2015 | Ichihara et al. |
| 9,084,600 B1 | 7/2015 | Knodel et al. |
| 9,084,601 B2 | 7/2015 | Moore et al. |
| 9,095,339 B2 | 8/2015 | Moore et al. |
| 9,113,862 B2 | 8/2015 | Morgan et al. |
| 9,113,868 B2 | 8/2015 | Felder et al. |
| 9,119,627 B2 | 9/2015 | Cosgrove et al. |
| 9,138,226 B2 | 9/2015 | Racenet et al. |
| 9,149,325 B2 | 10/2015 | Worrell et al. |
| 9,155,528 B2 | 10/2015 | Bender et al. |
| 9,168,039 B1 | 10/2015 | Knodel |
| 9,179,911 B2 | 11/2015 | Morgan et al. |
| 9,180,035 B2 | 11/2015 | Stack et al. |
| 9,211,120 B2* | 12/2015 | Scheib ............ A61B 17/07207 |
| 9,216,019 B2 | 12/2015 | Schmid et al. |
| 9,254,131 B2 | 2/2016 | Soltz et al. |
| 9,289,206 B2 | 3/2016 | Hess et al. |
| 9,289,207 B2 | 3/2016 | Shelton, IV |
| 9,307,981 B2 | 4/2016 | Mikkaichi et al. |
| 9,314,362 B2 | 4/2016 | Bender et al. |
| 9,326,768 B2 | 5/2016 | Shelton, IV |
| 9,339,442 B2 | 5/2016 | Tai et al. |
| 9,345,478 B2 | 5/2016 | Knodel |
| 9,364,225 B2 | 6/2016 | Sniffin et al. |
| 9,370,362 B2 | 6/2016 | Petty et al. |
| 9,398,917 B2 | 7/2016 | Whitfield et al. |
| 9,408,604 B2 | 8/2016 | Shelton, IV et al. |
| 9,433,411 B2 | 9/2016 | Racenet et al. |
| 9,439,633 B2 | 9/2016 | O'Dea |
| 9,498,219 B2 | 11/2016 | Moore et al. |
| 9,549,733 B2 | 1/2017 | Knodel |
| 9,561,032 B2 | 2/2017 | Shelton, IV et al. |
| 9,603,595 B2 | 3/2017 | Shelton, IV et al. |
| 9,603,598 B2 | 3/2017 | Shelton, IV et al. |
| 9,615,952 B2 | 4/2017 | Scott et al. |
| 9,636,114 B2 | 5/2017 | Cole et al. |
| 9,675,355 B2 | 6/2017 | Shelton, IV et al. |
| 9,687,233 B2 | 6/2017 | Fernandez et al. |
| 9,687,237 B2* | 6/2017 | Schmid ............ A61B 17/07207 |
| 9,693,816 B2 | 7/2017 | Orszulak |
| 9,700,321 B2 | 7/2017 | Shelton, IV et al. |
| 9,706,991 B2 | 7/2017 | Hess et al. |
| 9,724,091 B2 | 8/2017 | Shelton, IV et al. |
| 9,724,093 B2* | 8/2017 | Farascioni ............ A61B 17/068 |
| 9,724,096 B2 | 8/2017 | Thompson et al. |
| 9,730,692 B2 | 8/2017 | Shelton, IV et al. |
| 9,775,613 B2 | 10/2017 | Shelton, IV et al. |
| 9,795,380 B2 | 10/2017 | Shelton, IV et al. |
| 9,801,627 B2 | 10/2017 | Harris et al. |
| 9,801,628 B2 | 10/2017 | Harris et al. |
| 9,801,630 B2 | 10/2017 | Harris et al. |
| 9,808,246 B2 | 11/2017 | Shelton, IV et al. |
| 9,808,257 B2 | 11/2017 | Armenteros et al. |
| 9,820,742 B2 | 11/2017 | Covach et al. |
| 9,827,002 B2 | 11/2017 | Hausen et al. |
| 9,844,370 B2 | 12/2017 | Viola et al. |

(56) References Cited

U.S. PATENT DOCUMENTS

| | | |
|---|---|---|
| 9,848,873 B2 | 12/2017 | Shelton, IV |
| 9,848,875 B2 | 12/2017 | Aronhalt et al. |
| 9,848,878 B2 | 12/2017 | Racenet et al. |
| 9,855,040 B2 | 1/2018 | Kostrzewski |
| 9,861,366 B2 | 1/2018 | Aranyi |
| 9,867,619 B2 * | 1/2018 | Williams ............. A61B 17/064 |
| 9,872,682 B2 | 1/2018 | Hess et al. |
| 9,901,344 B2 | 2/2018 | Moore et al. |
| 9,901,346 B2 | 2/2018 | Moore et al. |
| 9,913,646 B2 | 3/2018 | Shelton, IV |
| 9,924,947 B2 | 3/2018 | Shelton, IV et al. |
| 9,936,953 B2 | 4/2018 | Thompson et al. |
| 9,937,001 B2 | 4/2018 | Nakamura |
| 9,980,729 B2 | 5/2018 | Moore et al. |
| 9,999,426 B2 | 6/2018 | Moore et al. |
| 9,999,431 B2 | 6/2018 | Shelton, IV et al. |
| 10,004,505 B2 | 6/2018 | Moore et al. |
| 10,045,780 B2 | 8/2018 | Adams et al. |
| 10,085,751 B2 | 10/2018 | Overmyer et al. |
| 10,085,754 B2 | 10/2018 | Sniffin et al. |
| 10,130,360 B2 | 11/2018 | Olson et al. |
| 10,130,363 B2 | 11/2018 | Huitema et al. |
| 10,172,616 B2 | 1/2019 | Murray et al. |
| 10,194,912 B2 | 2/2019 | Scheib et al. |
| 10,226,250 B2 | 3/2019 | Beckman et al. |
| 10,231,734 B2 | 3/2019 | Thompson et al. |
| 10,238,517 B2 | 3/2019 | Gingras |
| 10,245,032 B2 | 4/2019 | Shelton, IV |
| 10,258,334 B2 | 4/2019 | Adams et al. |
| 10,265,073 B2 | 4/2019 | Scheib et al. |
| 10,278,695 B2 | 5/2019 | Milo |
| 10,278,699 B2 | 5/2019 | Thompson et al. |
| 10,278,707 B2 | 5/2019 | Thompson et al. |
| 10,285,712 B2 | 5/2019 | Cosgrove, III et al. |
| 10,285,837 B1 | 5/2019 | Thompson et al. |
| 10,292,706 B2 | 5/2019 | Jankowski |
| 10,307,161 B2 | 6/2019 | Jankowski |
| 10,307,163 B2 | 6/2019 | Moore et al. |
| 10,314,580 B2 | 6/2019 | Scheib et al. |
| 10,314,589 B2 | 6/2019 | Shelton, IV et al. |
| 10,342,538 B2 | 7/2019 | Racenet et al. |
| 10,383,628 B2 | 8/2019 | Kang et al. |
| 10,390,826 B2 | 8/2019 | Badawi |
| 10,405,856 B2 | 9/2019 | Knodel |
| 10,405,860 B2 | 9/2019 | Thompson et al. |
| 10,420,559 B2 | 9/2019 | Marczyk et al. |
| 10,420,560 B2 | 9/2019 | Shelton, IV et al. |
| 10,441,283 B1 | 10/2019 | Thompson et al. |
| 10,456,571 B2 | 10/2019 | Cairns |
| 10,470,911 B2 | 11/2019 | Thompson et al. |
| 10,485,540 B2 | 11/2019 | Hodgkinson et al. |
| 10,499,912 B2 | 12/2019 | Scheib et al. |
| 10,537,325 B2 | 1/2020 | Bakos et al. |
| 10,542,986 B2 | 1/2020 | Thompson et al. |
| 10,548,597 B2 * | 2/2020 | Dunki-Jacobs .... A61B 17/0644 |
| 10,610,226 B2 | 4/2020 | Shelton et al. |
| 10,624,638 B2 | 4/2020 | Thompson et al. |
| 10,687,807 B2 | 6/2020 | Simms et al. |
| 10,687,810 B2 | 6/2020 | Shelton, IV et al. |
| 10,687,814 B2 | 6/2020 | Dunki-Jacobs et al. |
| 10,716,564 B2 * | 7/2020 | Shelton, IV ..... A61B 17/07292 |
| 10,758,231 B2 | 9/2020 | Harris et al. |
| 10,849,623 B2 | 12/2020 | Dunki-Jacobs et al. |
| 10,912,562 B2 | 2/2021 | Dunki-Jacobs et al. |
| 10,966,721 B2 | 4/2021 | Dunki-Jacobs et al. |
| 10,987,108 B2 | 4/2021 | Thompson et al. |
| 11,173,060 B2 | 11/2021 | Thompson et al. |
| 11,197,672 B2 | 12/2021 | Dunki-Jacobs et al. |
| 2001/0044656 A1 | 11/2001 | Williamson, IV et al. |
| 2002/0143346 A1 | 10/2002 | Mcguckin, Jr. et al. |
| 2003/0125734 A1 | 7/2003 | Mollenauer |
| 2003/0135091 A1 | 7/2003 | Nakazawa et al. |
| 2003/0208209 A1 | 11/2003 | Gambale et al. |
| 2003/0220660 A1 | 11/2003 | Kortenbach et al. |
| 2004/0006351 A1 | 1/2004 | Gannoe et al. |
| 2004/0006372 A1 | 1/2004 | Racenet et al. |
| 2004/0068267 A1 | 4/2004 | Harvie et al. |
| 2004/0181239 A1 | 9/2004 | Dorn et al. |
| 2004/0215216 A1 | 10/2004 | Gannoe et al. |
| 2005/0006432 A1 | 1/2005 | Racenet et al. |
| 2005/0080444 A1 | 4/2005 | Kraemer et al. |
| 2005/0139633 A1 | 6/2005 | Wukusick et al. |
| 2005/0203547 A1 | 9/2005 | Weller et al. |
| 2005/0203548 A1 | 9/2005 | Weller et al. |
| 2005/0256533 A1 | 11/2005 | Roth et al. |
| 2006/0011698 A1 | 1/2006 | Okada et al. |
| 2006/0016853 A1 | 1/2006 | Racenet |
| 2006/0020277 A1 | 1/2006 | Gostout et al. |
| 2006/0036267 A1 | 2/2006 | Saadat et al. |
| 2006/0041270 A1 | 2/2006 | Lenker et al. |
| 2006/0085030 A1 | 4/2006 | Bettuchi et al. |
| 2006/0151568 A1 | 7/2006 | Weller et al. |
| 2006/0229665 A1 | 10/2006 | Wales et al. |
| 2006/0241692 A1 | 10/2006 | McGuckin et al. |
| 2007/0023477 A1 | 2/2007 | Whitman et al. |
| 2007/0027469 A1 | 2/2007 | Smith et al. |
| 2007/0029364 A1 | 2/2007 | Kruszynski et al. |
| 2007/0034666 A1 | 2/2007 | Holsten et al. |
| 2007/0034667 A1 | 2/2007 | Holsten et al. |
| 2007/0039997 A1 | 2/2007 | Mather et al. |
| 2007/0056932 A1 | 3/2007 | Whitman et al. |
| 2007/0075114 A1 | 4/2007 | Shelton et al. |
| 2007/0083233 A1 | 4/2007 | Ortiz et al. |
| 2007/0131732 A1 | 6/2007 | Holsten et al. |
| 2007/0179528 A1 | 8/2007 | Soltz et al. |
| 2007/0194079 A1 | 8/2007 | Hueil et al. |
| 2007/0194080 A1 | 8/2007 | Swayze et al. |
| 2007/0194081 A1 | 8/2007 | Hueil et al. |
| 2007/0213743 A1 | 9/2007 | McGuckin, Jr. |
| 2007/0246505 A1 | 10/2007 | Pace-Floridia et al. |
| 2007/0262116 A1 * | 11/2007 | Hueil ..................... B25C 5/0292 227/175.1 |
| 2008/0015631 A1 | 1/2008 | Lee et al. |
| 2008/0023522 A1 | 1/2008 | Olson et al. |
| 2008/0033457 A1 | 2/2008 | Francischelli et al. |
| 2008/0035702 A1 | 2/2008 | Holsten et al. |
| 2008/0041918 A1 | 2/2008 | Holsten et al. |
| 2008/0058716 A1 | 3/2008 | Dubrul et al. |
| 2008/0078800 A1 | 4/2008 | Hess et al. |
| 2008/0082124 A1 | 4/2008 | Hess et al. |
| 2008/0087707 A1 | 4/2008 | Jankowski |
| 2008/0097332 A1 | 4/2008 | Greenhalgh et al. |
| 2008/0149684 A1 | 6/2008 | Viola |
| 2008/0164297 A1 | 7/2008 | Holsten et al. |
| 2008/0169329 A1 | 7/2008 | Shelton et al. |
| 2008/0169332 A1 | 7/2008 | Shelton et al. |
| 2008/0190990 A1 | 8/2008 | Holsten et al. |
| 2008/0203134 A1 | 8/2008 | Shah et al. |
| 2008/0249404 A1 | 10/2008 | Mikkaichi et al. |
| 2008/0275480 A1 | 11/2008 | Jacobs et al. |
| 2008/0294179 A1 | 11/2008 | Balbierz et al. |
| 2008/0308602 A1 | 12/2008 | Timm et al. |
| 2009/0001122 A1 | 1/2009 | Prommersberger et al. |
| 2009/0001130 A1 | 1/2009 | Hess et al. |
| 2009/0012556 A1 | 1/2009 | Boudreaux et al. |
| 2009/0020584 A1 | 1/2009 | Soltz et al. |
| 2009/0078739 A1 | 3/2009 | Viola |
| 2009/0095791 A1 | 4/2009 | Eskaros et al. |
| 2009/0101692 A1 | 4/2009 | Whitman et al. |
| 2009/0134200 A1 * | 5/2009 | Tarinelli ........... A61B 17/07207 227/180.1 |
| 2009/0173766 A1 | 7/2009 | Wenchell |
| 2009/0209946 A1 | 8/2009 | Swayze et al. |
| 2009/0209986 A1 | 8/2009 | Stewart et al. |
| 2009/0212088 A1 | 8/2009 | Okada et al. |
| 2009/0255974 A1 * | 10/2009 | Viola ................ A61B 17/07207 227/176.1 |
| 2009/0261144 A1 | 10/2009 | Sniffin et al. |
| 2009/0308907 A1 | 12/2009 | Nalagatla et al. |
| 2010/0010512 A1 | 1/2010 | Taylor et al. |
| 2010/0072255 A1 * | 3/2010 | Olson ................ A61B 17/0682 227/178.1 |
| 2010/0072258 A1 | 3/2010 | Farascioni et al. |
| 2010/0108739 A1 | 5/2010 | Holsten et al. |

(56) References Cited

U.S. PATENT DOCUMENTS

| | | |
|---|---|---|
| 2010/0114124 A1 | 5/2010 | Kelleher et al. |
| 2010/0121356 A1 | 5/2010 | Hartmann et al. |
| 2010/0137904 A1 | 6/2010 | Wenchell |
| 2010/0145324 A1 | 6/2010 | Nihalani |
| 2010/0213240 A1 | 8/2010 | Kostrzewski |
| 2010/0256634 A1 | 10/2010 | Voegele et al. |
| 2010/0282820 A1 | 11/2010 | Kasvikis |
| 2010/0331866 A1 | 12/2010 | Surti et al. |
| 2011/0004062 A1 | 1/2011 | Asai et al. |
| 2011/0017800 A1 | 1/2011 | Viola |
| 2011/0036888 A1 | 2/2011 | Pribanic et al. |
| 2011/0046653 A1 | 2/2011 | Addington et al. |
| 2011/0071555 A1 | 3/2011 | McBrayer et al. |
| 2011/0084113 A1 | 4/2011 | Bedi et al. |
| 2011/0087169 A1 | 4/2011 | Parihar et al. |
| 2011/0087279 A1 | 4/2011 | Shah et al. |
| 2011/0152895 A1 | 6/2011 | Nyuli et al. |
| 2011/0160752 A1 | 6/2011 | Aguirre |
| 2011/0178454 A1 | 7/2011 | Gagner et al. |
| 2011/0186614 A1 | 8/2011 | Kasvikis |
| 2011/0190791 A1 | 8/2011 | Jacobs et al. |
| 2011/0208211 A1 | 8/2011 | Whitfield et al. |
| 2011/0226837 A1 | 9/2011 | Baxter, III et al. |
| 2011/0278343 A1 | 11/2011 | Knodel et al. |
| 2011/0290851 A1 | 12/2011 | Shelton, IV |
| 2011/0315739 A1 | 12/2011 | Sniffin et al. |
| 2012/0035631 A1 | 2/2012 | Hughett, Sr. et al. |
| 2012/0059400 A1 | 3/2012 | Williamson, IV et al. |
| 2012/0080494 A1 | 4/2012 | Thompson et al. |
| 2012/0116379 A1 | 5/2012 | Yates et al. |
| 2012/0123463 A1 | 5/2012 | Jacobs |
| 2012/0175398 A1 | 7/2012 | Sandborn et al. |
| 2012/0203247 A1 | 8/2012 | Shelton, IV et al. |
| 2012/0234899 A1 | 9/2012 | Scheib et al. |
| 2012/0234900 A1 | 9/2012 | Swayze |
| 2012/0248169 A1 | 10/2012 | Widenhouse et al. |
| 2012/0277525 A1 | 11/2012 | O'Dea |
| 2012/0286022 A1 | 11/2012 | Olson et al. |
| 2012/0289979 A1 | 11/2012 | Eskaros et al. |
| 2013/0062394 A1 | 3/2013 | Smith et al. |
| 2013/0075447 A1 | 3/2013 | Weisenburgh, II et al. |
| 2013/0075450 A1 | 3/2013 | Schmid et al. |
| 2013/0092718 A1 | 4/2013 | Soltz et al. |
| 2013/0105549 A1 | 5/2013 | Holsten et al. |
| 2013/0131440 A1 | 5/2013 | Gabriel |
| 2013/0146638 A1 | 6/2013 | Mandakolathur Vasudevan et al. |
| 2013/0146641 A1* | 6/2013 | Shelton, IV ......... A61B 17/105 227/176.1 |
| 2013/0146642 A1 | 6/2013 | Shelton, IV et al. |
| 2013/0153625 A1 | 6/2013 | Felder et al. |
| 2013/0153634 A1 | 6/2013 | Carter et al. |
| 2013/0153642 A1 | 6/2013 | Felder et al. |
| 2013/0161374 A1 | 6/2013 | Swayze et al. |
| 2013/0165774 A1 | 6/2013 | Nocca |
| 2013/0172929 A1 | 7/2013 | Hess et al. |
| 2013/0193190 A1 | 8/2013 | Carter et al. |
| 2013/0214025 A1 | 8/2013 | Zemlok et al. |
| 2013/0245652 A1 | 9/2013 | Cosgrove et al. |
| 2013/0256372 A1 | 10/2013 | Baxter, III et al. |
| 2013/0256375 A1 | 10/2013 | Shelton, IV et al. |
| 2013/0256377 A1 | 10/2013 | Schmid et al. |
| 2013/0284791 A1 | 10/2013 | Olson et al. |
| 2013/0306704 A1 | 11/2013 | Balbierz et al. |
| 2013/0327809 A1 | 12/2013 | Shelton, IV et al. |
| 2013/0334288 A1 | 12/2013 | Shelton, IV |
| 2013/0341374 A1 | 12/2013 | Shelton, IV et al. |
| 2014/0005678 A1 | 1/2014 | Shelton, IV et al. |
| 2014/0008412 A1 | 1/2014 | Zemlok et al. |
| 2014/0018722 A1 | 1/2014 | Scott et al. |
| 2014/0027493 A1 | 1/2014 | Jankowski |
| 2014/0046345 A1 | 2/2014 | Armenteros et al. |
| 2014/0074131 A1 | 3/2014 | Armenteros et al. |
| 2014/0081176 A1 | 3/2014 | Hassan |
| 2014/0082497 A1 | 3/2014 | Chalouhi et al. |
| 2014/0107698 A1 | 4/2014 | Inge |
| 2014/0110457 A1 | 4/2014 | Zhang et al. |
| 2014/0114121 A1 | 4/2014 | Trivedi |
| 2014/0131418 A1 | 5/2014 | Kostrzewski |
| 2014/0131419 A1 | 5/2014 | Bettuchi |
| 2014/0144968 A1 | 5/2014 | Shelton, IV |
| 2014/0148731 A1 | 5/2014 | Radl et al. |
| 2014/0171744 A1 | 6/2014 | Racenet et al. |
| 2014/0183242 A1* | 7/2014 | Farascioni ....... A61B 17/07207 227/176.1 |
| 2014/0184519 A1 | 7/2014 | Benchenaa et al. |
| 2014/0191015 A1 | 7/2014 | Shelton, IV |
| 2014/0214025 A1 | 7/2014 | Worrell et al. |
| 2014/0231489 A1 | 8/2014 | Balbierz et al. |
| 2014/0239037 A1 | 8/2014 | Boudreaux et al. |
| 2014/0257353 A1 | 9/2014 | Whitman et al. |
| 2014/0263570 A1 | 9/2014 | Hopkins et al. |
| 2014/0276932 A1 | 9/2014 | Williams et al. |
| 2014/0291379 A1 | 10/2014 | Schellin et al. |
| 2015/0048141 A1 | 2/2015 | Felder et al. |
| 2015/0083780 A1 | 3/2015 | Shelton, IV et al. |
| 2015/0133740 A1 | 5/2015 | Dierking et al. |
| 2015/0157318 A1 | 6/2015 | Beardsley et al. |
| 2015/0173746 A1 | 6/2015 | Baxter, III et al. |
| 2015/0173755 A1 | 6/2015 | Baxter, III et al. |
| 2015/0173762 A1 | 6/2015 | Shelton, IV et al. |
| 2015/0209034 A1 | 7/2015 | Viola et al. |
| 2015/0265276 A1 | 9/2015 | Huitema et al. |
| 2015/0297224 A1 | 10/2015 | Hall et al. |
| 2015/0297227 A1 | 10/2015 | Huitema et al. |
| 2015/0320423 A1 | 11/2015 | Aranyi |
| 2015/0351764 A1 | 12/2015 | Shelton, IV |
| 2016/0058439 A1* | 3/2016 | Shelton, IV ......... A61B 17/105 227/176.1 |
| 2016/0058447 A1 | 3/2016 | Posada et al. |
| 2016/0058594 A1 | 3/2016 | Armenteros et al. |
| 2016/0066916 A1 | 3/2016 | Overmyer et al. |
| 2016/0067074 A1 | 3/2016 | Thompson et al. |
| 2016/0089148 A1 | 3/2016 | Harris et al. |
| 2016/0166256 A1 | 6/2016 | Baxter, III et al. |
| 2016/0183945 A1 | 6/2016 | Shelton, IV et al. |
| 2016/0199061 A1 | 7/2016 | Shelton, IV et al. |
| 2016/0199088 A1 | 7/2016 | Shelton, IV et al. |
| 2016/0213302 A1 | 7/2016 | Frushour |
| 2016/0235409 A1 | 8/2016 | Shelton, IV et al. |
| 2016/0242768 A1 | 8/2016 | Moore et al. |
| 2016/0242769 A1 | 8/2016 | Moore et al. |
| 2016/0242770 A1 | 8/2016 | Moore et al. |
| 2016/0242783 A1 | 8/2016 | Shelton, IV et al. |
| 2016/0256152 A1 | 9/2016 | Kostrzewski |
| 2016/0262744 A1 | 9/2016 | Milo et al. |
| 2016/0262750 A1 | 9/2016 | Hausen et al. |
| 2016/0262921 A1 | 9/2016 | Balbierz et al. |
| 2016/0270792 A1 | 9/2016 | Sniffin et al. |
| 2016/0287251 A1 | 10/2016 | Shelton, IV et al. |
| 2016/0296272 A1 | 10/2016 | Heard |
| 2016/0324527 A1 | 11/2016 | Thompson et al. |
| 2016/0354085 A1 | 12/2016 | Shelton, IV et al. |
| 2016/0367250 A1 | 12/2016 | Racenet et al. |
| 2017/0007248 A1 | 1/2017 | Shelton, IV et al. |
| 2017/0014125 A1 | 1/2017 | Shelton, IV et al. |
| 2017/0027633 A1 | 2/2017 | Wham et al. |
| 2017/0055981 A1 | 3/2017 | Vendely et al. |
| 2017/0055991 A1 | 3/2017 | Kang |
| 2017/0056016 A1 | 3/2017 | Barton et al. |
| 2017/0086847 A1 | 3/2017 | DiNardo et al. |
| 2017/0095251 A1 | 4/2017 | Thompson et al. |
| 2017/0105728 A1 | 4/2017 | Scheib et al. |
| 2017/0172571 A1 | 6/2017 | Thompson et al. |
| 2017/0231633 A1 | 8/2017 | Marczyk et al. |
| 2017/0290588 A1 | 10/2017 | Thompson et al. |
| 2017/0303952 A1 | 10/2017 | Nativ et al. |
| 2017/0319210 A1 | 11/2017 | Moore et al. |
| 2017/0333041 A1 | 11/2017 | Moore et al. |
| 2017/0360447 A1 | 12/2017 | Armenteros et al. |
| 2017/0367697 A1 | 12/2017 | Shelton, IV et al. |
| 2018/0014826 A1 | 1/2018 | Scheib et al. |
| 2018/0036000 A1 | 2/2018 | Terada et al. |
| 2018/0036005 A1 | 2/2018 | Covach et al. |
| 2018/0092641 A1 | 4/2018 | Aranyi |

(56) References Cited

U.S. PATENT DOCUMENTS

| | | |
|---|---|---|
| 2018/0168594 A1 | 6/2018 | Shelton, IV et al. |
| 2018/0168620 A1 | 6/2018 | Huang et al. |
| 2018/0168633 A1 | 6/2018 | Shelton, IV et al. |
| 2018/0199939 A1 | 7/2018 | Thompson et al. |
| 2018/0199941 A1 | 7/2018 | Thompson et al. |
| 2018/0235625 A1 | 8/2018 | Shelton, IV et al. |
| 2018/0235626 A1 | 8/2018 | Shelton, IV et al. |
| 2018/0280020 A1 | 10/2018 | Hess et al. |
| 2018/0317905 A1 | 11/2018 | Olson et al. |
| 2019/0000455 A1 | 1/2019 | Adams et al. |
| 2019/0046186 A1 | 2/2019 | Dunki-Jacobs et al. |
| 2019/0046189 A1 | 2/2019 | Dunki-Jacobs et al. |
| 2019/0046190 A1 | 2/2019 | Dunki-Jacobs et al. |
| 2019/0046191 A1 | 2/2019 | Dunki-Jacobs et al. |
| 2019/0046192 A1 | 2/2019 | Dunki-Jacobs et al. |
| 2019/0046193 A1 | 2/2019 | Dunki-Jacobs et al. |
| 2019/0105042 A1 | 4/2019 | Huitema et al. |
| 2019/0133577 A1 | 5/2019 | Weadock et al. |
| 2019/0150924 A1 | 5/2019 | Thompson et al. |
| 2019/0209173 A1 | 7/2019 | Thompson et al. |
| 2019/0209175 A1 | 7/2019 | Thompson et al. |
| 2019/0224029 A1 | 7/2019 | Thompson et al. |
| 2019/0261985 A1 | 8/2019 | Adams et al. |
| 2019/0261991 A1 | 8/2019 | Beckman et al. |
| 2019/0269408 A1 | 9/2019 | Jankowski |
| 2019/0274677 A1 | 9/2019 | Shelton, IV |
| 2019/0274678 A1 | 9/2019 | Shelton, IV |
| 2019/0274679 A1 | 9/2019 | Shelton, IV |
| 2019/0274680 A1 | 9/2019 | Shelton, IV |
| 2019/0307450 A1 | 10/2019 | Thompson et al. |
| 2019/0343519 A1 | 11/2019 | Thompson et al. |
| 2019/0380742 A1 | 12/2019 | Hall et al. |
| 2019/0388092 A1 | 12/2019 | Thompson et al. |
| 2020/0008964 A1 | 1/2020 | Thompson et al. |
| 2020/0015822 A1 | 1/2020 | Marczyk et al. |
| 2020/0054326 A1 | 2/2020 | Harris et al. |
| 2020/0100790 A1 | 4/2020 | DiNardo et al. |
| 2020/0205810 A1 | 7/2020 | Posey et al. |
| 2020/0205827 A1* | 7/2020 | Bakos ............... A61B 17/0682 |
| 2020/0206805 A1 | 7/2020 | Nalagatla et al. |
| 2020/0214703 A1 | 7/2020 | Thompson et al. |
| 2020/0229818 A1 | 7/2020 | Thompson et al. |
| 2020/0297344 A1 | 9/2020 | Dunki-Jacobs et al. |
| 2020/0305865 A1 | 10/2020 | Shelton, IV |
| 2020/0305868 A1 | 10/2020 | Shelton, IV |
| 2020/0305869 A1 | 10/2020 | Shelton, IV |
| 2020/0305873 A1 | 10/2020 | Dunki-Jacobs et al. |
| 2020/0390443 A1 | 12/2020 | Thompson et al. |
| 2021/0128335 A1 | 5/2021 | Thompson et al. |
| 2021/0177411 A1 | 6/2021 | Williams |
| 2021/0369330 A1 | 12/2021 | Brandt et al. |
| 2021/0393319 A1 | 12/2021 | Shelton, IV et al. |

FOREIGN PATENT DOCUMENTS

| | | |
|---|---|---|
| EP | 399699 A1 | 11/1990 |
| EP | 503662 A1 | 9/1992 |
| EP | 666057 A2 | 8/1995 |
| EP | 0669104 A1 | 8/1995 |
| EP | 0399699 B1 | 11/1995 |
| EP | 0503662 B1 | 6/1997 |
| EP | 1090592 A1 | 4/2001 |
| EP | 1616526 A1 | 1/2006 |
| EP | 1722691 A1 | 11/2006 |
| EP | 1769766 A1 | 4/2007 |
| EP | 1774916 A1 | 4/2007 |
| EP | 1806101 A1 | 7/2007 |
| EP | 1875868 A1 | 1/2008 |
| EP | 1875870 A1 | 1/2008 |
| EP | 1938759 A2 | 7/2008 |
| EP | 2005896 A2 | 12/2008 |
| EP | 2005897 A2 | 12/2008 |
| EP | 2005898 A2 | 12/2008 |
| EP | 2005899 A2 | 12/2008 |
| EP | 2005900 A2 | 12/2008 |
| EP | 2005901 A1 | 12/2008 |
| EP | 1774916 B1 | 2/2009 |
| EP | 2019633 A1 | 2/2009 |
| EP | 2090247 A1 | 8/2009 |
| EP | 2111803 A2 | 10/2009 |
| EP | 2245993 A2 | 11/2010 |
| EP | 2319424 A1 | 5/2011 |
| EP | 2382928 A1 | 11/2011 |
| EP | 2019633 B1 | 8/2012 |
| FR | 2731895 A1 | 9/1996 |
| GB | 2298905 A | 9/1996 |
| WO | 2001054594 A1 | 8/2001 |
| WO | 2002060328 A1 | 8/2002 |
| WO | 03094747 A1 | 11/2003 |
| WO | 2007009099 A2 | 1/2007 |
| WO | 2007019268 A2 | 2/2007 |
| WO | 2007102152 A2 | 9/2007 |
| WO | 2008039238 A1 | 4/2008 |
| WO | 2008039249 A1 | 4/2008 |
| WO | 2008039250 A1 | 4/2008 |
| WO | 2008039270 A1 | 4/2008 |
| WO | 2008042021 A1 | 4/2008 |
| WO | 2008042022 A1 | 4/2008 |
| WO | 2008042043 A1 | 4/2008 |
| WO | 2008042044 A2 | 4/2008 |
| WO | 2008042045 A2 | 4/2008 |
| WO | 2008094210 A1 | 8/2008 |
| WO | 2008141288 A1 | 11/2008 |
| WO | 2009038550 A1 | 3/2009 |
| WO | 2010011661 A1 | 1/2010 |
| WO | 2011044032 A1 | 4/2011 |
| WO | 2011044032 A3 | 6/2011 |
| WO | 2011094700 A1 | 8/2011 |
| WO | 2012125615 A2 | 9/2012 |
| WO | 2012141679 A1 | 10/2012 |
| WO | 2013151888 A1 | 10/2013 |
| WO | 2014026170 A2 | 2/2014 |
| WO | 2014085099 A1 | 6/2014 |
| WO | 2015063609 A2 | 5/2015 |
| WO | WO-2015153324 A1 * | 10/2015 ........... A61F 5/0089 |
| WO | WO-2015153340 A2 * | 10/2015 ....... A61B 17/07207 |
| WO | 2016033221 A1 | 3/2016 |

OTHER PUBLICATIONS

Communication pursuant to Article 94(3) EPC received in European Patent Appln. No. 18 845 739.4; dated Apr. 28, 2022; 9 pages.

Examination Report received in Australian Patent Appln. No. 2022204678; dated Jul. 7, 2022; 4 pages.

Aladar de Petz, M.D., Aseptic Technic of Stomach Resections, 86 Annals of Surgery 388, Sep. 1927; 5 pages.

Geoffrey Parker, A New Stomach Clamp, 26 Postgrad Med. J. 550, 1950; 1 page.

John D. Harrah, M.D., A Lung Clamp for Use with Mechanical Staplers, 28 The Annals of Thoracic Surgery 489, Nov. 1979; 2 pages.

Felicien M. Steichen and Mark M. Ravitch, Stapling in Surgery, Figure 1-11C, Year Book Medical Publishers, Inc. 1984; 3 pages.

JP Regan et al., Early experience with two-stage laparoscopic Roux-en-Y gastric bypass as an alternative in the super-super obese patient, Obes Surg. Dec. 2003;13(6):861-4; abstract only; 2 pages.

510(k) Summary for AtriClip LAA Exclusion System with preloaded Gillinov-Cosgrove Clip, published Jun. 10, 2010; 6 pages.

510(k) Summary for TigerPaw(R) System, published Oct. 29, 2010; 6 pages.

Bram D. Zuckerman, M.D., Food and Drug Administration, Letter to AtriCure, Inc. Addressing Indication for Use of AtriClip LAA Exclusion System w/Pre-loaded Gillnov-Cosgrove Clip, Jun. 10, 2010; 3 pages.

M Jacobs et al., Laparoscopic sleeve gastrectomy: a retrospective review of 1- and 2-year results, Surg Endosc. Apr. 2010;24(4):781-5. doi: 10.1007/s00464-009-0619-8. Epub Aug. 19, 2009; abstract only; 2 pages.

CMS Description of Open Left Atrial Appendage Occlusion with "U" Fastener Implant, 1 page.

(56) References Cited

OTHER PUBLICATIONS

Pfiedler Enterprises, Science of Stapling: Urban Legend and Fact, Published Jun. 4, 2012; 38 pages.
Parikh, M.D. et al., Surgical Strategies That May Decrease Leak After Laparoscopic Sleeve Gastrectomy, 257 Annals of Surgery 231, Feb. 2013; 7 pages.
International Search Report and Written Opinion of the International Searching Authority for International Patent App. No. PCT/US2014/070869 dated Apr. 21, 2015; 17 pages.
International Preliminary Report on Patentability and Written Opinion of the International Searching Authority in Application No. PCT/US2015/048740 dated Mar. 7, 2017; 8 pages.
International Search Report and Written Opinion of the International Searching Authority for International Patent App. No. PCT/US2015/022904 dated Jun. 25, 2015; 6 pages.
International Search Report and Written Opinion of the International Searching Authority for International Patent App. No. PCT/US2015/022990 dated Sep. 30, 2015; 10 pages.
International Search Report and Written Opinion of the International Searching Authority for International Patent App. No. PCT/US2015/048740 dated Feb. 17, 2016; 12 pages.
European Search Report of the European Patent Office, Issued in European Application No. 15774247.9-1654; dated Dec. 23, 2016; 11 pages.
Supplementary Partial European Search Report of the European Patent Office, Issued in European Application No. 14872137; dated Dec. 12, 2016; 5 pages.
Australian Examination Report in Application No. 2016208416; dated May 18, 2017; 4 pages.
Supplementary European Search Report of the European Patent Office, Issued in European Application No. 14872137.6-1664; dated Mar. 28, 2017; 15 pages.
Supplementary European Search Report of the European Patent Office, Issued in European Application No. 15772561.5-1664; dated Mar. 15, 2017; 8 pages.
Australian Examination Report in Application No. 2015241193; dated Dec. 11, 2018; 5 pages.
Australian Examination Report in Application No. 2018203527; dated Oct. 22, 2018; 5 pages.
Examination Report of the European Patent Office, Issued in European Application No. 15772561.5-1122; dated Oct. 29, 2018; 7 pages.
International Search Report and Written Opinion of the International Searching Authority for International Patent App. No. PCT/US2018/046743 dated Dec. 4, 2018; 20 pages.
International Search Report of the State Intellectual Property Office of the People's Republic of China, Issued in Chinese Application No. 201480075706.2; dated Nov. 28, 2018; 3 pages.
Australian Examination Report in Application No. 2015241267; dated Feb. 25, 2019; 6 pages.
International Preliminary Report on Patentability and Written Opinion of the International Searching Authority in Application No. PCT/US2018/046743 dated Feb. 18, 2020; 17 pages.

\* cited by examiner

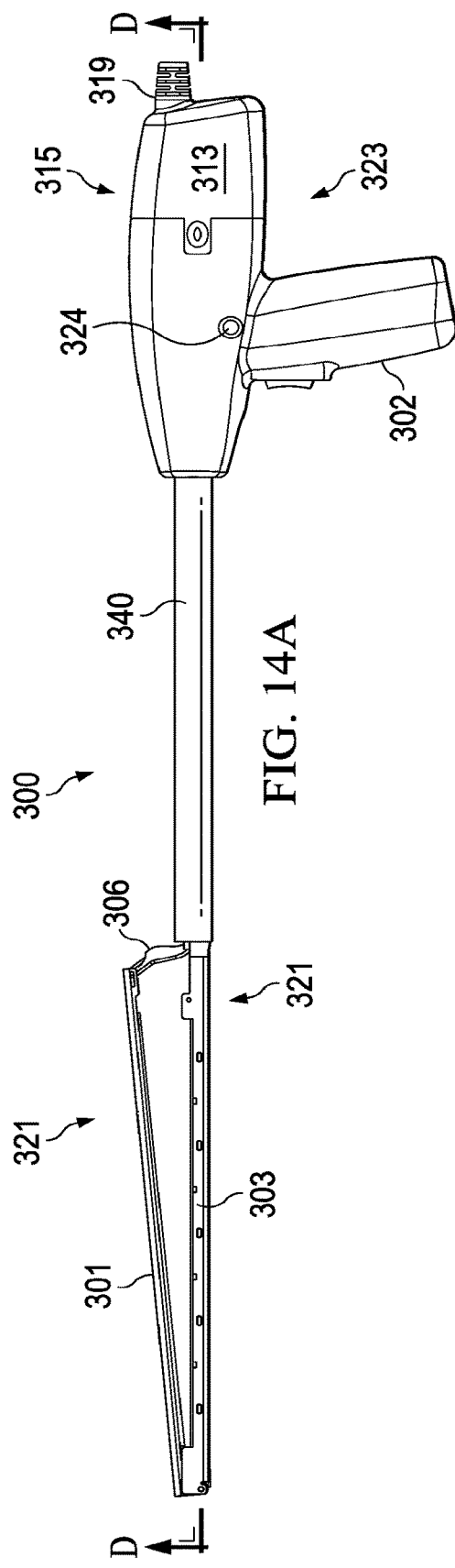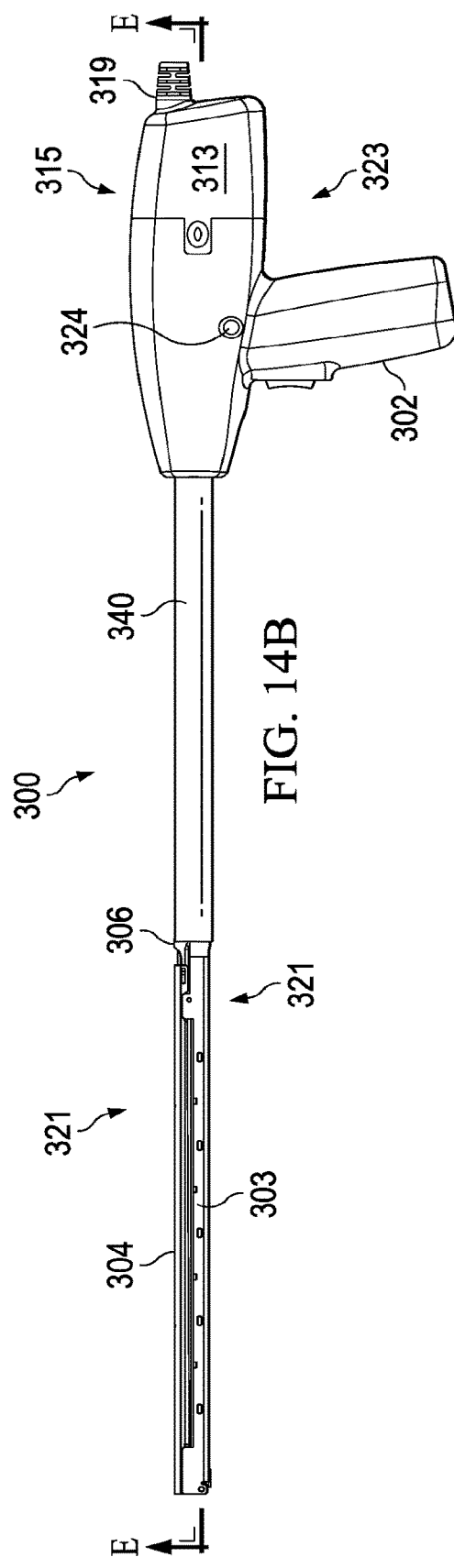
FIG. 14A
FIG. 14B

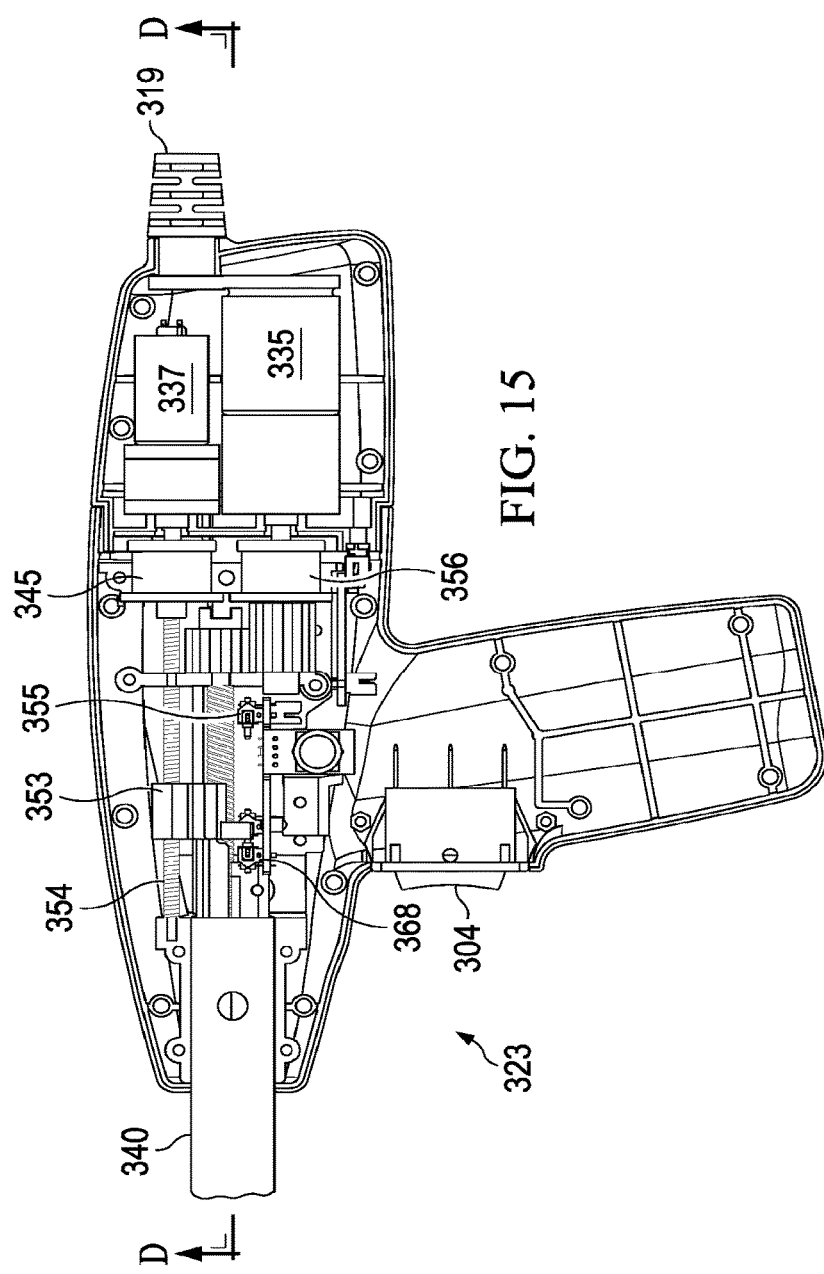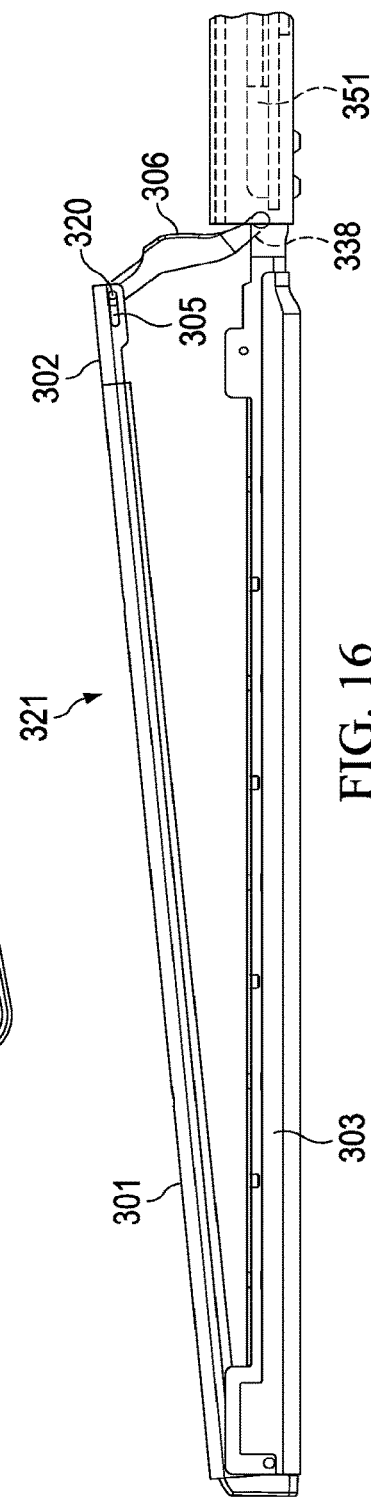

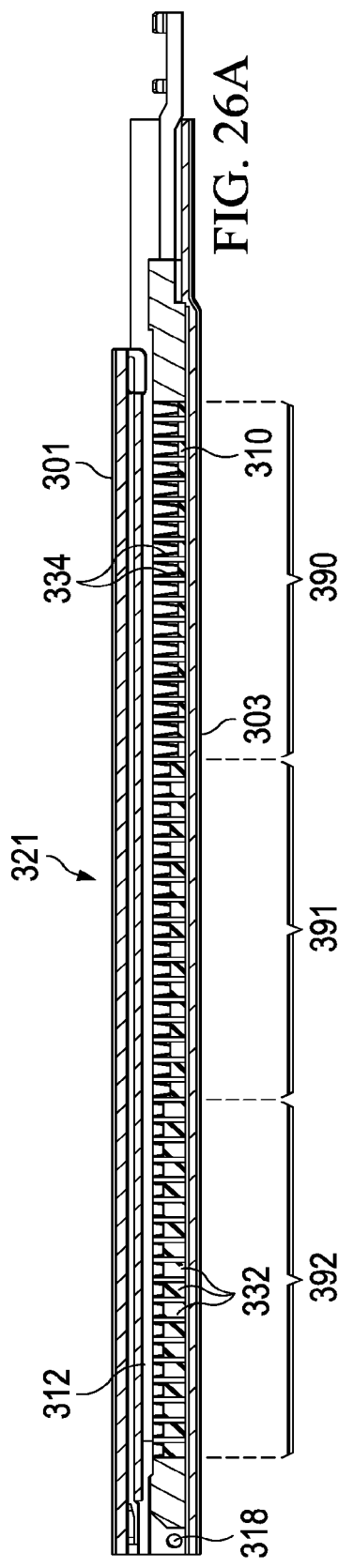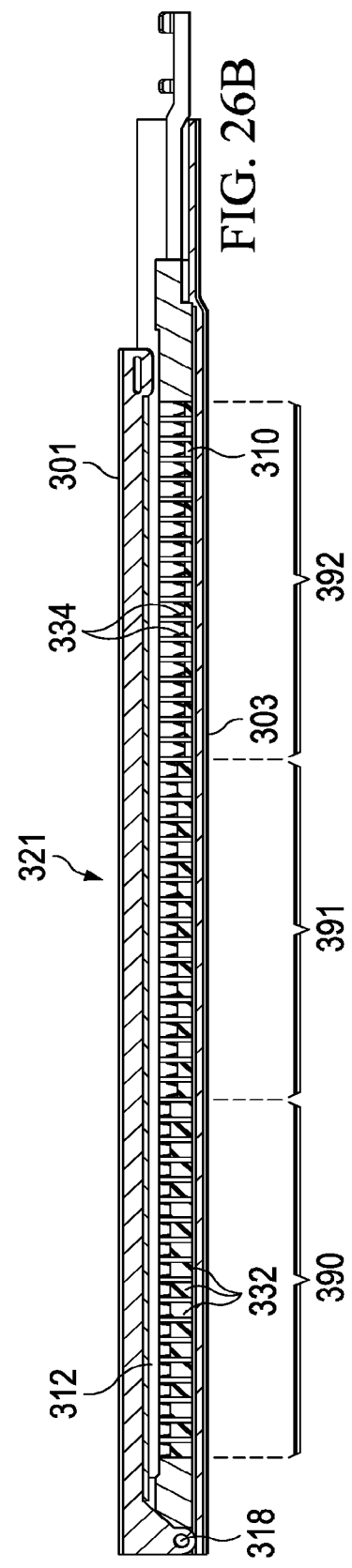

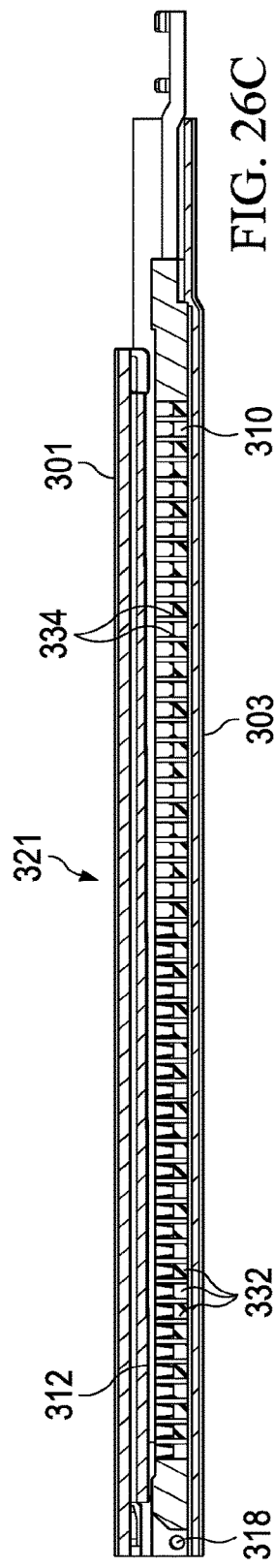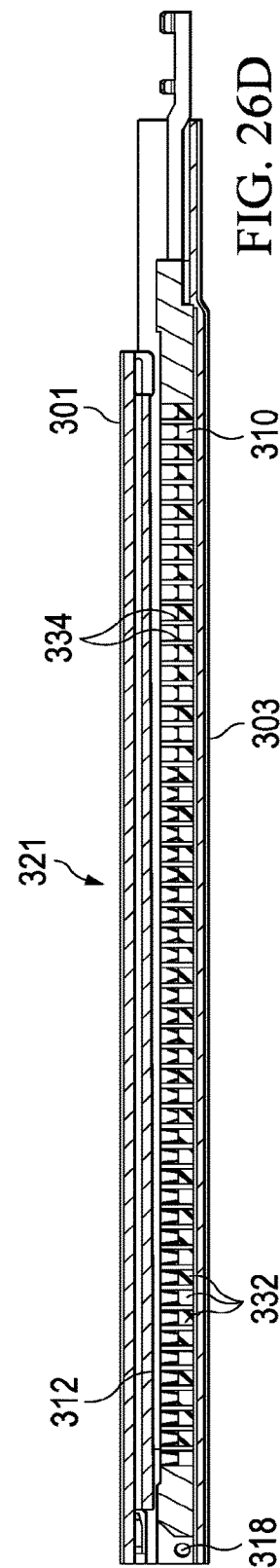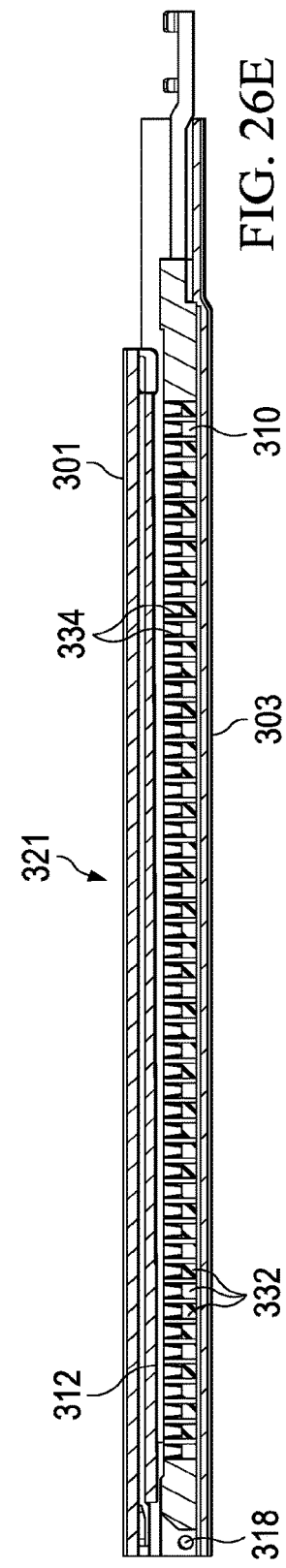

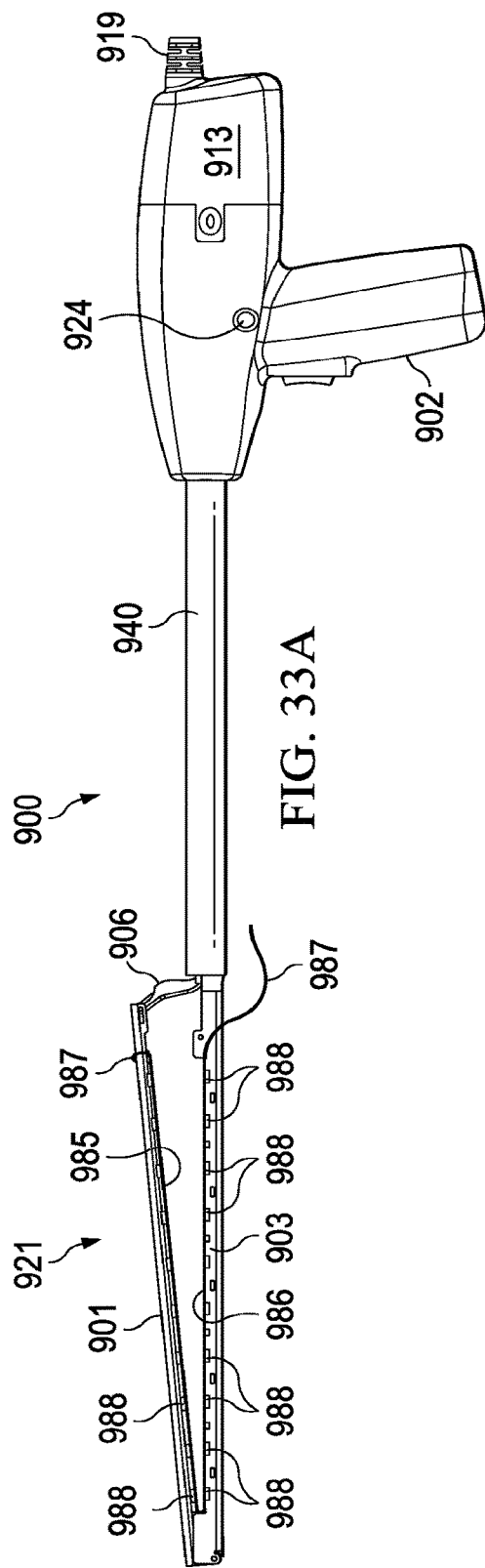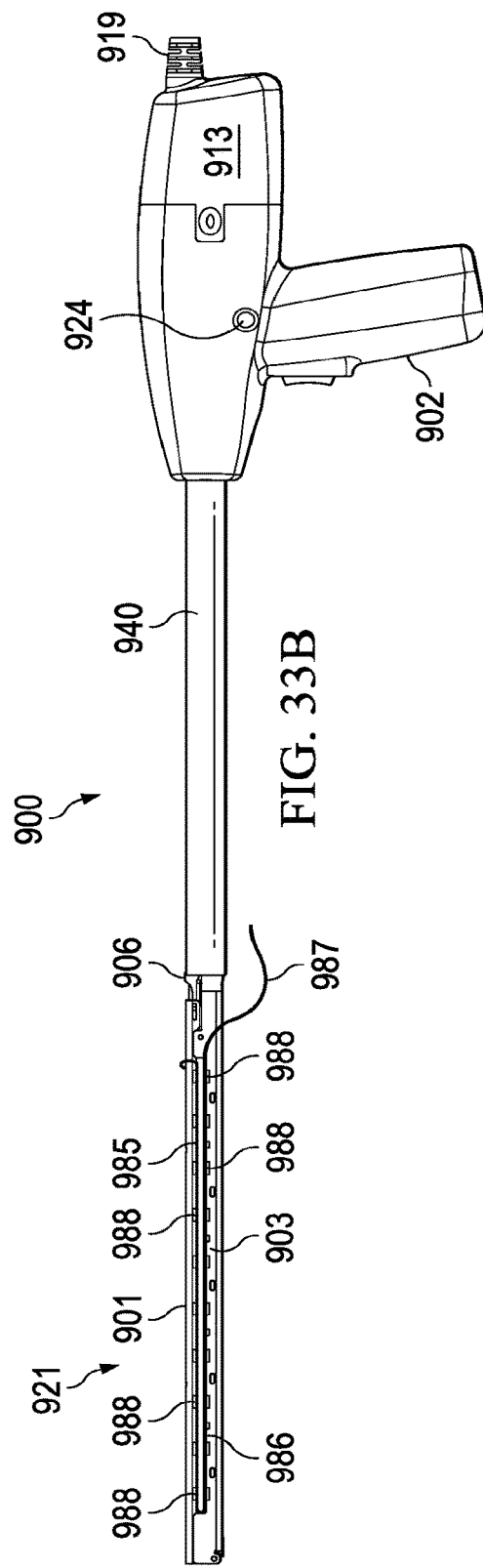

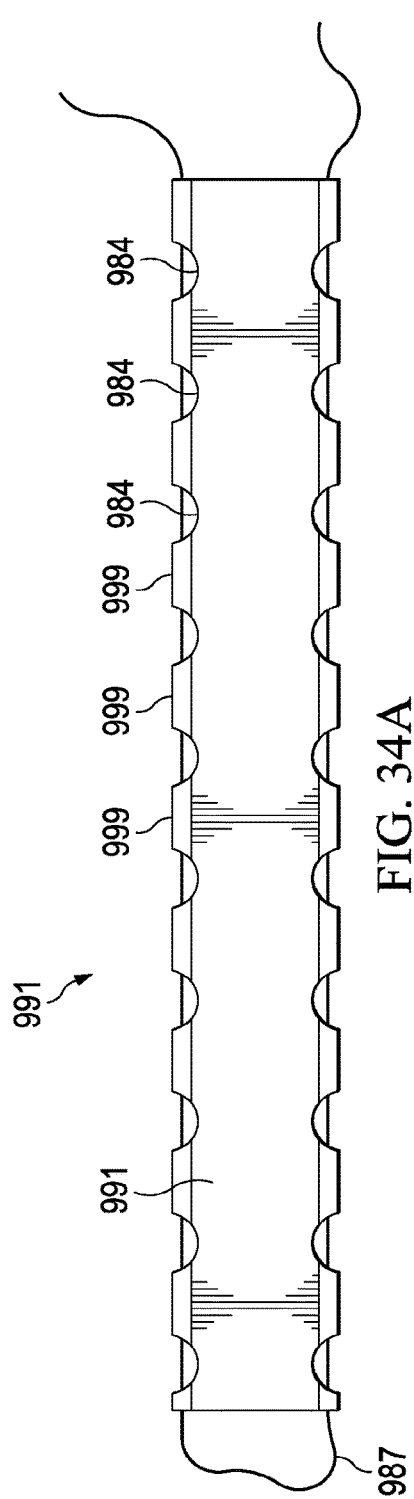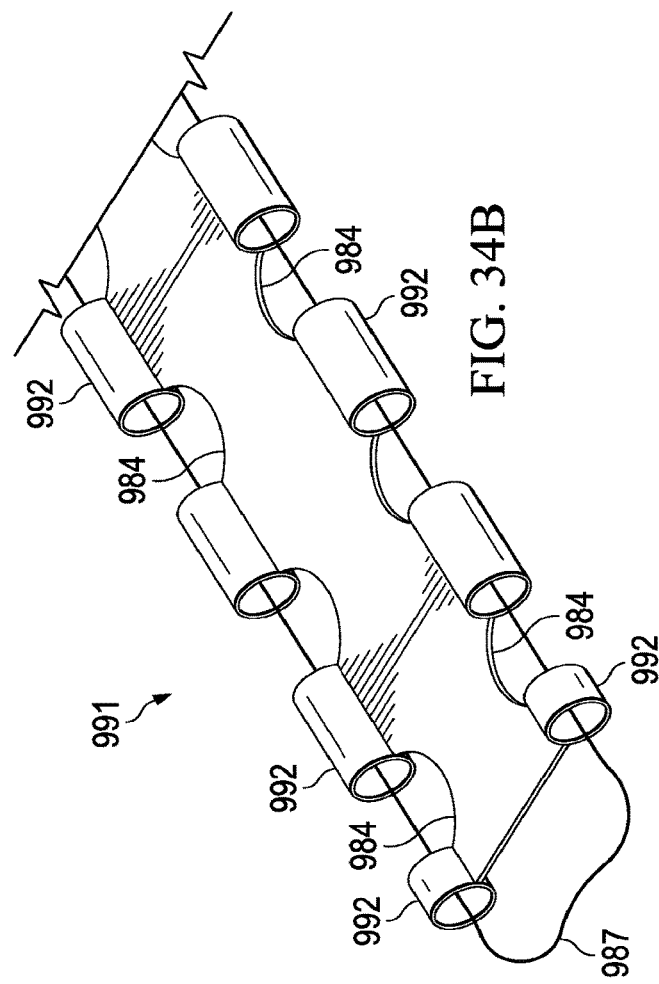

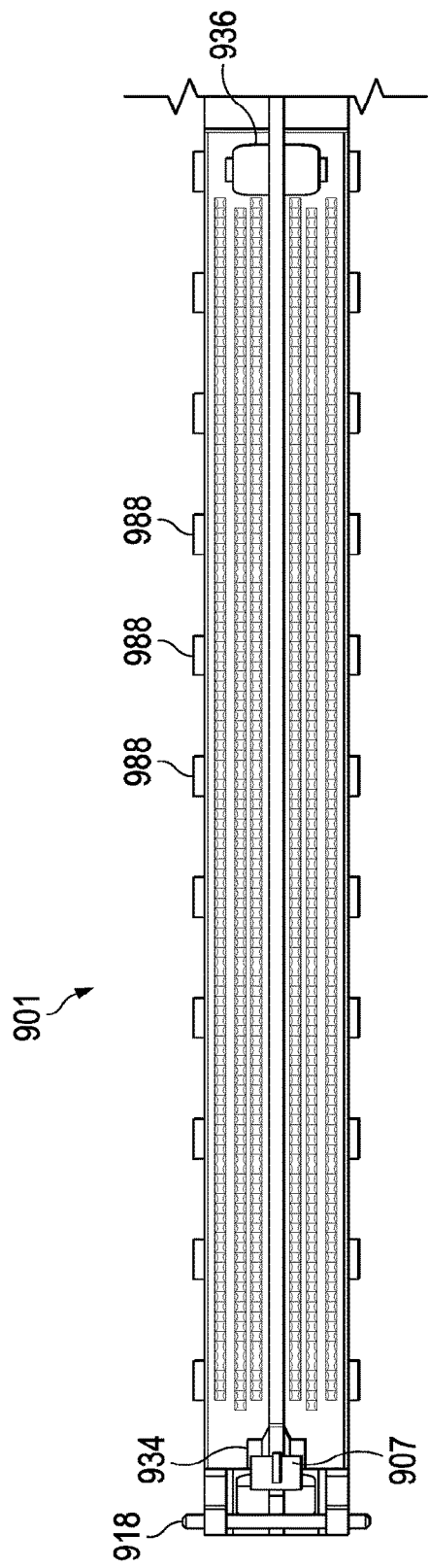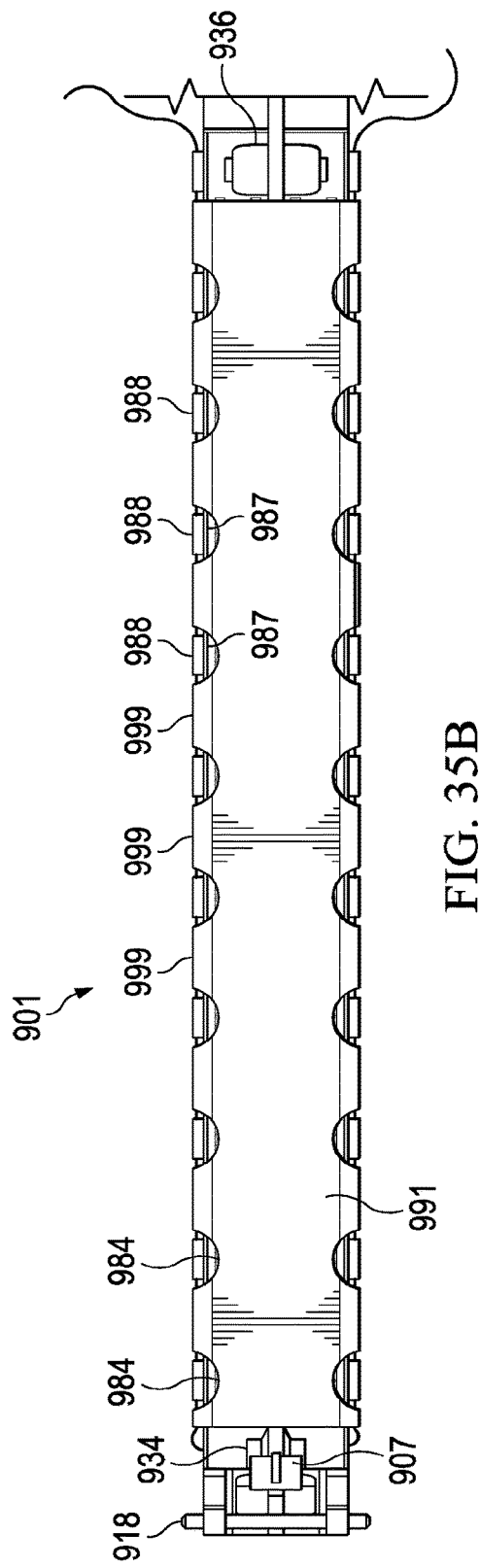

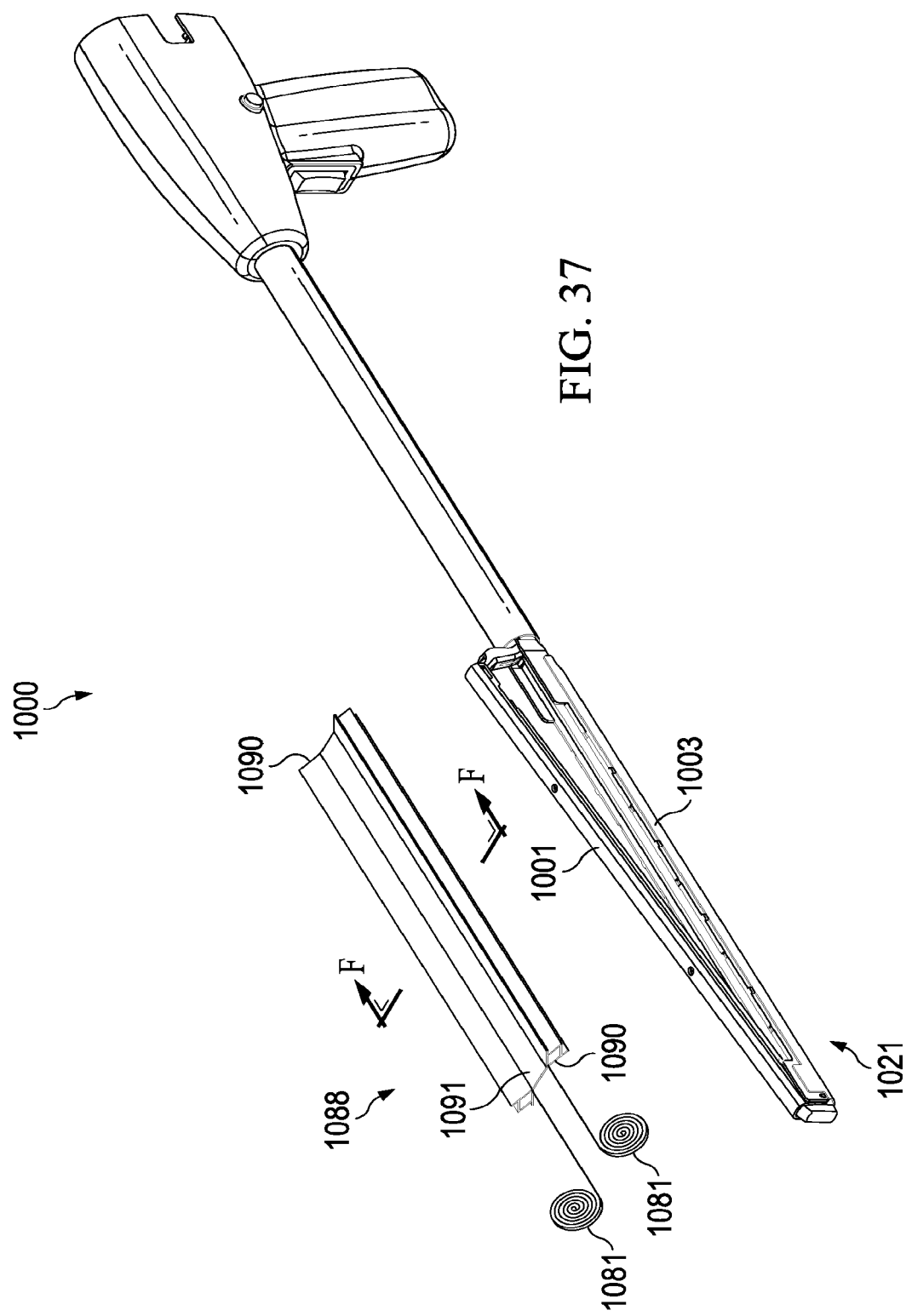

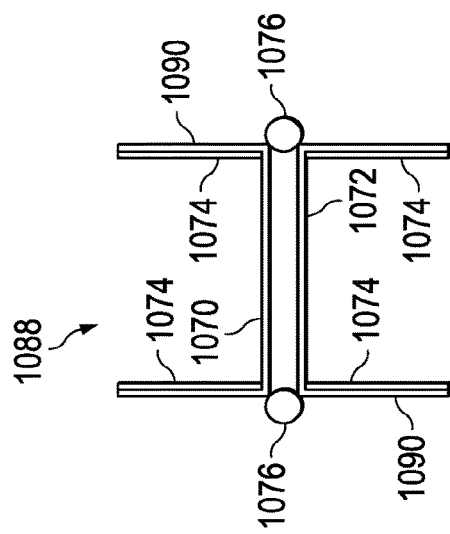
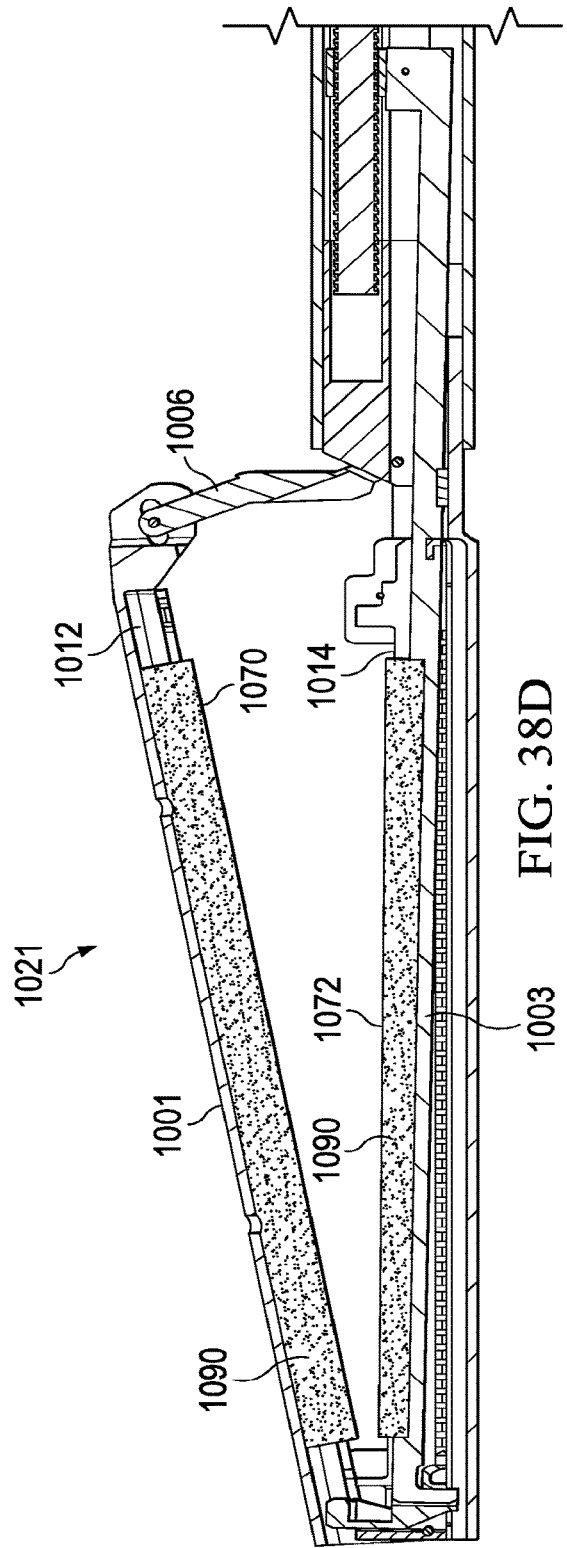

END EFFECTORS, SURGICAL STAPLING DEVICES, AND METHODS OF USING SAME

CROSS REFERENCE TO RELATED APPLICATIONS

This application is a continuation of U.S. Non-Provisional application Ser. No. 16/103,644 filed Aug. 14, 2018, which claims the priority benefit of: U.S. Provisional Patent Application No. 62/676,493 filed May 25, 2018; U.S. Provisional Patent Application No. 62/672,996, filed May 17, 2018; U.S. Provisional Patent Application No. 62/662,517, filed Apr. 25, 2018; U.S. Provisional Patent Application No. 62/579,703, filed Oct. 31, 2017; and U.S. Provisional Patent Application No. 62/545,324, filed Aug. 14, 2017, each of which is hereby incorporated herein by reference in its entirety.

TECHNICAL FIELD

Embodiments of the technology relate, in general, to surgical stapling technology, and in particular to end effectors and stapling devices and methods of using those devices in surgical procedures.

SUMMARY

Embodiments include an end effector for use by a surgeon to staple an anatomical structure of a patient, the end effector including a first jaw having a first end, a second end, a longitudinal axis, and an anvil having an anvil face; a second jaw having a first end, a second end, a longitudinal axis, and a cartridge operably configured to house a plurality of staples, the cartridge having a cartridge face; a first coupling that couples the first end of the first jaw to the first end of the second jaw; and a second coupling that movably couples the second end of the first jaw to the second end of the second jaw, where the second coupling includes a rigid link connected to the first jaw and the second jaw.

In certain embodiments, the first end of the first jaw is a distal end of the first jaw and the second end of the first jaw is a proximal end of the first jaw. In certain embodiments, the first coupling comprises a pin having a pin axis, the pin axis being transverse to the longitudinal axis of the first jaw and the longitudinal axis of the second jaw, wherein the pin pivotally couples the first end of the first jaw to the first end of the second jaw. In certain embodiments, the second coupling comprises a slot defined by the first jaw or the second jaw that retains the rigid link such that the rigid link is slidable within the slot. In certain embodiments, the slot has a length of from 3 millimeters to 8 millimeters. Certain embodiments include a plurality of staples at least partially retained by the cartridge of the second jaw. In certain embodiments, the plurality of staples retained at least partially by the cartridge are positioned between the first coupling and the second coupling. Certain embodiments include a blade having a cutting surface and at least one lateral arm. Certain embodiments include a channel defined by the first jaw or the second jaw to retain the at least one lateral arm of the blade. In certain embodiments, the blade is transitioned from a first position at a distal end of the end effector to a second position at a proximal end of the end effector such that the anatomical structure is resected.

Embodiments of a method of stapling an anatomical structure of a patient during a minimally invasive procedure, the anatomical structure having a first side and a second side, include the steps of providing an end effector including a first jaw having a first end, a second end, a longitudinal axis, and an anvil, the anvil having an anvil face; a second jaw having a first end, a second end, a longitudinal axis, and a cartridge retaining a plurality of staples, the cartridge having a cartridge face; a first coupling that couples the first end of the first jaw to the first end of the second jaw; a second coupling that movably couples the second end of the first jaw to the second end of the second jaw, where the second coupling includes a rigid link connected to the first jaw and the second jaw; and a knife coupled with and slidable relative to the first jaw or the second jaw; inserting the end effector through a trocar to access the anatomical structure; positioning the cartridge face on the first side of the anatomical structure; positioning the anvil face on the second side of the anatomical structure; operating the end effector to move the rigid link such that the first jaw is urged towards the second jaw to clamp the end effector on the anatomical structure; operating the end effector to urge the plurality of staples from the cartridge to staple the anatomical structure; and actuating the knife to cut the anatomical structure.

Embodiments include a surgical instrument to staple and resect an anatomical structure of a patient, the surgical instrument including an end effector, the end effector including a first jaw having a first end, a second end, a longitudinal axis, and an anvil, the anvil having an anvil face positionable on the first side of the anatomical structure; a second jaw having a first end, a second end, a longitudinal axis, and a cartridge operably configured to house a plurality of staples, the cartridge having a cartridge face positionable on the second side of the anatomical structure; a first coupling that couples the first end of the first jaw to the first end of the second jaw; and a second coupling that movably couples the second end of the first jaw to the second end of the second jaw, where the second coupling includes a rigid link connected to the first jaw and the second jaw; an elongate tube, the elongate tube having a proximal end and a distal end, where the distal end is coupled with the end effector; a handle, the handle having a proximal end and a distal end, where the distal end of the handle is coupled with the proximal end of the elongate tube; and a drive assembly including a motor to actuate the end effector.

Embodiments include a method of stapling an anatomical structure of a patient during a minimally invasive procedure, the anatomical structure having a first side and a second side, the method including the steps of providing an end effector including an anvil having a first end, a second end, an anvil face, a length, and a width, where the length of the anvil is at least ten times the width of the anvil; a cartridge having a first end, a second end, a cartridge face, a length, and a width, where the length of the cartridge is at least ten times the width of the anvil, the cartridge retaining a plurality of staples, where the first end of the anvil is coupled with the first end of the cartridge and the second end of the anvil is movably coupled to the second end of the cartridge; and a rigid link having a distal portion and a proximal portion, where the rigid link movably couples the second end of the anvil to the second end of the cartridge; inserting the end effector through a trocar to access the anatomical structure; positioning the cartridge face on the first side of the anatomical structure; positioning the anvil face on the second side of the anatomical structure; operating the end effector to move the rigid link such that the anvil is urged towards the cartridge to clamp the end effector on the anatomical structure; operating the end effector to urge the plurality of staples from the cartridge to staple the anatomical structure; and actuating a knife to cut the anatomical structure.

Embodiments include a surgical instrument to staple and resect an anatomical structure of a patient, the surgical instrument including an end effector, the end effector including an anvil having a first end, a second end, an anvil face, a length, and a width, wherein the length of the anvil is at least ten times the width of the anvil; a cartridge having a first end, a second end, a cartridge face, a length, and a width, where the length of the cartridge is at least ten times the width of the anvil, the cartridge being operably configured to house a plurality of staples, where the first end of the anvil is coupled with the first end of the cartridge and the second end of the anvil is movably coupled to the second end of the cartridge; and a rigid link having a distal portion and a proximal portion, where the rigid link movably couples the second end of the anvil to the second end of the cartridge; an elongate tube, the elongate tube having a proximal end and a distal end, where the distal end is coupled with the end effector; a handle, the handle having a proximal end and a distal end, where the distal end of the handle is coupled with the proximal end of the elongate tube; and a drive assembly having a motor to actuate the end effector.

Embodiments include a method of stapling an anatomical structure of a patient during a minimally invasive procedure, the anatomical structure having a first side and a second side, the method including the steps of providing an end effector including an anvil that includes a first end, a second end, and an anvil face; a cartridge retaining a plurality of staples, the cartridge having a first end, a second end, and a cartridge face, the cartridge face including a channel extending from the first end of the cartridge to the second end of the cartridge, where the first end of the cartridge is pivotally coupled with the first end of the anvil; a blade, the blade having a cutting surface and at least one elongated arm, where the at least one elongated arm is slidably engaged with the channel; and a rigid link that movably couples the second end of the anvil to the second end of the cartridge; inserting the end effector through a trocar to access the anatomical structure; positioning the cartridge face on the first side of the anatomical structure; positioning the anvil face on the second side of the anatomical structure; operating the end effector to move the rigid link such that the anvil is urged towards the cartridge to clamp the end effector on the anatomical structure; operating the end effector to urge the plurality of staples from the cartridge to staple the anatomical structure; and actuating the blade to cut the anatomical structure.

Embodiments include a surgical instrument to staple and resect an anatomical structure of a patient, the surgical instrument including an end effector, the end effector including an anvil that includes a first end, a second end, and an anvil face positionable on the first side of the anatomical structure; a cartridge operably configured to house a plurality of staples, the cartridge comprising a first end, a second end, and a cartridge face positionable on the second side of the anatomical structure, the cartridge face including a channel extending from the first end of the cartridge to the second end of the cartridge, where the first end of the cartridge is pivotally coupled with the first end of the anvil; a blade, the blade having a cutting surface and at least one elongated arm, where the at least one elongated arm is slidably engaged with the channel; and a rigid link that movably couples the second end of the anvil to the second end of the cartridge; an elongate tube, the elongate tube having a proximal end and a distal end, where the distal end is coupled with the end effector; a handle, the handle having a proximal end and a distal end, where the distal end of the handle is coupled with the proximal end of the elongate tube; and a drive assembly having a motor to actuate the end effector.

Embodiments include a method of stapling an anatomical structure of a patient during a minimally invasive procedure, the anatomical structure having a first side and a second side, the method including the steps of providing an end effector including a first jaw having a first end, a second end, an anvil having an anvil face, and a first channel; a second jaw having a first end, a second end, a cartridge having a cartridge face, and a second channel; a first coupling that couples the first end of the first jaw to the first end of the second jaw; a second coupling that movably couples the second end of the first jaw to the second end of the second jaw, where the second coupling includes a rigid link; and an I-shaped blade, the I-shaped blade including a blade portion having a cutting edge, at least one upper lateral arm, where the at least one upper lateral arm is slidably positioned in the first channel, and at least one lower lateral arm, where the at least one lower lateral arm is slidably positioned in the second channel; inserting the end effector through a trocar to access the anatomical structure; positioning the cartridge face on the first side of the anatomical structure; positioning the anvil face on the second side of the anatomical structure; operating the end effector to move the rigid link such that the anvil is urged towards the cartridge to clamp the end effector on the anatomical structure; operating the end effector to urge the plurality of staples from the cartridge to staple the anatomical structure; and actuating the I-shaped blade to cut the anatomical structure.

Embodiments include a surgical instrument to staple and resect an anatomical structure of a patient, the surgical instrument including an end effector, the end effector including a first jaw having a first end, a second end, an anvil having an anvil face, and a first channel; a second jaw having a first end, a second end, a cartridge having a cartridge face, and a second channel; a first coupling that couples the first end of the first jaw to the first end of the second jaw; a second coupling that movably couples the second end of the first jaw to the second end of the second jaw, where the second coupling includes a rigid link; and an I-shaped blade, the I-shaped blade including a blade portion having a cutting edge, at least one upper lateral arm, where the at least one upper lateral arm is slidably positioned in the first channel, and at least one lower lateral arm, where the at least one lower lateral arm is slidably positioned in the second channel; and an elongate tube, the elongate tube having a proximal end and a distal end, where the distal end is coupled with the end effector; a handle, the handle having a proximal end and a distal end, where the distal end of the handle is coupled with the proximal end of the elongate tube; and a drive assembly having a motor to actuate the end effector.

Embodiments include an end effector for use by a surgeon to staple an anatomical structure of a patient during a minimally invasive procedure, the end effector including an anvil having a first end, a second end, and an anvil face; a cartridge having a first end, a second end, and a cartridge face, the cartridge housing a plurality of staples, where the first end of the anvil is coupled with the first end of the cartridge and the second end of the anvil is coupled to the second end of the cartridge; and a buttress, the buttress including a first buttress member, the first buttress member being coupled with the anvil face such that the first buttress member covers a portion of the anvil face; and a second buttress member, the second buttress member being coupled with the cartridge face such that the second buttress member covers a portion of the anvil face.

Embodiments include an end effector for use by a surgeon to staple an anatomical structure of a patient during a minimally invasive procedure, the end effector including an anvil that includes a first end, a second end, and an anvil face positionable on the first side of the anatomical structure; a cartridge housing a plurality of staples, the cartridge having a first end, a second end, and a cartridge face positionable on the second side of the anatomical structure, where the first end of the cartridge is coupled with the first end of the anvil and the second end of the cartridge is coupled with the second end of the anvil; a blade, the blade having a cutting surface, where the blade is engageable with the anvil and the cartridge; and a buttress, the buttress being a planar section of material coupled with the anvil face or the cartridge face.

Embodiments include an end effector including a first jaw having a first end, a second end, an anvil having an anvil face, and a first channel; a second jaw having a first end, a second end, a cartridge having a cartridge face, and a second channel; a first coupling that couples the first end of the first jaw to the first end of the second jaw; a second coupling that couples the second end of the first jaw to the second end of the second jaw; an I-shaped blade, the I-shaped blade including a blade portion having a cutting edge; at least one upper lateral arm, where the at least one upper lateral arm is slidably positioned in the first channel; and at least one lower lateral arm, where the at least one lower lateral arm is slidably positioned in the second channel; and a buttress, the buttress being a planar section of material coupled with the anvil face or the cartridge face.

Embodiments include an end effector for use by a surgeon to staple an anatomical structure of a patient during a minimally invasive procedure, the anatomical structure having a first side and a second side, the end effector including a first jaw having a first end, a second end, a longitudinal axis, and an anvil, the anvil having an anvil face positionable on the first side of the anatomical structure; a second jaw having a first end, a second end, a longitudinal axis, and a cartridge housing a plurality of staples, the cartridge having a cartridge face positionable on the second side of the anatomical structure; a first coupling that couples the first end of the first jaw to the first end of the second jaw; a second coupling that couples the second end of the first jaw to the second end of the second jaw; and a buttress, the buttress including a first buttress member, the first buttress member being positioned adjacent the anvil face such that the first buttress member covers a portion of the anvil face; and a second buttress member, the second buttress member being positioned adjacent the cartridge face such that the second buttress member covers a portion of the cartridge face.

Embodiments include a method of stapling an anatomical structure of a patient during a minimally invasive procedure, the anatomical structure having a first side and a second side, the method including the steps of providing an end effector, the end effector including a first jaw having a first end, a second end, a longitudinal axis, and an anvil, the anvil comprising an anvil face positionable on the first side of the anatomical structure; a second jaw having a first end, a second end, a longitudinal axis, and a cartridge housing a plurality of staples, the cartridge having a cartridge face positionable on the second side of the anatomical structure; a first coupling that couples the first end of the first jaw to the first end of the second jaw; and a second coupling that couples the second end of the first jaw to the second end of the second jaw; providing a buttress, the buttress including a first buttress member and a second buttress member; attaching the first buttress member to the anvil face; attaching the second buttress member to the cartridge face; deploying the plurality of staples to puncture the first buttress member and the second buttress member; coupling the first buttress member and the second buttress member to the anatomical structure with the plurality of staples; and cutting the first buttress member and the second buttress member.

Embodiments include a method of stapling an anatomical structure of a patient during a minimally invasive procedure, the anatomical structure having a first side and a second side, the method including the steps of providing an end effector, the end effector including an anvil having a first end, a second end, and an anvil face; a cartridge having a first end, a second end, and a cartridge face, the cartridge housing a plurality of staples, where the first end of the anvil is coupled with the first end of the cartridge and the second end of the anvil is coupled to the second end of the cartridge; and providing a buttress, the buttress having a first buttress member and a second buttress member; attaching the first buttress member to the anvil face; attaching the second buttress member to the cartridge face; positioning the end effector proximate the anatomical structure; deploying the plurality of staples to puncture the first buttress member and the second buttress member; coupling the first buttress member and the second buttress member to the anatomical structure with the plurality of staples; and cutting the first buttress member and the second buttress member.

Embodiments include an end effector for stapling an anatomical structure, the anatomical structure having a first side and a second side, the end effector including an anvil, the anvil including a proximal end, a distal end, and an anvil face; an anvil blade channel defined by the anvil face, where the anvil blade channel is positioned to bisect the anvil face into a first half and a second half; a first pocket row including a plurality of first row staple pockets positioned on the first half of the anvil face; a second pocket row including a plurality of second row staple pockets positioned on the first half of the anvil face; a third pocket row including a plurality of third row staple pockets positioned on the first half of the anvil face; a fourth pocket row including a plurality of fourth row staple pockets positioned on the second half of the anvil face; a fifth pocket row including a plurality of fifth row staple pockets positioned on the second half of the anvil face; and a sixth pocket row including a plurality of sixth row staple pockets positioned on the second half of the anvil face; a cartridge having a proximal end, a distal end, and a cartridge face defining a cartridge blade channel, the cartridge being configured to retain a plurality of staples; and a blade, the blade having a cutting edge, wherein the blade is movable from a first position at the distal end of the cartridge to a second position at the proximal end of the cartridge.

Embodiments of the end effector can include a staple driver ramp operably configured to urge the plurality of staples from the cartridge towards the anvil face, where the staple driver ramp is movable from the distal end of the end effector to the proximal end of the end effector such that the end effector is operably configured to deploy the plurality of staples from the cartridge as the blade is moved from the distal end to the proximal end. In certain embodiments, the proximal end of the anvil is coupled with the proximal end of the cartridge and the distal end of the anvil is coupled with the distal end of the cartridge. In certain embodiments, the plurality of first row staple pockets has a uniform first depth, the plurality of second row staple pockets has a uniform second depth, and the uniform first depth is different from the uniform second depth. In certain embodiments, the uniform first depth is shallower than the uniform second depth. In certain embodiments, the first pocket row is spaced apart a first distance from the second pocket row, the second pocket row is spaced apart a second distance from the third pocket row, and the second distance is greater than the first distance. In certain embodiments, the first pocket row is offset from the second pocket row. In certain embodiments, the plurality of first row staple pockets includes a first portion having a first pocket depth and a second portion having a second pocket depth. In certain embodiments, the first portion is a proximal portion, the second portion is a distal portion, and the first pocket depth is deeper than the second pocket depth. In certain embodiments, each of the plurality of first row staple pockets has a different pocket depth. In certain embodiments, the plurality of first row staple pockets have a first depth corresponding with the plurality of fourth row staple pockets, the plurality of second row staple pockets have a second depth corresponding with the plurality of fifth row staple pockets, and the plurality of third row staple pockets have a third depth corresponding with the plurality of sixth row staple pockets. In certain embodiments, the first depth is shallower than the second depth and the second depth is shallower than the third depth. In certain embodiments, each of the plurality of first row staple pockets is sized to form a B-shaped staple, having a symmetrical configuration, in cooperation with the cartridge face. In certain embodiments, at least a portion of the plurality of first row staple pockets are sized to form a staple having an asymmetrical configuration. In certain embodiments, each of the plurality of first row staple pockets is sized to form a staple having a three-dimensional geometry. In certain embodiments, each of the plurality of first row staple pockets includes a first cavity having a first depth and a second cavity having a second depth, where the first depth is greater than the second depth.

Certain embodiments include an end effector for stapling an anatomical structure, the anatomical structure having a first side and a second side, the end effector including an anvil, the anvil including a proximal end, a distal end, and an anvil face; an anvil blade channel defined by the anvil face, where the anvil blade channel is positioned to bisect the anvil face into a first half and a second half; a first pocket row including a plurality of first row staple pockets positioned on the first half of the anvil face, where a first portion of the plurality of first row staple pockets has a first pocket depth and a second portion of the plurality of first row staple pockets has a second pocket depth different from the first pocket depth; a second pocket row including a plurality of second row staple pockets positioned on the first half of the anvil face, where a first portion of the plurality of second row staple pockets has the first pocket depth and a second portion of the plurality of second row staple pockets has the second pocket depth; a third pocket row including a plurality of third row staple pockets positioned on the second half of the anvil face, where a first portion of the plurality of third row staple pockets has the first pocket depth and a second portion of the plurality of third row staple pockets has the second pocket depth; and a fourth pocket row including a plurality of fourth row staple pockets positioned on the second half of the anvil face, where a first portion of the plurality of fourth row staple pockets has the first pocket depth and a second portion of the plurality of fourth row staple pockets has the second pocket depth; a cartridge having a proximal end, a distal end, and a cartridge face defining cartridge blade channel, the cartridge being configured to retain a plurality of staples; and a blade, the blade having a cutting edge, where the blade is movable from a first position at the distal end of the cartridge to a second position at a proximal end of the cartridge.

Embodiments include an end effector for stapling an anatomical structure, the anatomical structure having a first side and a second side, the end effector including an anvil, the anvil having a proximal end, a distal end, and an anvil face; an anvil blade channel defined by the anvil face, where the knife channel bisects the anvil face into a first half and a second half; a first inner pocket row including a plurality of first row staple pockets positioned on the first half of the anvil face, where each of the plurality of first row staple pockets has a depth of from 0.010 inches to 0.015 inches; a second middle pocket row including a plurality of second row staple pockets positioned on the first half of the anvil face, where each of the plurality of second row staple pockets has a depth of from 0.020 inches to 0.025 inches; a third outer pocket row including a plurality of third row staple pockets positioned on the first half of the anvil face, where each of the plurality of third row staple pockets has a depth from 0.030 inches to 0.035 inches; a fourth inner pocket row including a plurality of fourth row staple pockets positioned on the second half of the anvil face, where each of the plurality of fourth row staple pockets has a depth of from 0.010 inches to 0.050 inches; a fifth middle pocket row including a plurality of fifth row staple pockets positioned on the second half of the anvil face, where each of the plurality of fifth row staple pockets has a depth of from 0.010 inches to 0.050 inches; and a sixth outer pocket row including a plurality of sixth row staple pockets positioned on the second half of the anvil face, where each of the plurality of sixth row staple pockets has a depth from 0.010 inches to 0.050 inches; a cartridge having a proximal end, a distal end, and a cartridge face defining a cartridge blade channel, the cartridge being configured to retain a plurality of staples; and a blade, the blade having a cutting edge, wherein the blade is movable from a first position at the distal end of the cartridge to a proximal end of the cartridge.

Embodiments include an end effector for use by a surgeon to staple an anatomical structure of a patient during a minimally invasive procedure, the anatomical structure having a first side and a second side, the end effector including an anvil comprising a first end, a second end, an anvil face, a length, and a width, where the length of the anvil is at least ten times the width of the anvil; a cartridge having a first end, a second end, a cartridge face, a length, and a width, where the length of the cartridge is at least ten times the width of the anvil, the cartridge being operably configured to house a plurality of staples, where the first end of the anvil is coupled with the first end of the cartridge and the second end of the anvil is movably coupled to the second end of the cartridge; and a rigid link having a distal portion and a proximal portion, where the rigid link movably couples the second end of the anvil to the second end of the cartridge.

Embodiments include an end effector for use by a surgeon to staple an anatomical structure of a patient during a minimally invasive procedure, the anatomical structure having a first side and a second side, the end effector including an anvil that includes a first end, a second end, and an anvil face positionable on the first side of the anatomical structure, a cartridge operably configured to house a plurality of staples, the cartridge including a first end, a second end, and a cartridge face positionable on the second side of the anatomical structure, the cartridge face including a channel extending from the first end of the cartridge to the second end of the cartridge, where the first end of the cartridge is pivotally coupled with the first end of the anvil; a blade, the blade including a cutting surface and at least one elongated arm, where the at least one elongated arm is slidably engaged with the channel; and a rigid link that movably couples the second end of the anvil to the second end of the cartridge.

Embodiments include an end effector including a first jaw having a first end, a second end, an anvil having an anvil face, and a first channel; a second jaw having a first end, a second end, a cartridge having a cartridge face, and a second channel; a first coupling that couples the first end of the first jaw to the first end of the second jaw; a second coupling that movably couples the second end of the first jaw to the second end of the second jaw, where the second coupling includes a rigid link; and an I-shaped blade, the I-shaped blade including a blade portion having a cutting edge, at least one upper lateral arm, where the at least one upper lateral arm is slidably positioned in the first channel, and at least one lower lateral arm, where the at least one lower lateral arm is slidably positioned in the second channel.

Embodiments are directed to an end effector for use by a surgeon to staple an anatomical structure of a patient during a minimally invasive procedure, the anatomical structure having a first side and a second side. The end effector includes a first jaw having a first end, a second end, a longitudinal axis, and an anvil, the anvil having an anvil face positionable on the first side of the anatomical structure. A second jaw has a first end, a second end, a longitudinal axis, and a cartridge operably configured to house a plurality of staples, the cartridge having a cartridge face positionable on the second side of the anatomical structure. A first coupling couples the first end of the first jaw to the first end of the second jaw, and a second coupling movably couples the second end of the first jaw to the second end of the second jaw, wherein the second coupling includes a rigid link.

The first end of the first jaw may be a distal end of the first jaw and the second end of the first jaw may be a proximal end of the first jaw. The first coupling may include a pin having a pin axis, the pin axis being transverse to the longitudinal axis of the first jaw and the longitudinal axis of the second jaw, wherein the pin pivotally couples the first end of the first jaw to the first end of the second jaw.

The second coupling may include a slot within the first jaw or the second jaw that retains the rigid link such that the rigid link may be slidable within the slot. The slot may have a length of from 3 millimeters to 8 millimeters. A plurality of staples may be at least partially retained by the cartridge of the second jaw. The plurality of staples retained at least partially by the cartridge may be positioned between the first coupling and the second coupling. The end effector may further have a blade with a cutting surface and at least one lateral arm. There may also be a channel defined by the first jaw or the second jaw to retain the lateral arm of the blade. The blade may be transition from a first position at a distal end of the end effector to a second position at a proximal end of the end effector such that the anatomical structure may be resected.

In another embodiment an end effector for use by a surgeon to staple an anatomical structure of a patient having a first side and a second side during a minimally invasive procedure is disclosed. The end effector includes an anvil having a first end, a second end, an anvil face, a length, and a width, wherein the length of the anvil may be at least ten times the width of the anvil. The end effector also includes a cartridge having a first end, a second end, a cartridge face, a length, and a width, wherein the length of the cartridge may be at least ten times the width of the anvil. The cartridge may be operably configured to house a plurality of staples, wherein the first end of the anvil may be coupled with the first end of the cartridge and the second end of the anvil may be movably coupled to the second end of the cartridge.

A rigid link having a distal portion and a proximal portion may movably couple the second end of the anvil to the second end of the cartridge. The end effector may further have a control unit that is operable to move the rigid link in a first direction such that the anvil and the cartridge are spaced apart a first distance in a first position. The control unit may also be operable to move the rigid link a second direction such that the anvil and the cartridge are spaced apart a second distance in a second position, wherein the first distance may be greater than the second distance. For example, the first direction may be a distal direction and the second direction may be a proximal direction. The distal portion of the rigid link may be connected to the end effector, and the proximal portion of the rigid link may be connected to a control unit.

In another embodiment, the end effector may further have a ramp, wherein the rigid link may include a ramp surface operably configured such that when the ramp surface of the rigid link engages the ramp, the end effector transitions from a closed position to an open position. The rigid link may include an angled surface operably configured such that when the angled surface of the rigid link engages an elongate tube coupled with the end effector, the end effector transitions from an open position to a closed position. The end effector may further have an elongated slot defined by the anvil or cartridge that slidably retains the rigid link. The end effector may further have a blade with a cutting surface and at least one lateral arm, wherein the lateral arm may be slidably engaged with a channel defined by the anvil or cartridge. The blade may be transitioned from a first position at a distal end of the end effector to a second position at a proximal end of the end effector such that the anatomical structure may be resected.

In another embodiment an end effector for use by a surgeon to staple an anatomical structure of a patient has an anvil that includes a first end, a second end, and an anvil face positionable on the first side of the anatomical structure. A cartridge may be provided on the end-effector that is operably configured to house a plurality of staples, where the cartridge has a first end, a second end, and a cartridge face positionable on the second side of the anatomical structure. The cartridge face may include a channel extending from the first end of the cartridge to the second end of the cartridge, wherein the first end of the cartridge may be pivotally coupled with the first end of the anvil. A blade may have a cutting surface and at least one elongated arm, wherein the elongated arm may be slidably engaged with the channel. A rigid link may movably couple the second end of the anvil to the second end of the cartridge.

In one embodiment, at least one elongated arm of the blade urges each of a plurality of staples from the cartridge as the blade is advanced from a first position at a distal end of the cartridge to a second position at a proximal end of the cartridge. The blade may be I-shaped such that the blade compresses the anvil and the cartridge together during use. The first end of the cartridge may be a distal end and the second end of the cartridge may be a proximal end. The rigid link may be a monolithically formed unitary structure. The first end of the cartridge may be pivotally coupled with the first end of the anvil.

In another embodiment, an end effector is disclosed as having a first jaw having a first end, a second end, an anvil having an anvil face, and a first channel; a second jaw having a first end, a second end, a cartridge having a cartridge face, and a second channel; a first coupling that couples the first end of the first jaw to the first end of the second jaw; a second coupling that movably couples the second end of the first jaw to the second end of the second jaw, wherein the second coupling includes a rigid link; and an I-shaped blade. The I-shaped blade has a blade portion having a cutting edge; at least one upper lateral arm, wherein the at least one upper lateral arm may be slidably positioned in the first channel; and at least one lower lateral arm, wherein the at least one lower lateral arm may be slidably positioned in the second channel. The cartridge may include a plurality of staples.

In a further embodiment, a surgical instrument to staple and resect an anatomical structure of a patient is disclosed, the surgical instrument having: an end effector having; a first jaw having a first end, a second end, a longitudinal axis, and an anvil, the anvil having an anvil face positionable on the first side of the anatomical structure; a second jaw having a first end, a second end, a longitudinal axis, and a cartridge operably configured to house a plurality of staples, the cartridge having a cartridge face positionable on the second side of the anatomical structure; a first coupling that couples the first end of the first jaw to the first end of the second jaw; and a second coupling that movably couples the second end of the first jaw to the second end of the second jaw, wherein the second coupling includes a rigid link connected to the first jaw and the second jaw. The device may include a drive assembly having a motor that actuates the end effector.

The device may further include an elongate tube, the elongate tube having a proximal end and a distal end, wherein the distal end may be coupled with the end effector; and a handle, the handle having a proximal end and a distal end, wherein the distal end of the handle may be coupled with the proximal end of the elongate tube. For example, the first end of the first jaw may be a distal end of the first jaw and the second end of the first jaw may be a proximal end of the first jaw. The first coupling may include a pin having a pin axis, the pin axis being transverse to the longitudinal axis of the first jaw and the longitudinal axis of the second jaw, wherein the pin pivotally couples the first end of the first jaw to the first end of the second jaw. The second coupling may include a slot defined by the first jaw or the second jaw that retains the rigid link such that the rigid link may be slidable within the slot. The slot may have a length of from 3 millimeters to 8 millimeters. A plurality of staples may be at least partially retained by the cartridge of the second jaw, and may be positioned between the first coupling and the second coupling. The blade may have a cutting surface and at least one lateral arm, and a channel may be defined by the first jaw or the second jaw to retain the lateral arm of the blade. The blade may be transitioned from a first position at a distal end of the end effector to a second position at a proximal end of the end effector such that the anatomical structure may be resected.

In another embodiment, a surgical instrument to staple and resect an anatomical structure of a patient is described as having an end effector with an anvil having a first end, a second end, an anvil face, a length, and a width, wherein the length of the anvil may be at least ten times the width of the anvil; a cartridge having a first end, a second end, a cartridge face, a length, and a width, wherein the length of the cartridge may be at least ten times the width of the anvil, the cartridge being operably configured to house a plurality of staples, wherein the first end of the anvil may be coupled with the first end of the cartridge and the second end of the anvil may be movably coupled to the second end of the cartridge; and a rigid link having a distal portion and a proximal portion, wherein the rigid link movably couples the second end of the anvil to the second end of the cartridge. The instrument may include an elongate tube, the elongate tube having a proximal end and a distal end, wherein the distal end may be coupled with the end effector; and a handle, the handle having a proximal end and a distal end, wherein the distal end of the handle may be coupled with the proximal end of the elongate tube. The instrument may include a drive assembly having a motor that actuates the end effector.

The instrument may further have a control unit connected to the end effector, wherein the control unit may be operable to move the rigid link a first direction such that the anvil and the cartridge are spaced apart a first distance in a first position, and the control unit may be operable to move the rigid link a second direction such that the anvil and the cartridge are spaced apart a second distance in a second position, wherein the first distance may be greater than the second distance. The control unit may include a drive assembly having a motor that actuates the end effector.

For example, the first direction may be a distal direction and the second direction may be a proximal direction. A distal portion of the rigid link may be connected to the end effector and the proximal portion of the rigid link may be connected to the control unit. The surgical instrument may further have a ramp, wherein the rigid link may include a ramp surface operably configured such that when the ramp surface of the rigid link engages the ramp the end effector transitions from a closed position to an open position. The rigid link may also include an angled surface operably configured such that when the angled surface of the rigid link engages the elongate tube coupled with the end effector, the end effector transitions from an open position to a closed position.

The surgical instrument may further have an elongated slot defined by the anvil or cartridge that slidably retains the rigid link, and a blade having a cutting surface and at least one lateral arm, wherein the at least one lateral arm may be slidably engaged with a channel defined by the anvil or cartridge. The blade may be transitioned from a first position at a distal end of the end effector to a second position at a proximal end of the end effector such that the anatomical structure may be resected.

In yet another embodiment, a surgical instrument to staple and resect an anatomical structure of a patient is disclosed as having an end effector with: an anvil that includes a first end, a second end, and an anvil face positionable on the first side of the anatomical structure; a cartridge operably configured to house a plurality of staples, the cartridge having a first end, a second end, and a cartridge face positionable on the second side of the anatomical structure, the cartridge face including a channel extending from the first end of the cartridge to the second end of the cartridge, wherein the first end of the cartridge may be pivotally coupled with the first end of the anvil; a blade, the blade having a cutting surface and at least one elongated arm, wherein the at least one elongated arm may be slidably engaged with the channel; and a rigid link that movably couples the second end of the anvil to the second end of the cartridge. The instrument may further include an elongate tube, the elongate tube having a proximal end and a distal end, wherein the distal end may be coupled with the end effector; and a handle, the handle having a proximal end and a distal end, wherein the distal end of the handle may be coupled with the proximal end of the elongate tube. A plurality of staples may be housed at least partially by the cartridge. At least one elongated arm of the blade may be used to urge each of the plurality of staples from the cartridge as the blade advances from a first position at a distal end of the cartridge to a second position at a proximal end of the cartridge. The blade may be I-shaped such that the blade compresses the anvil and the cartridge during use.

In another embodiment, a surgical instrument useful to staple and resect an anatomical structure of a patient is disclosed as having an end effector with: a first jaw having a first end, a second end, an anvil having an anvil face, and a first channel; a second jaw having a first end, a second end, a cartridge having a cartridge face, and a second channel; a first coupling that couples the first end of the first jaw to the first end of the second jaw; a second coupling that movably couples the second end of the first jaw to the second end of the second jaw, wherein the second coupling includes a rigid link; and an I-shaped blade, the I-shaped blade having a blade portion with a cutting edge, at least one upper lateral arm, wherein the at least one upper lateral arm may be slidably positioned in the first channel, and at least one lower lateral arm, wherein the at least one lower lateral arm may be slidably positioned in the second channel.

The surgical instrument may further have an elongate tube with a proximal end and a distal end, wherein the distal end may be coupled with the end effector; and a handle, the handle having a proximal end and a distal end, wherein the distal end of the handle may be coupled with the proximal end of the elongate tube. At least one lower lateral arm may be operably configured to urge each of a plurality of staples from the cartridge when the I-shaped blade is actuated from a first position at a distal end of the end effector to a second position at a proximal end of the end effector.

In still a further embodiment, a method of stapling an anatomical structure of a patient during a minimally invasive procedure is disclosed, having the steps of: providing an end effector having; a first jaw having a first end, a second end, a longitudinal axis, and an anvil, the anvil having an anvil face; a second jaw having a first end, a second end, a longitudinal axis, and a cartridge retaining a plurality of staples, the cartridge having a cartridge face; a first coupling that couples the first end of the first jaw to the first end of the second jaw; a second coupling that movably couples the second end of the first jaw to the second end of the second jaw, wherein the second coupling includes a rigid link connected to the first jaw and the second jaw; and a knife coupled with and slidable relative to the first jaw or the second jaw. The method further includes the steps of: inserting the end effector through a trocar to access the anatomical structure; positioning the cartridge face on the first side of the anatomical structure; positioning the anvil face on the second side of the anatomical structure; operating the end effector to move the rigid link such that the first jaw may be urged towards the second jaw to clamp the end effector on the anatomical structure; operating the end effector to urge the plurality of staples from the cartridge to staple the anatomical structure; and actuating the knife to cut the anatomical structure.

The first end of the first jaw may be a distal end of the first jaw and the second end of the first jaw may be a proximal end of the first jaw. The first coupling may include a pin having a pin axis, the pin axis being transverse to the longitudinal axis of the first jaw and the longitudinal axis of the second jaw, wherein the pin pivotally couples the first end of the first jaw to the first end of the second jaw. The second coupling may include a slot defined by the first jaw or the second jaw that retains the rigid link such that the rigid link may be slidable within the slot.

Operating the end effector to urge the plurality of staples from the cartridge and actuating the knife to cut the anatomical structure may occur simultaneously. Actuating the knife to cut the anatomical structure may include advancing the knife from a first distal position to a second proximal position. Operating the end effector to urge the plurality of staples from the cartridge to staple the anatomical structure may include urging the plurality of staples from the cartridge between the first coupling and the second coupling. Actuating the knife to cut the anatomical structure may include advancing at least a portion of the knife through a channel defined by the first jaw or the second jaw. The knife may be transitioned from a first position at a distal end of the end effector to a second position at a proximal end of the end effector such that the anatomical structure may be resected.

In another embodiment, a method of stapling an anatomical structure of a patient during a minimally invasive procedure is described as having the steps of: providing an end effector having; an anvil having a first end, a second end, an anvil face, a length, and a width, wherein the length of the anvil may be at least ten times the width of the anvil; a cartridge having a first end, a second end, a cartridge face, a length, and a width, wherein the length of the cartridge may be at least ten times the width of the anvil, the cartridge retaining a plurality of staples, wherein the first end of the anvil may be coupled with the first end of the cartridge and the second end of the anvil may be movably coupled to the second end of the cartridge; and a rigid link having a distal portion and a proximal portion, wherein the rigid link movably couples the second end of the anvil to the second end of the cartridge; inserting the end effector through a trocar to access the anatomical structure; positioning the cartridge face on the first side of the anatomical structure; positioning the anvil face on the second side of the anatomical structure; operating the end effector to move the rigid link such that the anvil may be urged towards the cartridge to clamp the end effector on the anatomical structure; operating the end effector to urge the plurality of staples from the cartridge to staple the anatomical structure; and actuating a knife to cut the anatomical structure.

The method may further utilize a control unit connected to the end effector, wherein the control unit may be operable to move the rigid link a first direction such that the anvil and the cartridge are spaced apart a first distance in a first position. The control unit may be operable to move the rigid link a second direction such that the anvil and the cartridge are spaced apart a second distance in a second position, wherein the first distance may be greater than the second distance. For example, the first direction may be a distal direction and the second direction may be a proximal direction. The distal portion of the rigid link may be connected to the end effector and the proximal portion of the rigid link may be connected to a control unit. Operating the end effector to urge the plurality of staples from the cartridge and actuating the knife to cut the anatomical structure may occur simultaneously. Actuating the knife to cut the anatomical structure may include forming a sleeve in accordance with a sleeve gastrectomy procedure.

In yet another embodiment, a method of stapling an anatomical structure of a patient during a minimally invasive procedure is described, the anatomical structure having a first side and a second side, the method having the steps of: providing an end effector having; an anvil that includes a first end, a second end, and an anvil face; a cartridge retaining a plurality of staples, the cartridge having a first end, a second end, and a cartridge face, the cartridge face including a channel extending from the first end of the cartridge to the second end of the cartridge, wherein the first end of the cartridge may be pivotally coupled with the first end of the anvil; a blade, the blade having a cutting surface and at least one elongated arm, wherein the at least one elongated arm may be slidably engaged with the channel; and a rigid link that movably couples the second end of the anvil to the second end of the cartridge. The method further includes the steps of: inserting the end effector through a trocar to access the anatomical structure; positioning the cartridge face on the first side of the anatomical structure; positioning the anvil face on the second side of the anatomical structure; operating the end effector to move the rigid link such that the anvil may be urged towards the cartridge to clamp the end effector on the anatomical structure; operating the end effector to urge the plurality of staples from the cartridge to staple the anatomical structure; and actuating the blade to cut the anatomical structure.

In still a further embodiment of a method of stapling an anatomical structure of a patient during a minimally invasive procedure, the method involves the steps of: providing an end effector having; a first jaw having a first end, a second end, an anvil having an anvil face, and a first channel; a second jaw having a first end, a second end, a cartridge having a cartridge face, and a second channel; a first coupling that couples the first end of the first jaw to the first end of the second jaw; a second coupling that movably couples the second end of the first jaw to the second end of the second jaw, wherein the second coupling includes a rigid link; and an I-shaped blade, the I-shaped blade having; a blade portion having a cutting edge; at least one upper lateral arm, wherein the at least one upper lateral arm may be slidably positioned in the first channel; and at least one lower lateral arm, wherein the at least one lower lateral arm may be slidably positioned in the second channel. The method further involves the steps of: inserting the end effector through a trocar to access the anatomical structure; positioning the cartridge face on the first side of the anatomical structure; positioning the anvil face on the second side of the anatomical structure; operating the end effector to move the rigid link such that the anvil may be urged towards the cartridge to clamp the end effector on the anatomical structure; operating the end effector to urge the plurality of staples from the cartridge to staple the anatomical structure; and actuating the !-shaped blade to cut the anatomical structure. The anatomical structure may be a stomach and actuating the I-shaped blade to cut the anatomical structure may include forming a sleeve in accordance with a sleeve gastrectomy procedure.

At least one lower lateral arm may be operably configured to urge each of the plurality of staples from the cartridge when the I-shaped blade is actuated from a first position at a distal end of the end effector to a second position at a proximal end of the end effector. At least one lower lateral arm may be operably configured to urge each of the plurality of staples from the cartridge when the I-shaped blade is actuated from a first position at a distal end of the end effector to a second position at a proximal end of the end effector.

In one embodiment, an end effector is disclosed for use by a surgeon to staple an anatomical structure of a patient during a minimally invasive procedure. The anatomical structure has a first side and a second side. The end effector includes a first jaw having a first end, a second end and an anvil having an anvil face that may be positionable on the first side of the anatomical structure. A second jaw having a first end, a second end and a cartridge housing a plurality of staples is also included, the cartridge having a cartridge face that may be positionable on the second side of the anatomical structure.

A first coupling couples the first end of the first jaw to the first end of the second jaw, and a second coupling is included that movably couples the second end of the first jaw to the second end of the second jaw, wherein the second coupling includes a rigid link that is movably coupled to the first and second jaws. The end effector may have a longitudinal axis, wherein the first coupling includes a pin that rotatably couples the first jaw to the second jaw, wherein the rotation about the pin is transverse to the longitudinal axis. The pin that rotatably couples the first jaw to the second jaw may be slidably received within a slot in at least one of the first jaw or the second jaw.

At least one of the first jaw or the second jaw may slidably receive the rigid link within a slot as the first jaw is moved toward the second jaw. The rigid link may be coupled to the first jaw using a slot that allows motion of the rigid link in a first direction but limits motion of the rigid link in a direction perpendicular to the first direction. In one embodiment, the rigid link pushes the anvil open in the perpendicular direction. The slot may have a length of about 3 to about 8 millimeters, and preferably has a length of about 6 to about 7 millimeters. The plurality of staples may be positioned between the first coupling and the second coupling. The end effector may include a blade having a cutting surface and an elongated arm, the elongated arm extending at least from the blade positionable near the second end of the cartridge to the first end of the cartridge, where the arm slidably engages a cartridge channel.

In one particular embodiment, a surgical instrument is used to staple an anatomical structure of a patient, the anatomical structure having a first side and a second side. The surgical instrument may include an elongated end effector having a length and a width, wherein the length is at least ten times the width, the length defining a longitudinal axis, the longitudinal axis defining an axial direction perpendicular to the longitudinal axis. An anvil of the instrument may include a first end, a second end, and an anvil face. The instrument may also have a cartridge housing a plurality of staples that includes a first end, a second end, and a cartridge face, wherein the second end of the anvil may be movably coupled to the second end of the cartridge, wherein at least one of the anvil and the cartridge may include an elongated slot having its direction of elongation along the longitudinal axis. A rigid link may movably couple the first end of the anvil to the first end of the cartridge, wherein the rigid link may be retained within the elongated slot such that the rigid link is slidable along the elongated slot but limited in motion of the rigid link within the elongated slot in the axial direction. The surgical instrument may further include a control unit connected to the end effector by a tube along the longitudinal direction, wherein the control unit is operable to move the rigid link and separate the anvil and cartridge apart in the axial direction.

The elongated slot may allow longitudinal movement of the rigid link relative to the tube. The handle may operate to push the rigid link out of the tube and pull the rigid link into the tube. The rigid link may include a distal portion connected to the end effector and a proximal portion connected to the handle, wherein the end effector includes a ramp adjacent to the distal portion of the rigid link, the ramp being positioned to urge the rigid link in the axial direction as the rigid link moves distally.

The rigid link may include a ramp surface that slides along the ramp as the rigid link moves distally. The rigid link may include a distal portion connected to the end effector and a proximal portion connected to the handle, wherein the rigid link includes an angled surface between the distal portion and the proximal portion that engages the tube as the rigid link is pulled proximally by the handle, the tube engagement moving the anvil face and the cartridge face relative to one another.

The elongated slot may be offset from the longitudinal axis. Further, the elongated slot may have an elongation axis that intersects the longitudinal axis. The end effector may include a blade having a cutting surface and an elongated arm, the elongated arm extending at least from the blade positionable near the second end of the cartridge to the first end of the cartridge, where the arm slidably engages with a cartridge channel.

In another embodiment, an end effector for use by a surgeon to staple an anatomical structure of a patient during a minimally invasive procedure includes an anvil that includes a first end, a second end, and an anvil face that may be positionable on the first side of the anatomical structure. The end effector further incudes a cartridge housing a plurality of staples that include a first end, a second end, and a cartridge face that may be positionable on the second side of the anatomical structure. The cartridge face may include a channel extending from the second end to the first end, where a blade having a cutting surface and an elongated arm extending at least from the blade positionable near the second end of the cartridge to the first end of the cartridge engages with the cartridge channel. A rigid link may movably couple the first end of the anvil to the first end of the cartridge, wherein the second end of the anvil may be movably coupled to the second end of the cartridge. Each of the anvil and the cartridge may be insertable through a trocar and the end effector may be remotely operable from outside the patient with at least a portion of one of the anvil and the cartridge being movable toward the other to clamp the end effector to the anatomical structure.

The elongated arm of the blade may fill the cartridge channel proximally from the blade as the blade is moved from the second end to the first end, thereby forming staples in the anatomical structure as the blade cuts the anatomical structure. The blade may include an I-shaped portion having a top portion and a bottom portion connected by a middle blade portion, where the middle blade portion has a sharp cutting edge. The anvil includes a first opening near its first end and a second opening near its second end, each of the first opening and second opening operable to removably receive the top portion of the I-shaped portion when the anvil is approached to or departed from the cartridge. The elongated arm of the blade may fill the cartridge channel proximally from the blade as the blade is moved from the second end to the first end thereby forming staples in the anatomical structure as the blade cuts the anatomical structure.

The surgical instrument may further include a control unit connected to the end effector by a tube along the longitudinal direction, wherein the control unit is operable to move the rigid link and separate the anvil and cartridge apart in the axial direction. The rigid link may include a distal portion connected to the end effector and a proximal portion connected to the handle, wherein the end effector may include a ramp adjacent to the distal portion of the rigid link, the ramp positioned to urge the link in the axial direction as the link moves distally. The rigid link may include a ramp surface that slides along the ramp as the rigid link moves distally.

In a further embodiment, a stapler includes a first jaw having a first end, a second end and an anvil having an anvil face, a second jaw having a first end, a second end and a cartridge housing a plurality of staples, the cartridge having a cartridge face and a cartridge channel along the length of the cartridge. There is a first coupling that couples the first jaw to the second jaw and a second coupling that movably couples the second end of the first jaw to the second end of the second jaw, wherein the second coupling includes a rigid link that is movably coupled to the first and second jaws. A blade may be included that has an I-shaped portion having a top portion and a bottom portion connected by a middle blade portion, the middle blade portion having a sharp cutting edge, wherein the anvil has a first opening near its first end and a second opening near its second end, each of the first opening and second opening operable to removably receive the top portion of the I-shaped portion when the anvil is approached to or departed from the cartridge.

The stapler may include a rigid link that is retained within an elongated slot such that the rigid link is slidable along the elongated slot in a first direction but limited in motion of the rigid link within the elongated slot in a second direction. The elongated slot may be offset from a longitudinal axis of the stapler.

In still a further embodiment, a method of stapling an anatomical structure of a patient during a minimally invasive procedure is disclosed, where the anatomical structure has a first side and a second side. The method may include the steps of: providing a stapler with an end effector having a first jaw having a first end, a second end and an anvil having an anvil face; a second jaw having a first end, a second end and a cartridge housing a plurality of staples, the cartridge having a cartridge face; a first coupling that couples the first jaw to the second jaw; and a second coupling that movably couples the second end of the first jaw to the second end of the second jaw, wherein the second coupling includes a link that is movably coupled to the first and second jaws; inserting the end effector through a trocar to access the anatomical structure; positioning the cartridge face on the first side of the anatomical structure; positioning the anvil face on the second side of the anatomical structure; remotely operating the stapler from outside the patient to move the link such that at least a portion of one of the anvil or the cartridge is moved toward the other to clamp the end effector on the anatomical structure; and firing the stapler to simultaneously staple and cut the anatomical structure.

The end effector may have a longitudinal axis, wherein the first coupling includes a pin that rotatably couples the first jaw to the second jaw, wherein the rotation about the pin is transverse to the longitudinal axis. The method may further include the step of slidably receiving the link within a slot in at least one of the anvil or the cartridge when the end effector is clamped onto the anatomical structure, wherein the link is rigid. The rigid link may be coupled to the anvil using the slot such that the slot allows motion of the rigid link within the slot in a first direction but limits motion of the rigid link within the slot in a direction substantially perpendicular to the first direction. The rigid link may be coupled to the cartridge using the slot such that the slot allows motion of the rigid link in a first direction within the slot but the slot limits motion of the rigid link within the slot in a direction substantially perpendicular to the first direction.

The rigid link may be movable within the slot in the first direction over a length of about 3 to about 8 millimeters, and preferably the rigid link may be movable within the slot in the first direction through a length of about 7 millimeters. In one embodiment, the first coupling is distal to the second coupling and the method further includes the step of compressing the anatomical structure between the first coupling and the second coupling.

In a further embodiment, a method of using a surgical instrument to staple an anatomical structure of a patient is disclosed, where the anatomical structure has a first side and a second side, and the method includes the steps of: providing an elongated end effector having a length and a width, wherein the length is at least ten times the width, the length defining a longitudinal direction, the longitudinal direction defining an axial direction substantially perpendicular to the longitudinal direction; providing an anvil on the end effector that includes a first end, a second end, and an anvil face; providing a cartridge on the end effector that houses a plurality of staples and that includes a first end, a second end, and a cartridge face, wherein the second end of the anvil is movably coupled to the second end of the cartridge, wherein at least one of the anvil and the cartridge includes an elongated slot having its direction of elongation substantially along the longitudinal direction; actuating a rigid link that movably couples the first end of the anvil to the first end of the cartridge; and retaining the rigid link within the elongated slot as the surgical instrument is actuated such that the rigid link slides within the elongated slot along the longitudinal direction but is substantially limited in motion of the rigid link within the elongated slot in the axial direction.

The method may further include using a handle connected to the end effector by a tube along the longitudinal direction, wherein the method further includes the step of operating the handle to move the rigid link and separate the anvil and cartridge apart in the axial direction. The handle may operate to push the rigid link out of the tube and pull the rigid link into the tube. The rigid link may include a distal portion connected to the end effector and a proximal portion connected to the handle, wherein the end effector includes a ramp adjacent to the distal portion of the rigid link, wherein the method further includes the step of pushing the rigid link onto the ramp urging the rigid link in the axial direction as the rigid link is pushed. The rigid link may include a ramp surface, wherein the method further may include the step of sliding the ramp surface along the ramp as the rigid link moves. The rigid link may alternately include a distal portion connected to the end effector and a proximal portion connected to the handle, wherein the rigid link includes an angled surface between the distal portion and the proximal portion, wherein the method further includes the step of engaging the tube to compress the rigid link along the angled surface as the rigid link is pulled proximally by the handle, the tube engagement moving the anvil face and the cartridge face relative to one another.

In another embodiment, a method of stapling an anatomical structure of a patient during a minimally invasive procedure is disclosed, where the anatomical structure has a first side and a second side. The method includes the steps of: providing an anvil that includes a first end, a second end, and a face; positioning the anvil face on the first side of an anatomical structure; providing a cartridge housing a plurality of staples, the cartridge including a first end, a second end, and a face, the face including a channel extending from the second end to the first end, wherein the second end of the anvil is movably coupled to the second end of the cartridge; positioning the cartridge face on the second side of the anatomical structure; providing a blade having a cutting surface and an elongated arm, the elongated arm extending at least from the blade positionable near the second end of the cartridge to the first end of the cartridge, the arm slidably engaged with the cartridge channel; providing a rigid link that movably couples the first end of the anvil to the first end of the cartridge; moving the rigid link causing at least a portion of one of the anvil and the cartridge to move toward the other to clamp the anatomical structure between the anvil face and the cartridge face; and pulling the blade through the anatomical structure, simultaneously cutting and stapling the anatomical structure.

The elongated arm of the blade may substantially fill the cartridge channel proximally from the blade as the blade is moved from the second end to the first end. The blade may include a substantially I-shaped portion having a top portion and a bottom portion connected by a middle blade portion, the middle blade portion having a sharp cutting edge, wherein the anvil has a first opening near its first end and a second opening near its second end. The method may further include the step of receiving top portion of the substantially I-shaped portion into the first opening before pulling the blade through the anatomical structure and removing the top portion of the substantially I-shaped portion from the second opening after pulling the blade through the anatomical structure. The rigid link may include a distal portion connected to the anvil and a proximal portion connected to a handle, wherein the cartridge includes a ramp adjacent to the distal portion of the rigid link, wherein the method further includes the step of sliding the rigid link against the ramp to urge the rigid link in the axial direction as the rigid link slides. The rigid link may include a ramp surface that contacts the ramp as the rigid link slides. One or more of the methods disclosed herein may be useful for sleeve gastrectomy, vertical sleeve gastrectomy or procedures involving a resection of the stomach.

In another embodiment, an end effector for use by a surgeon to staple an anatomical structure of a patient during a minimally invasive procedure is disclosed, where the anatomical structure has a first side and a second side. The end effector includes an anvil that includes a first end, a second end, and an anvil face that may be positionable on the first side of the anatomical structure, the anvil having a plurality of anvil-side cord supports; a cartridge housing a plurality of staples and that includes a first end, a second end, and a cartridge face that may be positionable on the second side of the anatomical structure, the cartridge having a plurality of cartridge-side cord supports; and a link that movably couples the first end of the anvil to the first end of the cartridge, wherein the second end of the anvil is movably coupled to the second end of the cartridge, each of the anvil and the cartridge is insertable through a trocar and the end effector may be remotely operable from outside the patient to move at least a portion of one of the anvil and the cartridge toward the other to clamp the end effector on the anatomical structure. The plurality of anvil-side cord supports may have an opening facing away from the cartridge, and the plurality of cartridge-side cord supports may have an opening facing away from the anvil. The plurality of anvil-side cord supports and the plurality of cartridge-side cord supports may have an open tubular structure with a substantially C-shaped cross-sectional shape. In one particular embodiment the plurality of anvil-side cord supports and the plurality of cartridge-side cord supports have an open tubular structure with a substantially C-shaped cross-sectional shape, the opening of the C facing away from the cartridge on the plurality of anvil-side cord supports and the opening of the C facing away from the anvil on the plurality of cartridge-side cord supports.

The plurality of anvil-side cord supports and the plurality of cartridge-side cord supports may have a hollow tubular structure and the end effector may include a buttress material, the buttress material having a plurality of openings with a cord slidably positioned within the plurality of openings of the buttress material. In a preponderance of the plurality of openings of the buttress material, the cord may be slidably positioned within at least one of the plurality of anvil-side cord supports and the plurality of cartridge-side cord supports. The cartridge-side cord supports may be mounted to the cartridge frame.

At least one of the anvil and the cartridge may include an elongated slot wherein the end effector has a rigid link that movably couples the first end of the anvil to the first end of the cartridge, wherein the rigid link is retained within the elongated slot such that the rigid link is slidable along the elongated slot in a first direction but limited in motion of the rigid link within the elongated slot in a second direction.

In one embodiment, a surgical instrument to staple an anatomical structure of a patient is disclosed, where the anatomical structure has a first side and a second side. The surgical instrument includes an elongated end effector having a length and a width, wherein the length is at least ten times the width, the length defining a longitudinal direction, the longitudinal direction defining an axial direction substantially perpendicular to the longitudinal direction. The surgical instrument has an anvil that includes a first end, a second end, a plurality of anvil-side cord supports arranged from about the first end to about the second end, and an anvil face that may be positionable on the first side of the anatomical structure. The surgical instrument further includes a cartridge housing a plurality of staples and that includes a first end, a second end, a plurality of cartridge-side cord supports arranged from about the first end to about the second end, and a cartridge face that may be positionable on the second side of the anatomical structure, wherein the second end of the anvil is movably coupled to the second end of the cartridge. At least one of the anvil and the cartridge includes an elongated slot having its direction of elongation substantially along the longitudinal direction, and a rigid link that movably couples the first end of the anvil to the first end of the cartridge, wherein the rigid link is retained within the elongated slot such that the rigid link is slidable along the elongated slot but substantially limited in motion of the rigid link within the elongated slot in the axial direction.

In one particular embodiment the plurality of anvil-side cord supports have an opening facing substantially away from the cartridge, and the plurality of cartridge-side cord supports have an opening facing substantially away from the anvil. The plurality of anvil-side cord supports and the plurality of cartridge-side cord supports may have an open tubular structure with a substantially C-shaped cross-sectional shape, where the opening of the C may be facing away from the cartridge on the plurality of anvil-side cord supports and the opening of the C may be facing away from the anvil on the plurality of cartridge-side cord supports.

The plurality of anvil-side cord supports and the plurality of cartridge-side cord supports may have a hollow tubular structure and wherein the end effector may include a buttress material, the buttress material having a plurality of openings with a cord slidably positioned within the plurality of openings. In a preponderance of the plurality of openings of the buttress material, the cord may be slidably positioned within at least one of the plurality of anvil-side cord supports and the plurality of cartridge-side cord supports. The plurality of cartridge-side cord supports may be mounted to the cartridge frame. The buttress material may include an adhesive that removably adheres the buttress material to one of the anvil face and the cartridge face.

In still a further embodiment, a method of using a buttress material with an end effector includes the steps of: providing an end effector having an anvil that includes a first end, a second end, and an anvil face, a cartridge housing a plurality of staples and that includes a first end, a second end, and a cartridge face, and a rigid link that movably couples the first end of the anvil to the first end of the cartridge, wherein the second end of the anvil is movably coupled to the second end of the cartridge; providing a buttress material; moving the rigid link to open the anvil face away from the cartridge face; attaching the buttress material to at least one of the anvil face and the cartridge face; moving the rigid link to close the anvil face towards the cartridge after attaching the buttress material; driving the plurality of staples from the cartridge, through the buttress material, and towards the anvil to form the staples; moving the rigid link to open the anvil face away from the cartridge face after driving the staples; and removing the buttress material from the end effector. The buttress material may be formed from a bioabsorbable material. The buttress material may be attached to at least one of the anvil face and the cartridge face using an adhesive. The anvil may include a plurality of anvil-side cord supports arranged from about the first end to about the second end, the cartridge including a plurality of cartridge-side cord supports arranged from about the first end to about the second end, and the buttress material including a plurality of openings, with a cord slidably positioned within the plurality of openings. The method may further include one or more of the steps of: sliding the cord from the buttress material into a preponderance of the cord supports when attaching the buttress material to at least one of the anvil face and the cartridge face, and sliding the cord from the buttress material out of the preponderance of the cord supports when removing the buttress material from the end effector; tensioning the cord to align the buttress material with the end effector; and pulling the cord to disengage the buttress material from the end effector by sliding the cord out of the plurality of cord supports and out of the plurality of openings of the buttress material.

In another embodiment, a device is disclosed that includes a first jaw having an anvil that includes a first end, a second end, and an anvil face, the anvil having a plurality of anvil-side cord supports; a second jaw having a cartridge housing a plurality of staples and that includes a first end, a second end, and a cartridge face, the cartridge having a plurality of cartridge-side cord supports; a first coupling that couples the first end of the first jaw to the first end of the second jaw; and a second coupling that movably couples the second end of the first jaw to the second end of the second jaw, wherein the second coupling includes a rigid link that is movably coupled to the first and second jaws. An outer tube may extend from the first jaw and the second jaw to an actuator, wherein the actuator moves the outer tube from a first position to a second position, wherein the first position of the tube allows the rigid link to maintain the jaws in an open position, and the second position of the tube moves the rigid link to move the first jaw towards the second jaw. The second jaw may have a longitudinal axis, wherein the first coupling includes a pin that rotatably couples the first jaw to the second jaw, wherein the rotation about the pin is transverse to the longitudinal axis. The pin that rotatably couples the first jaw to the second jaw may be slidably received within a slot in at least one of the first jaw or the second jaw. In one embodiment at least one of the first jaw or the second jaw slidably receives the rigid link within a slot as the first jaw is moved toward the second jaw. The rigid link may be coupled to the first jaw using a slot that allows motion of the rigid link in a first direction but limits motion of the rigid link in a direction perpendicular to the first direction.

In another embodiment, an end effector useful to staple an anatomical structure is disclosed, the anatomical structure having a first side and a second side. The end effector includes: an anvil that includes a first end, a second end, and an anvil face that may be positionable on the first side of the anatomical structure, the anvil face including a plurality of rows of staple forming pockets, where a first row of the plurality of rows of staple forming pockets has a first pocket depth and the second row of the plurality of rows of staple forming pockets has a second pocket depth, where the first pocket depth is different from the second pocket depth; a cartridge housing a plurality of staples and that includes a first end, a second end, and a cartridge face that may be positionable on the second side of the anatomical structure; and a staple driver ramp and tissue cutting assembly having a staple driver ramp that moves from the first end of the cartridge to the second end of the cartridge and drives staples from the cartridge towards the anvil to form the staples, the staple driver ramp and tissue cutting assembly further including a blade that cuts the anatomical structure after the staples have been formed with at least a portion of one of the anvil and the cartridge being movable toward the other to clamp the end effector on the anatomical structure.

The cartridge face may include a channel extending from about the second end to about the first end, the channel defining the path of a cutting blade, wherein the pocket depth of the first row of the plurality of rows of staple forming pockets has a first pocket depth that is shallower than the pocket depth of the second row of the plurality of rows, wherein the first row of the plurality of rows of staple forming pockets is closer to the slot than the second row of the plurality of rows of staple forming pockets. The anvil may have an anvil length extending from about the first end of the anvil to about the second end of the anvil, the plurality of rows of the plurality of staple forming pockets extending along the anvil length, wherein in at least one row of the plurality of rows of the plurality of staple forming pockets, a first pocket depth at a first location along the length is different from a second pocket depth at a second location along the length. The anvil may include at least 3 rows of the plurality of staple forming pockets, each one of the at least three rows having the plurality of pocket depths different from the other two of the at least three rows. For example, the row of staple forming pockets closest to the channel may be shallower than row of staple forming pockets farthest from the channel. In one embodiment, the rows of staple forming pockets are substantially circular.

The plurality of staples in a first row of the plurality of rows of staples may be manufactured from a first material and the plurality of staples in a second row of the plurality of rows of staples may be manufactured from a second material, wherein the first material is different from the second material. The anvil has an anvil length extending from about the first end of the anvil to about the second end of the anvil, wherein in at least one row of the plurality of rows of the plurality of staple forming pockets, a first pocket depth at a first location along the length is different from a second pocket depth at a second location along the length. The pocket depth may vary continuously along the anvil length. In one embodiment, in at least one row of the plurality of rows of staple forming pockets, the pocket depth has a first depth for a first portion of the length of the row and a second depth for a second portion of the length of the row. In another embodiment, in at least one row of the plurality of rows of staple forming pockets the pocket depth has a first depth for a first portion of the length of the row and a second depth, deeper than the first depth, for a second portion of the length of the row adjacent the first portion of the length of the row and a third depth for a third portion of the length of the row, shallower than the second depth, the third portion of the length of the row adjacent the second portion of the length of the row. The rows of staple forming pockets may be substantially circular such as for use in a circular stapler useful for bowel resection, may be linear for a linear cutter, or may be another desired shape. In at least one row of the plurality of rows of staple forming pockets in one embodiment, the pocket depth variation along the length of a first row of the plurality of rows varies in pocket depth at a different scale or rate than a second row of the plurality of rows.

In another embodiment, an end effector is disclosed for stapling an anatomical structure, the anatomical structure having a first side and a second side. The end effector includes: an anvil that includes a first end, a second end, and an anvil face that may be positionable on the first side of the anatomical structure, the anvil face including a plurality of rows of staple forming pockets, wherein a first row of the plurality of rows of staple forming pockets has a first pocket depth and the second row of the plurality of rows of staple forming pockets has a second pocket depth, wherein the first pocket depth is different from the second pocket depth; a cartridge housing a plurality of staples and that includes a first end, a second end, and a cartridge face that may be positionable on the second side of the anatomical structure; and a staple driver ramp and tissue cutting assembly, wherein the staple driver ramp moves from the first end of the cartridge to the second end of the cartridge and drives staples from the cartridge towards the anvil to form the staples, the staple driver ramp and tissue cutting assembly further including a blade that cuts the anatomical structure after the staples have been formed, with at least a portion of one of the anvil and the cartridge being movable toward the other to clamp the end effector on the anatomical structure, wherein a first row of the plurality of rows of staple forming pockets has a first pocket shape and the second row of the plurality of rows of staple forming pockets has a second pocket shape, wherein the first pocket shape is different from the second pocket shape. The first row of the plurality of rows of staple forming pockets may produce bow-tie shaped staples and the second row of the plurality of rows of staple forming pockets may produce rectangular shaped staples after forming, in one example. A first row of the plurality of rows of staples may be manufactured from a first material and the plurality of staples in a second row of the plurality of rows of staples may be manufactured from a second material, wherein the first material is different from the second material in another example. For example, the first material may contain greater than 95% by weight of Titanium and the second material may be an alloy of less than 95% by weight of titanium alloyed with aluminum. In another example, the first material may contain greater than 96% by weight of titanium and the second material may be an alloy of less than 96% by weight of titanium alloyed with aluminum and vanadium. In another example, the plurality of staples in a first location along the length may be manufactured from a material greater than 95% by weight of titanium and the plurality of staples in a second location along the length may be manufactured from an alloy of less than 95% by weight titanium alloyed with aluminum. In another embodiment, the row of the plurality of staples closer to the channel has staples with less springback than the row of the plurality of staples further from the channel.

In another exemplary embodiment, an anvil that includes a first end, a second end, and an anvil face that may be positionable on the first side of an anatomical structure. A cartridge housing a plurality of staples and that includes a first end, a second end, a cartridge length extending from about the first end of the cartridge to about the second end of the cartridge, and a cartridge face that may be positionable on the second side of the anatomical structure. The cartridge may include a plurality of rows of a plurality of staples, wherein the plurality of staples in a first portion of a first row of the plurality of rows of staples may be manufactured from a first material and the plurality of staples in a second portion of the first row of the plurality of rows of staples may be manufactured from a second material, wherein the first material is different from the second material. A staple driver ramp and tissue cutting assembly may have a staple driver ramp that moves from the first end of the cartridge to the second end of the cartridge and drives staples from the cartridge towards the anvil to form the staples. The staple driver ramp and tissue cutting assembly may further include a blade that cuts the anatomical structure after the staples have been formed, with at least a portion of one of the anvil and the cartridge being movable toward the other to clamp the end effector on the anatomical structure. The first material may contain greater than 96% by weight of titanium, for example, and the second material may be an alloy of less than 96% by weight of titanium alloyed with aluminum and vanadium.

In another embodiment, an end effector is disclosed that is useful to staple an anatomical structure during a surgical procedure, the anatomical structure having a first side and a second side. The end effector includes an anvil that has a first end, a second end, and an anvil face that may be positionable on the first side of the anatomical structure, the anvil face including a plurality of rows of staple forming pockets, wherein a first row of the plurality of rows of staple forming pockets has a first pocket shape and a second row of the plurality of rows of staple forming pockets has a second pocket shape, wherein the first pocket shape is different from the second pocket shape. A cartridge housing a plurality of staples and that includes a first end, a second end, and a cartridge face that may be positionable on the second side of the anatomical structure is also disclosed. A staple driver ramp and tissue cutting assembly is disclosed as having a staple driver ramp that moves from the first end of the cartridge to the second end of the cartridge and drives staples from the cartridge towards the anvil to form the staples, the staple driver ramp and tissue cutting assembly further including a blade that cuts the anatomical structure after the staples have been formed, with at least a portion of one of the anvil and the cartridge being movable toward the other to clamp the end effector on the anatomical structure. The first row of the plurality of rows of staple forming pockets may produce bow-tie shaped staples after forming and the second row of the plurality of rows of staple forming pockets may produce rectangular shaped staples after forming, for example. In at least one row of the plurality of rows of the plurality of staple forming pockets, a first pocket shape at a first location along the length is different from a second pocket shape at a second location along the length in another example. A first row of the plurality of rows of staple forming pockets may produce bow-tie shaped staples after forming and a second row of the plurality of rows of staple forming pockets may produce rectangular shaped staples after forming in another example. Also, the plurality of staples in a first portion of the first row of the plurality of rows of staples may be manufactured from a first material and the plurality of staples in a second portion of the first row of the plurality of rows of staples may be manufactured from a second material, wherein the first material is different from the second material.

BRIEF DESCRIPTION OF THE DRAWINGS

The present disclosure will be more readily understood from a detailed description of some sample embodiments taken in conjunction with the following figures:

FIG. 14A depicts a side view of the stapling device of FIG. 11 shown in an open position;

FIG. 14B depicts a side view of the stapling device of FIG. 11 shown in a closed position;

FIG. 15 depicts a side cross-sectional view, taken along section D-D, of the handle portion and the motor shown in FIG. 14A;

FIG. 16 depicts a side view of the end effector shown in FIG. 14A;

FIG. 26A is a side cross-sectional view of an end effector for a stapling device, including an anvil assembly and a cartridge assembly, having a plurality of staple drivers having variable heights combined with a plurality of staples having variable heights according to one embodiment;

FIG. 26B is a side cross-sectional view of an end effector for a stapling device, including an anvil assembly and a cartridge assembly, having a plurality of staple drivers having variable heights combined with a plurality of staples having variable heights according to an alternate embodiment;

FIG. 26C is a cross-sectional view of an end effector for a stapling device, including an anvil assembly and a cartridge assembly, having a plurality of staple drivers with a first height associated with a plurality of staples having a first height and a plurality of drivers having a second height associated with a plurality of staples having a second height according to one embodiment;

FIG. 26D is a cross-sectional view of an end effector for a stapling device, including an anvil assembly and a cartridge assembly, having a plurality of staple drivers having a uniform height combined with a plurality of staples having variable heights according to one embodiment;

FIG. 26E is a cross-sectional view of an end effector for a stapling device, including an anvil assembly having an angled anvil plate and a cartridge assembly, the stapling device having a plurality of staple drivers with a uniform height and a plurality of staples having a uniform height;

FIG. 33A is a side view of the stapling device of FIG. 31 shown in an open position;

FIG. 33B is a side view of the stapling device of FIG. 31 shown in a closed position;

FIG. 34A is a top view of the buttress shown in FIG. 32;

FIG. 34B is a partial perspective view of the buttress shown in FIG. 32;

FIG. 35A depicts a bottom plan view of an anvil assembly of the end effector shown in FIG. 31;

FIG. 35B depicts a bottom plan view of the anvil assembly, shown in FIG. 31, with the buttress of FIG. 32 attached, according to one embodiment;

FIG. 37 depicts a partial exploded perspective view of a stapling device, shown in an open position, having an end effector, an elongated tube, a handle portion, and an adhesive-type buttress in accordance with one embodiment;

FIG. 38C is a front view of the adhesive-type buttress shown in FIG. 38B;

FIG. 38D depicts a side view of the end-effector of FIG. 37 shown with the adhesive-type buttress attached to the end effector according to one embodiment;

DETAILED DESCRIPTION

Figure 1:
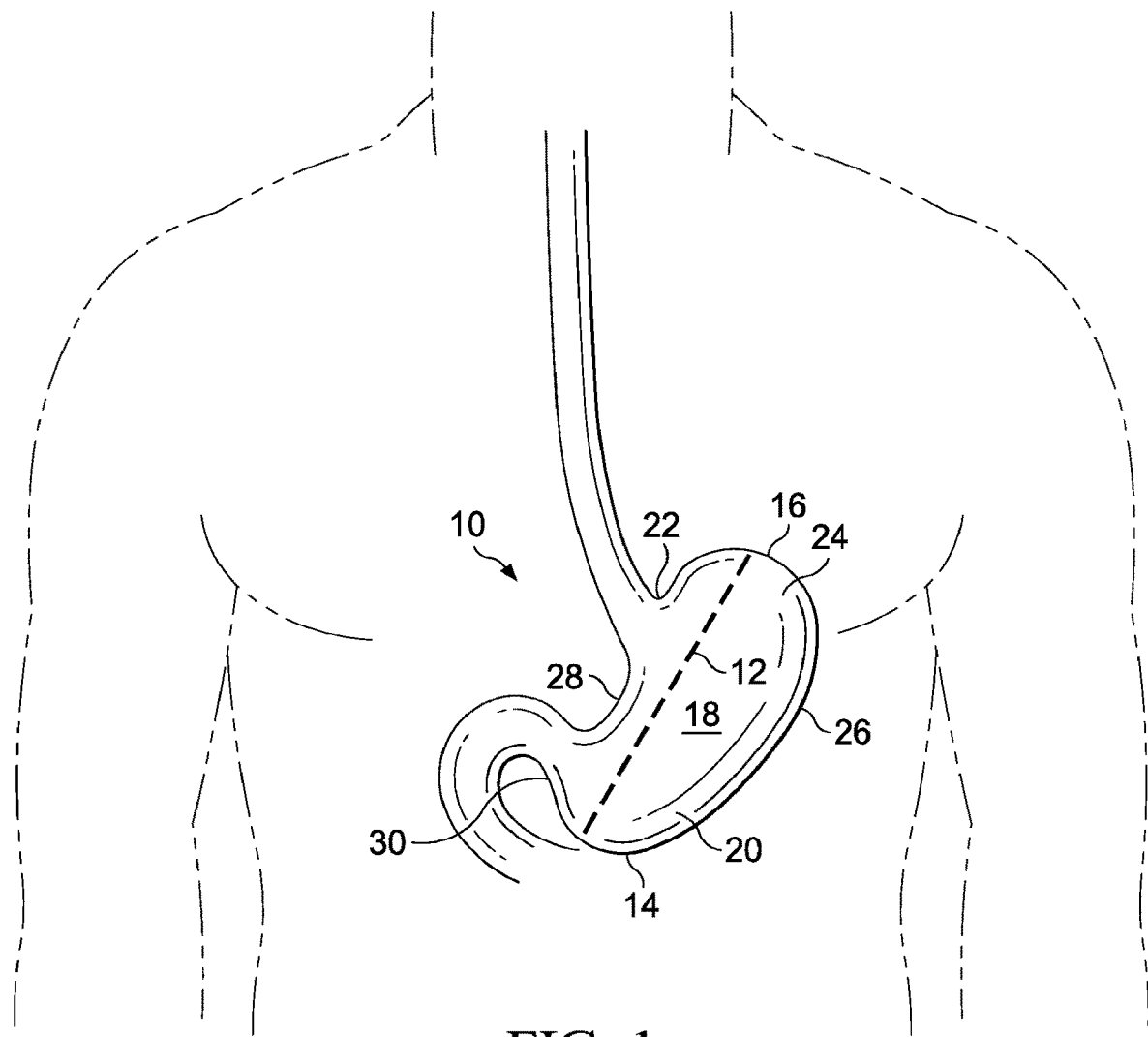
FIG. 1 depicts the anatomy of a stomach.

Various non-limiting embodiments of the present disclosure will now be described to provide an overall understanding of the principles of the structure, function, and use of the apparatuses, systems, methods, and processes disclosed herein. One or more examples of these non-limiting embodiments are illustrated in the accompanying drawings. Those of ordinary skill in the art will understand that systems and methods specifically described herein and illustrated in the accompanying drawings are non-limiting embodiments. The features illustrated or described in connection with one non-limiting embodiment may be combined with the features of other non-limiting embodiments. Such modifications and variations are intended to be included within the scope of the present disclosure. Reference throughout the specification to "various embodiments," "some embodiments," "one embodiment," "some example embodiments," "one example embodiment," or "an embodiment" means that a particular feature, structure, or characteristic described in connection with any embodiment is included in at least one embodiment. Thus, appearances of the phrases "in various embodiments," "in some embodiments," "in one embodiment," "some example embodiments," "one example embodiment, or "in an embodiment" in places throughout the specification are not necessarily all referring to the same embodiment. Furthermore, the particular features, structures or characteristics may be combined in any suitable manner in one or more embodiments. Described herein are example embodiments of apparatuses, systems, and methods for surgical staplers. In one example embodiment, an end effector and/or an endocutter stapling device (collectively referred to as "devices" herein) is disclosed for forming a resection line during resection of an organ, tissue, or other anatomical structure. In some embodiments, the devices may be used during minimally invasive surgical procedures. This application is related to U.S. patent application Ser. No. 15/129,385, which is hereby incorporated herein by reference in its entirety.

Surgical staplers in accordance with embodiments described herein can include a handle, an actuator, and an end effector including a clamping mechanism. The clamping mechanism can include a cartridge and an anvil. During operation, the surgeon can clamp two members (e.g., the anvil and the cartridge) on the organ and compress the organ therebetween. Once the organ has been compressed, the surgeon can use the stapler to drive or fire staples through the organ. In one embodiment, with desirable compression and alignment of the clamping mechanism, a plurality of B-shaped staples can be formed. In some embodiments, the stapling device can be fired multiple times using multiple cartridges, or in an alternate embodiment a single cartridge can be used with a single firing to complete resection of an organ. It may be advantageous to reduce the number of firings and cartridges required as the expense of a procedure can increase with the use of cartridges and with a longer procedure that can be associated with multiple stapler firings. It may also be advantageous to provide for single cartridge stapling and/or resection of an organ to reduce the time a patient is in surgery, which can improve clinical outcomes. For example, resecting a portion of the stomach in accordance with a sleeve gastrectomy procedure using a single cartridge and stapler firing may improve patient outcomes and reduce complications that can be associated with such procedures.

The integrity of a staple line can depend, in part, on the proper formation of B-shaped staples when such a staple configuration is desirable. Providing a single cartridge and single firing stapling device may improve the quality of staple formation over a device or system using multiple cartridges to complete the same procedure. For example, when using an end effector multiple times to staple and resect tissue the previously deployed staples may be contacted by the new staples and/or cutting knife in subsequent applications. Providing a single cartridge and staple firing may help insure that the staple line, and shape of the staples, is consistent.

A single cartridge and single firing stapling device may also provide compression benefits relative to a device and system requiring the use of multiple cartridges. It may be advantageous to provide a single firing stapling device that provide for desirable compression along the length of the tissue to be resected while also providing for a single staple line with properly formed staples. A B-shaped staple is the standard of care for gastrointestinal, vascular, pulmonary, and hepatic applications of surgical tissue fastening devices. Alignment in each of the X, Y, and Z axes of the clamping mechanism with itself (e.g., alignment of the anvil with the cartridge) on each side of the organ may improve staple delivery and formation. It will be appreciated that any suitable structure or mechanism may be incorporated into the stapling devices described herein to provide for such alignment.

Embodiments of stapling devices described herein may include multiple rows of staples such that there is less chance of leaking of lumenal contents between each of the staples and the staple rows. For example, a stapling device may have from two to six rows of staples, where the staple rows can be bisected by a knife or blade configured to pass between the rows to resect stapled tissue. In one embodiment, the staple rows can be spaced apart and/or staggered to reduce the likelihood of leakage.

Embodiments of stapling devices can include an anvil and a cartridge, where the cartridge can include recesses retaining a plurality of staples. The staples can be retained above one or more staple drivers that, during operation, can urge each of the plurality of staples upward through tissue into the face of the anvil. The anvil, which can include pockets having any suitable size, number, and dimensions, can cooperate with the cartridge drivers to form, for example, a B-shape within tissue. The pockets of the anvil, in one embodiment, can be sized to provide a desirable closed staple height that can be determined by the gap between the anvil and cartridge, the depth of the pocket and the height of the staple, and/or the staple driver and the driver mechanism.

During stapling, it may be advantageous to provide a support or buttress material through which the staples can be deployed. The buttress or support material may help distribute the pressure of multiple rows of staples, to improve the purchase of the staples in tissue, or to maintain the integrity of a staple line. For example, a biodegradable material can be provided on the faces of the anvil and/or cartridge through which the staples can be deployed during use. This buttress material, retaining the staples, can then be cut by a blade or knife and, in one embodiment, can be left within a patient. Any suitable support or buttress material, such as those composed of polymers (both permanent and bioabsorbable) as well as biologic films can be used in accordance with embodiments described herein. These materials can be reversibly coupled to the anvil, the cartridge, or both.

Methods of attaching the buttress or support material to the anvil or cartridge can include adhesives, such as hydrogel polymers, where the buttress can be pulled away from the end effector after it has been secured with staples to tissue. The end effector may also include mechanical structures or elements to retain the buttress, such as projections or the like. In one embodiment, the anvil and/or cartridge can include a plurality of spaced apart projections, the buttress material can define a plurality of apertures, and a cord or suture can be used to threadedly secure the buttress material with the projections of the anvil and/or cartridge.

Embodiments of stapling devices described herein, in accordance with a laparoscopic approach, can include inserting the end effector of the stapler through a trocar to perform the surgical procedure. By way of example, minimally invasive surgical procedures may include a laparoscopic vertical sleeve gastrectomy. Because the spatial environment for such procedures is limited, surgical stapling devices in accordance with embodiments described herein may have a relative low profile. Minimally invasive devices in the prior art are generally long (e.g., 35 mm to 60 mm) and thin (e.g., 5 mm to 15 mm diameter) devices. This long and thin configuration may be necessary to fit through the trocar into the body cavity. The limited size can present a mechanical issue as B-shaped staple formation typically requires a pressure of about 100 psi. Under these pressures, small, less rigid, staplers may deform and thus prevent proper B-shaped staple formation.

Prior art devices used in minimally invasive surgical procedures often have a fixed hinge at a proximal end. This hinge allows the anvil and cartridge to separate into a V-shaped configuration. Once separated, the surgeon may place the open anvil and cartridge around the organ and then collapse the V onto the organ. However, as the length of the anvil and cartridge increase, it may be more difficult to maintain alignment between the anvil and cartridge across the length of the tissue. Poor alignment with such designs can be exacerbated at the most distant ends of such devices can be deflected because of the forces necessary to compress the tissue. Because of this deflection, the length of current V-shaped staplers for minimally invasive procedures is limited. As a result of this limitation, the anvil and the cartridge are correspondingly limited in length. This limitation on length requires, for larger organs like the stomach, multiple staple reloads and firings to complete a procedure such as a sleeve gastrectomy. Each reload may require the surgeon to withdraw the stapler from the trocar, reload the cartridge, reinsert, and then reposition the stapler on the organ. Such systems may require more surgical time, may be more costly, may have an increased likelihood of resulting in an adverse patient event, and may result in a staple line having less integrity.

The examples discussed herein are examples only and are provided to assist in the explanation of the apparatuses, devices, systems and methods described herein. None of the features or components shown in the drawings or discussed below should be taken as mandatory for any specific implementation of any of these the apparatuses, devices, systems or methods unless specifically designated as mandatory. For ease of reading and clarity, certain components, modules, or methods may be described solely in connection with a specific figure. Any failure to specifically describe a combination or sub-combination of components should not be understood as an indication that any combination or sub-combination is not possible. Also, for any methods described, regardless of whether the method is described in conjunction with a flow diagram, it should be understood that unless otherwise specified or required by context, any explicit or implicit ordering of steps performed in the execution of a method does not imply that those steps must be performed in the order presented but instead may be performed in a different order or in parallel.

Example embodiments described herein can be used, for example, in a sleeve gastrectomy procedure or resection of the stomach. It will be appreciated, however, that the devices may be used in other procedures involving other anatomical structures. For example, the devices may be used in a parencymal resection, lung volume reduction surgery, or other procedures involving the lung. Further, embodiments described herein may be useful in an anatomic resection, such as, a lobectomy, a non-anatomic parencymal resection, or other procedures involving the liver, or in a partial nephrectomy, total nephrectomy, or other procedures involving the kidney.

Referring now to FIG. 1, shown are the anatomy of the stomach 10 and an example resection line 12 for a vertical sleeve gastrectomy. The stomach 10 generally includes an inferior end 14, a superior end 16, an anterior side 18, and a posterior side 20. A gastroesophageal junction 22 opens into the stomach 10 and is a common landmark in bariatric surgeries. A fundus 24 and the section of the stomach 10 defined by a greater curvature 26 are generally the parts of the stomach 10 removed during a vertical sleeve gastrectomy. The remaining pouch or sleeve may be generally defined by a lesser curvature 28 and the resection line 12, which presents a stomach with a significantly reduced volume. The desired location of the resection line 12 may be about 0.5 cm to about 2 cm away from the gastroesophageal junction 22 and about 2 cm to about 10 cm away from a pylorus 30. In accordance with embodiments described herein, endocutter stapling devices may be utilized to form high quality, consistent resection lines during a vertical sleeve gastrectomy. Embodiments of the devices may be advantageous because they may be easily positionable laparoscopically, can accommodate different thicknesses of tissue along the resection line length, can be capable of providing uniform compressive pressure on the tissue along the resection line, and can enable a low staple firing force.

Figure 2A:
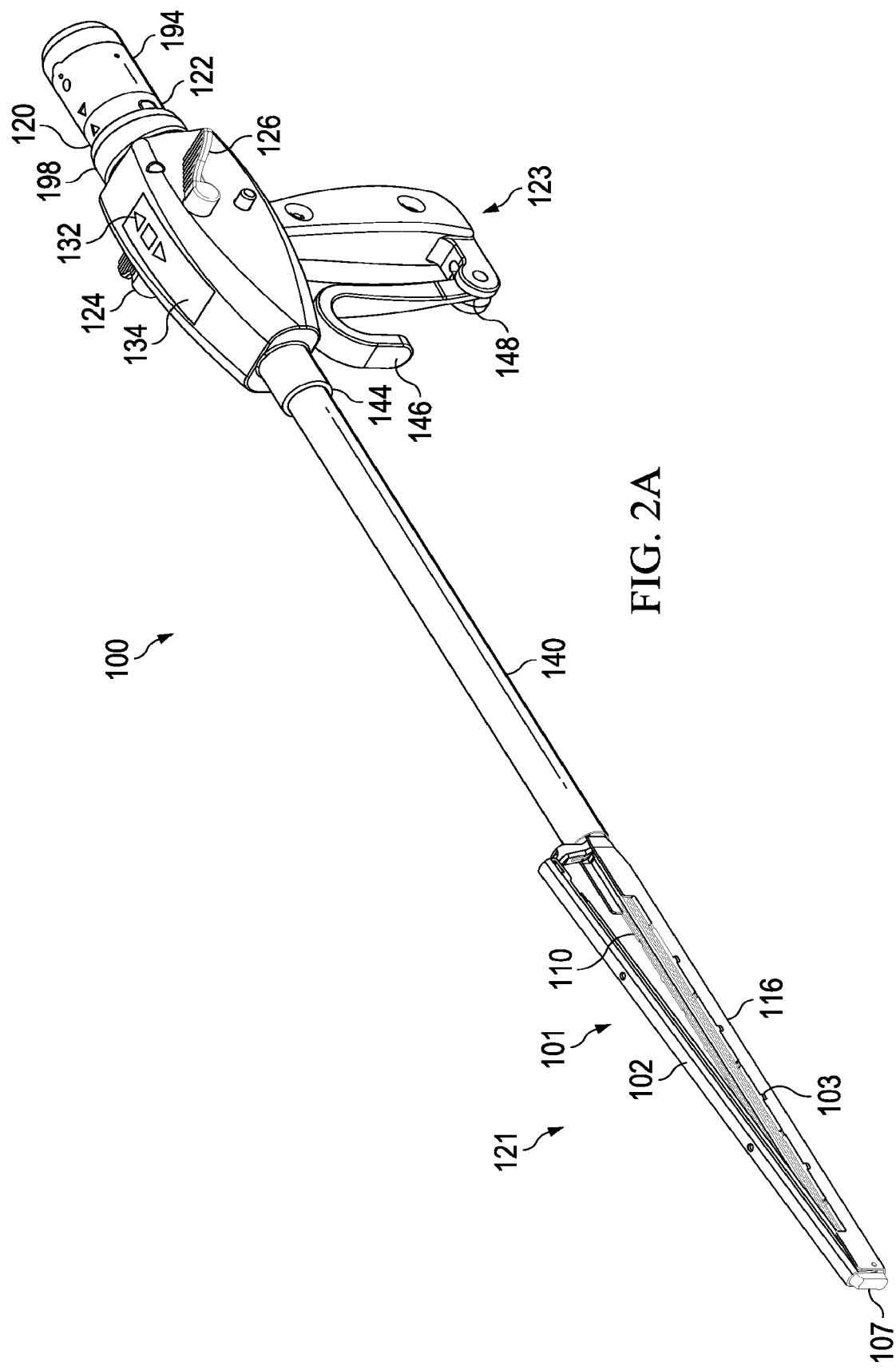
FIG. 2A depicts a perspective view of a stapling device, shown in an open position, having an end effector, an elongated tube, and a handle portion in accordance with one embodiment.
Figure 2B:
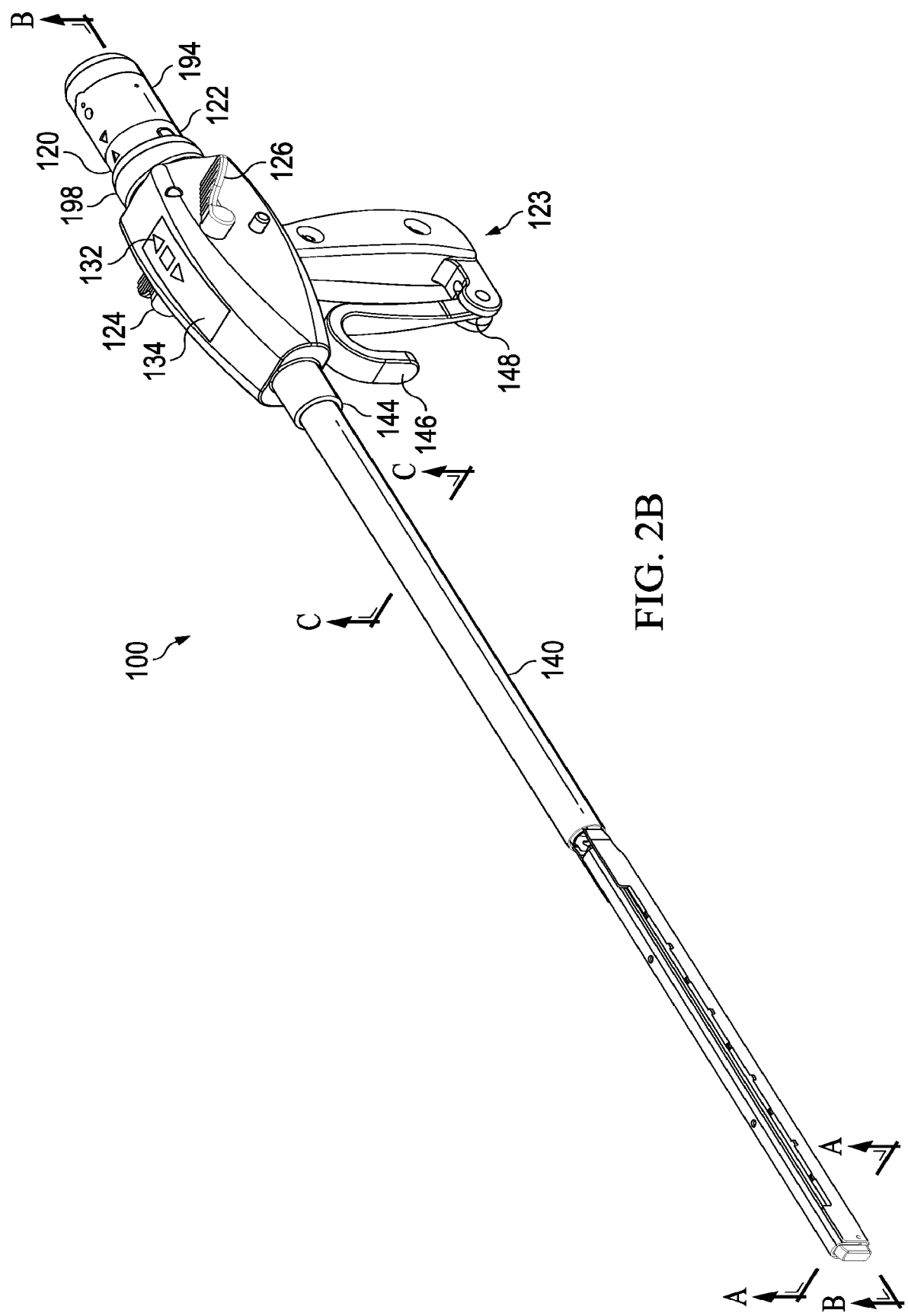
FIG. 2B depicts a perspective view of the stapling device of FIG. 2A, shown in a closed position, in accordance with one embodiment.

FIG. 2A depicts a perspective view of a stapling device 100 including an end effector 121, a support tube 140, and a handle portion 123, shown in an open position. FIG. 2B depicts a perspective view of the stapling device 100 shown in a closed position.

Figure 3A:
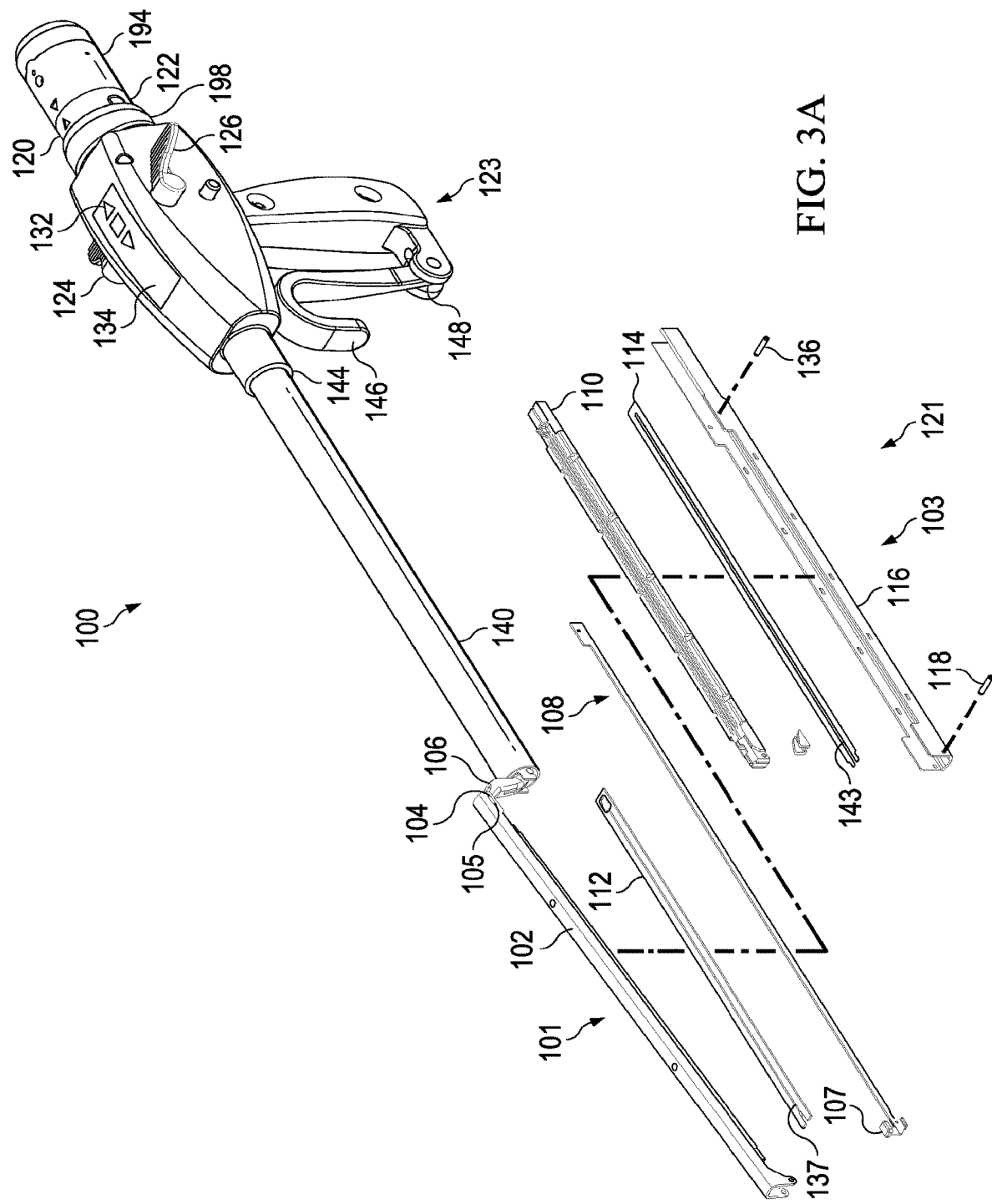
FIG. 3A is a partially exploded perspective view of the stapling device shown in FIGS. 2A and 2B.
Figure 3B:
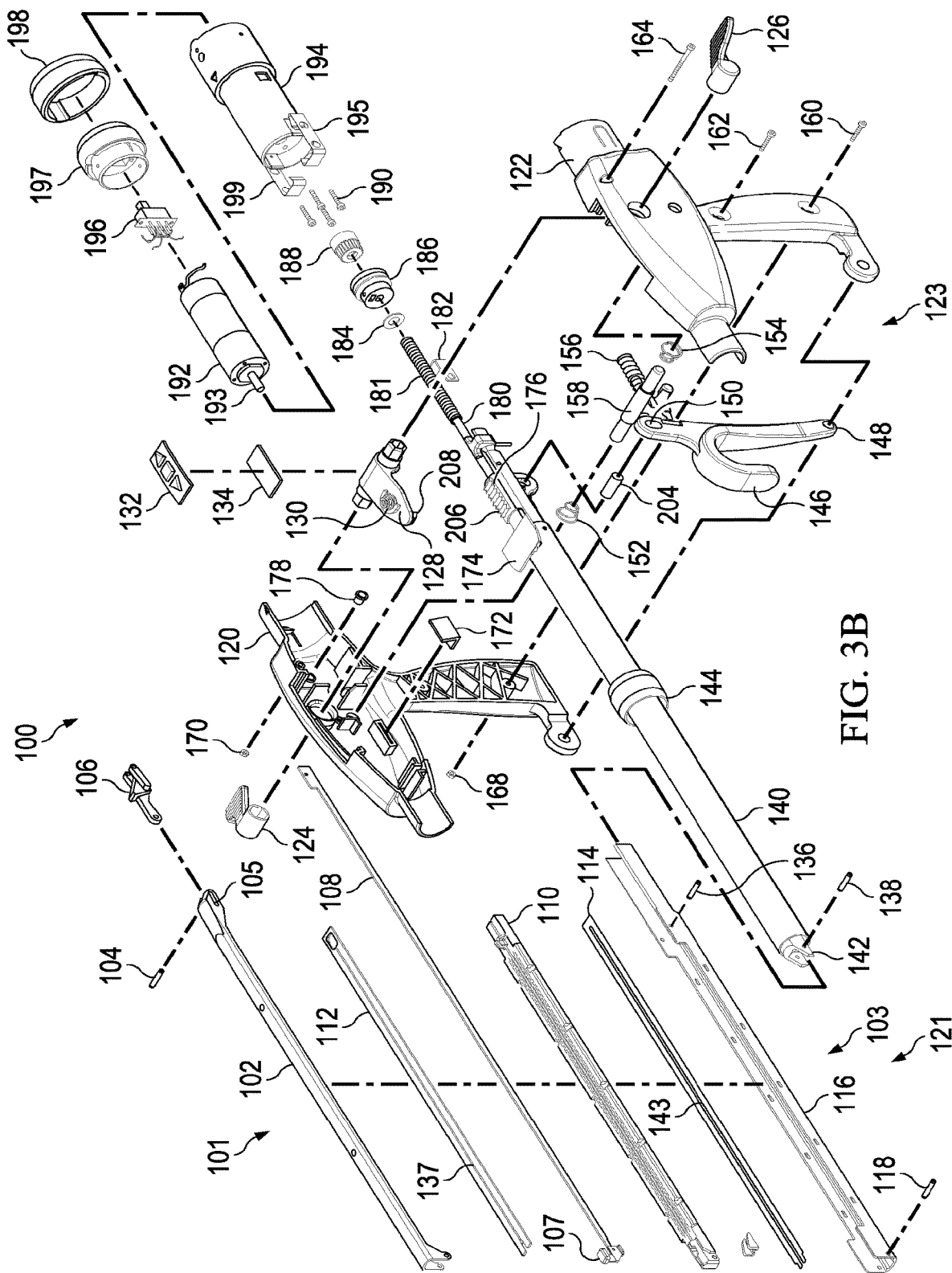
FIG. 3B is an exploded perspective view of the stapling device shown in FIGS. 2A and 2B.
Figure 4:
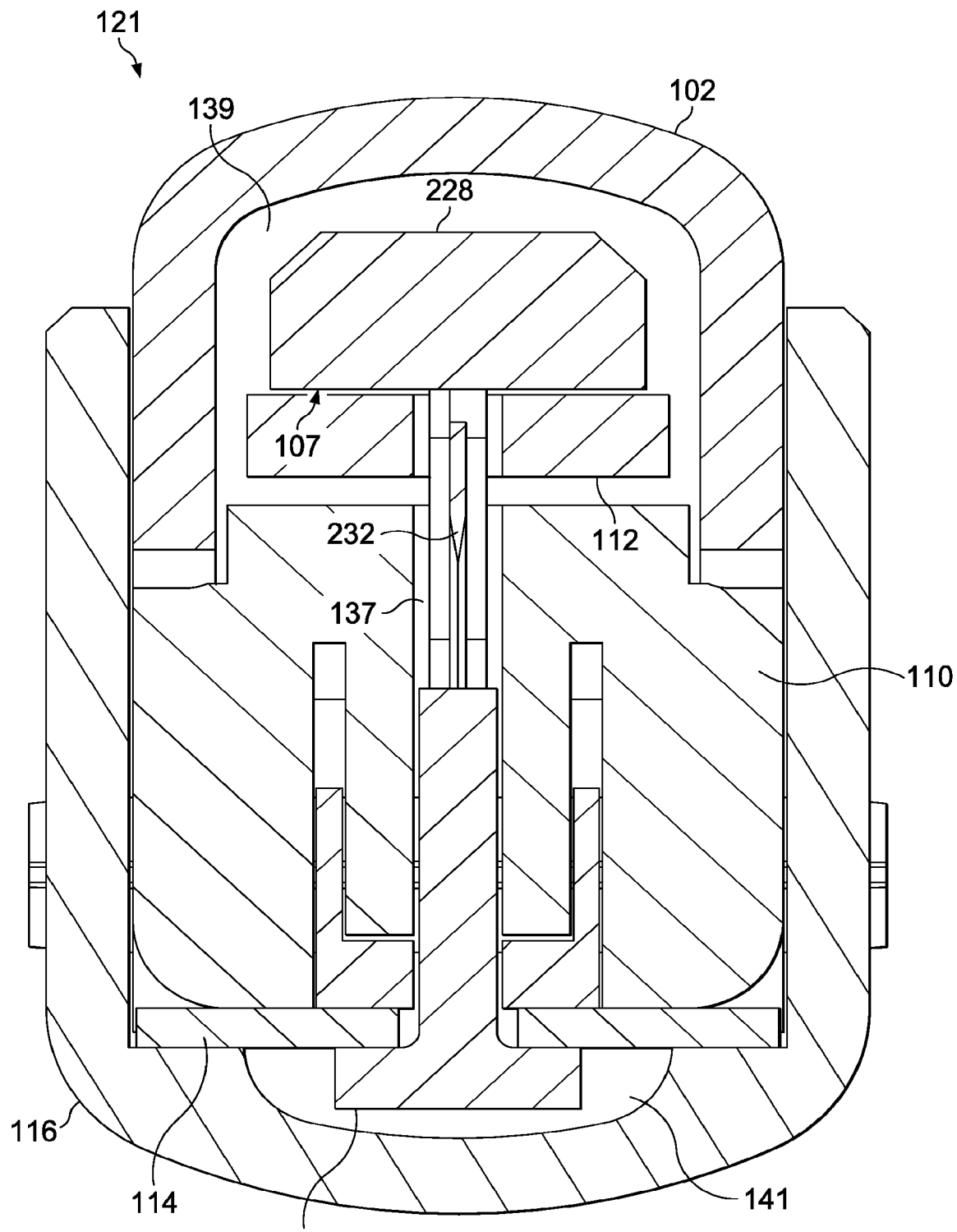
FIG. 4 depicts an axial cross-sectional view of the end effector shown in FIG. 2B, taken along section A-A, showing the relationship between a blade, an anvil assembly, and a cartridge assembly of the end effector.

FIGS. 3A and 3B depict an exploded perspective view of the stapling device 100 illustrated in accordance with at least one embodiment. The end effector 121 of the stapling device 100 can include an anvil assembly 101 and a cartridge assembly 103. The anvil assembly 101 can include an anvil frame 102 and an anvil plate 112. The anvil plate 112 may be welded to the anvil frame 102, or may be otherwise attached to the anvil frame 102 or end effector 121 such as by gluing, brazing, sintering, machining, 3D printing or the like. The anvil assembly 101 can include a longitudinal axis along which the anvil frame 102 and the anvil plate 112 are oriented. The anvil plate 112 can define an anvil plate channel 137 aligned with the longitudinal axis that can be sized to receive a blade 107 associated with a blade assembly 108. As illustrated in FIG. 4, the anvil frame 102 and the anvil plate 112 can cooperate to define an anvil blade channel 139 that can be sized to accept a top portion 228 of the blade 107. During operation, the anvil blade channel 139 can guide the blade 107 as it moves, for example, from a distal first position to a proximal second position within the anvil plate channel 137. In an alternate embodiment, the blade 107 can transition from a proximal first position to a distal second position. Because the distal end of the end effector 121 is coupled in certain embodiments, rather than open, it permits the ability to initially position the blade 107 at the distal end of the end effector prior to use or cutting. Such a position may be advantageous because the blade 107 associated with the blade assembly 108 can be pulled, rather than pushed, to prevent buckling. Providing a blade assembly 108 with an elongate beam 226 (FIG. 6) may be beneficial because, as the beam 226 is within the channels of the anvil and the cartridge it can prevent the cartridge from deflecting into the cavity of the channel. Such deflection into the channel may cause staples to be malformed. I-beam portions of the blade may correct for the deflection of the anvil and cartridge structural members that can happen during loading to enable the proper gap for staple formation to be achieved.

Referring to FIGS. 3A and 3B, the anvil plate 112 can be, for example, from 20 cm to 26 cm in length, from 10 cm to 30 cm in length, from 5 cm to 32 cm in length, from 21 cm to 24 cm in length, or any other suitable length. In one embodiment, the length of the anvil plate 112 is sized such that it can traverse the length of an organ, such as the stomach, for use in a sleeve gastrectomy procedure. For example, the anvil plate 112 can be 23 cm in length such that it can be used in combination with the cartridge assembly 103 to provide a staple line in accordance with a single firing, single cartridge sleeve gastrectomy procedure.

The cartridge assembly 103 can include a cartridge frame 116 that can retain a cartridge plate 114 and a cartridge 110. The cartridge plate 114 may be welded to the cartridge frame 116, or may be otherwise attached to the cartridge frame 116 or end effector 121 such as by gluing, brazing, sintering, machining, 3D printing or the like. The cartridge assembly 103 can include a longitudinal axis along which the cartridge frame 116 and cartridge plate 114 can be oriented. The cartridge plate 114 can define a cartridge channel 143 aligned with the longitudinal axis that can be sized to receive the blade 107 associated with the blade assembly 108. As illustrated in FIG. 4, the cartridge frame 116 and the cartridge plate 114 can cooperate to define a cartridge blade channel 141 that can be sized to accept a bottom portion 230 of the blade 107. During operation, the cartridge blade channel 141 can guide the blade 107 as it moves, for example, from a distal first position to a proximal second position within the cartridge channel 143. In an alternate embodiment, the blade 107 can transition from a proximal first position to a distal second position. In alternate embodiment, the cartridge blade channel 141, or associated channels, can be curvilinear or have any other suitable configuration.

Referring to FIGS. 3A and 3B, the cartridge 110 can be attached to the cartridge frame 116 by a first cartridge pin 136 at a first end and a second cartridge pin 118 at a second end or, alternately, the cartridge 110 can be attached to the cartridge frame 116 via snap fit, gluing, or other attachment methods. The cartridge 110 can be, for example, from 20 cm to 26 cm in length, from 10 cm to 30 cm in length, from 5 cm to 32 cm in length, from 21 cm to 24 cm in length, or any other suitable length. In one embodiment, the length of the cartridge 110 is sized such that it can traverse the length of an organ, such as the stomach, for use in a sleeve gastrectomy procedure. For example, the cartridge 110 can be 23 cm in length such that it can be used in combination with the anvil assembly 101 to provide a staple line in accordance with a single firing, single cartridge sleeve gastrectomy procedure.

The end effector 121 can include a master link 106 that can be used to transition the end effector 121 from a closed position (see, for example, FIG. 2B), to an open position (FIG. 2A), back to a closed position. The master link 106 can be attached to a first end of the anvil frame 102, which may be a proximal end of the anvil frame 102, by a first master link pin 104 such that the first master link pin 104 pivotally and slidably engages a master link slot 105 defined by the anvil frame 102. The master link slot 105 can be a channel parallel to the longitudinal axis of the anvil frame 102, or the master link slot 105 can be angled up or down, or otherwise offset relative to the longitudinal axis of the anvil frame. In certain embodiments, the master link slot 105 can be angled or offset to achieve more (angled away from) or less (angled toward) gap between the anvil assembly 101 and the cartridge assembly 103. In certain embodiments, where the master link slot 105 is angled or offset, the master link 106 can be configured to stop at any point along the master link slot 105 to change the gap and thus the angle of the anvil assembly 101 relative to the cartridge assembly 103. Angling the master link slot 105 may also improve closing efficiency for the end effector 121.

A second master link pin 138 can be used to pivotally couple the master link 106 to a platform 142 as will be described further herein below. In the embodiment illustrated in FIGS. 3A and 3B, the cartridge frame 116 can be insertable at its proximal end into a support tube 140, thereby aligning and connecting the end effector 121 of the stapling device 100 to the handle portion 123 of the stapling device 100.

The support tube 140 can be an elongated member, having a proximal end and a distal end, that can be configured to extend through a trocar (not shown) such that the end effector 121 of the stapling device 100 can access the organ of a patient. The support tube 140 can be any suitable length such as, for example, from 50 mm to 350 mm, from 100 mm to 350 mm, from 100 mm to 200 mm, from 150 mm to 300 mm, or 100 mm. The support tube 140 can have an outer diameter from 5 mm to 22 mm and can have a wall thickness from 0.25 mm to 1.5 mm, for example.

The support tube 140 can be unitarily formed with a monolithic construction, or in an alternate embodiment, the support tube 140 can include multiple sections. The support tube 140 can have a uniform diameter of any size, for example, to access a body cavity in accordance with a laparoscopic procedure. The proximal end of the support tube 140 can be coupled with the handle portion 123 of the stapling device 100. The support tube 140 may have a handle ring 144 that slidably engages an outside surface of the support tube 140 and supports the alignment and connection of the support tube 140 into the handle portion 123. A tube mount 174 may be affixed to the support tube 140 for attachment to the handle portion 123.

The handle portion 123 of the stapling device 100 can be used to facilitate insertion of the end effector 121 into the body cavity of a patient. The handle portion 123 can include mechanical or motorized components to facilitate actuation of the end effector 121. In one embodiment, the handle portion 123 can include a right handle half 120 and a left handle half 122 that can be coupled together in a clamshell-like fashion. The right handle half 120 and left handle half 122 may be joined, for example, by handle nuts 168, 170 and handle screws 160, 162, 164, or may be ultrasonically welded, press fit, glued, screwed together with self-tapping screws into holes molded into the right handle half 120, or otherwise assembled.

The handle portion 123 can include a trigger 146 that can be used to actuate and activate the stapling device 100. The trigger 146 can include a first mounting feature 148 and a second mounting feature 150 that can be used to attach the trigger 146 such that it is pivotable or moveable relative to the right handle half 120 and left handle half 122. A trigger stop 158 can be positioned in handle portion 123, adjacent the trigger 146, and can include centering springs 152, 154 and a reset spring 156 that can be used, respectively, to center and reset the trigger stop 158 in coordination with the use of the trigger 146. One embodiment of the operation of the handle portion 123 and the trigger 146 is shown in more detail in FIGS. 5A-5B.

The tube mount 174 of the support tube 140 can engage features in the right handle half 120 and left handle half 122 to couple the support tube 140 to the handle portion 123. The platform 142 can be coupled through the support tube 140 to a rack 176 of teeth or other engagement features that can engage a pawl arm 128. The pawl arm 128 can be biased toward the rack 176 using a pawl spring 130. The pawl arm 128 can be retained at least partially within the handle portion 123 and can include a left release lever 126 and a right release lever 124 that can be used ambidextrously to overcome the bias of the pawl spring 130 and lift a pawl 208 of the pawl arm 128 from the rack 176.

In one embodiment, an electric motor 192 containing an armature 193 can be insertable into a motor mount 194 and can be attached via screws 190 to be used as a driver or actuator. In certain embodiments, the electric motor 192 can be selectively removable from the motor mount 194 for reuse by an operator, where the end effector 121 and/or support tube 140 may be single use and disposable.

The electric motor 192 and a switch 196 can be held in the motor mount 194 using a cap 197 and an outer cap 198. The armature 193 can be coupled to a rotating member 180 using a gear 186 and a hub 188. A thrust washer 184 can be used to provide an abutment for a trigger return spring 181. A switch 134 associated with a switch pad 132 can be used in coordination with the switch 196 to engage the electric motor 192 to activate the rotating member 180. The motor mount 194 can be mountable into the handle portion 123 using a left mount arm 195 and a right mount arm 199 and can be fixed in place via pins formed in the left handle half 122 and left release lever 126, using screws such as handle screw 164, or other holding structures or methods.

Figure 5A:
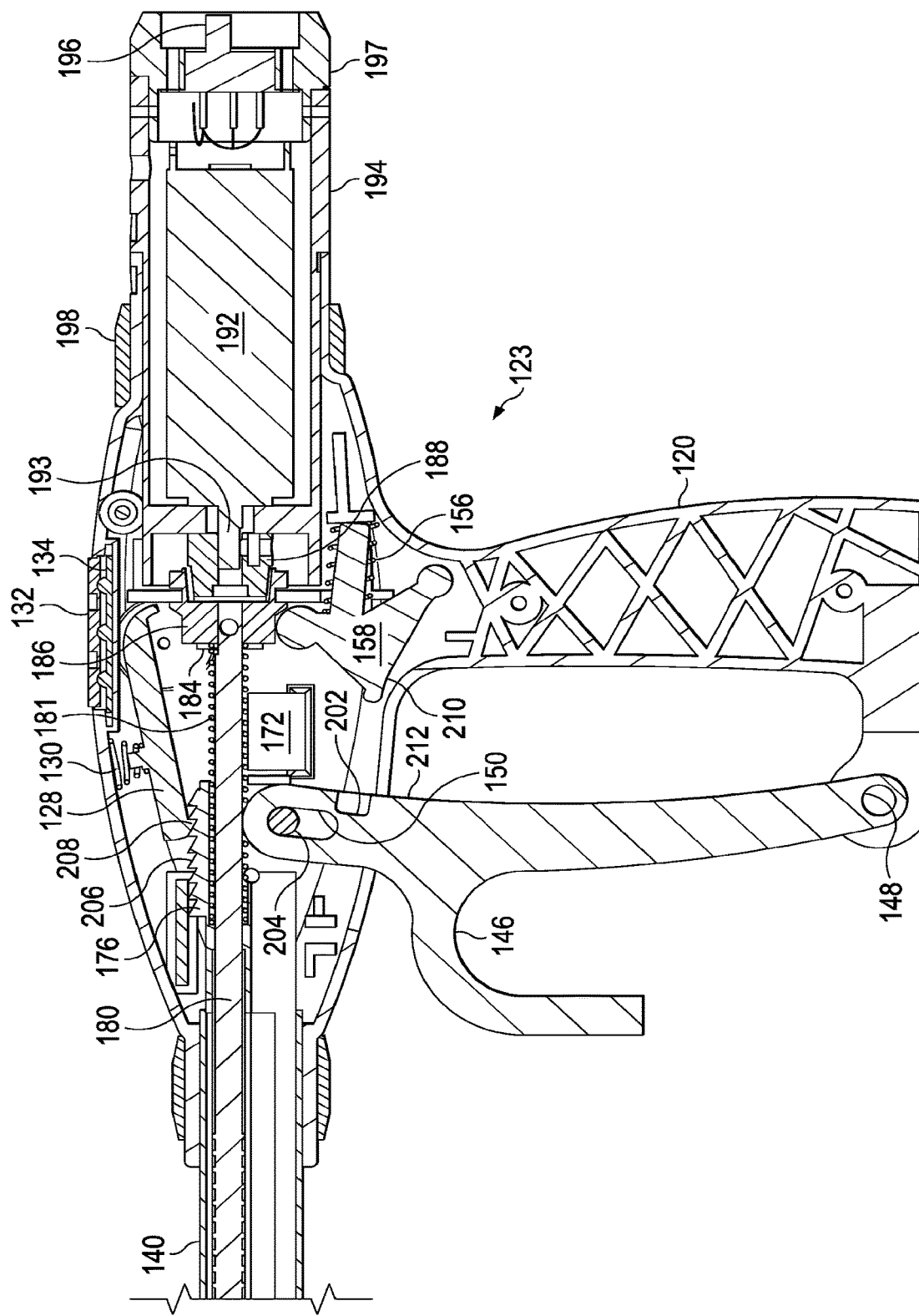
FIG. 5A depicts a cross-sectional side view of the handle portion, taken along section B-B, of the stapling device shown in FIG. 2B in a first position.
Figure 5B:
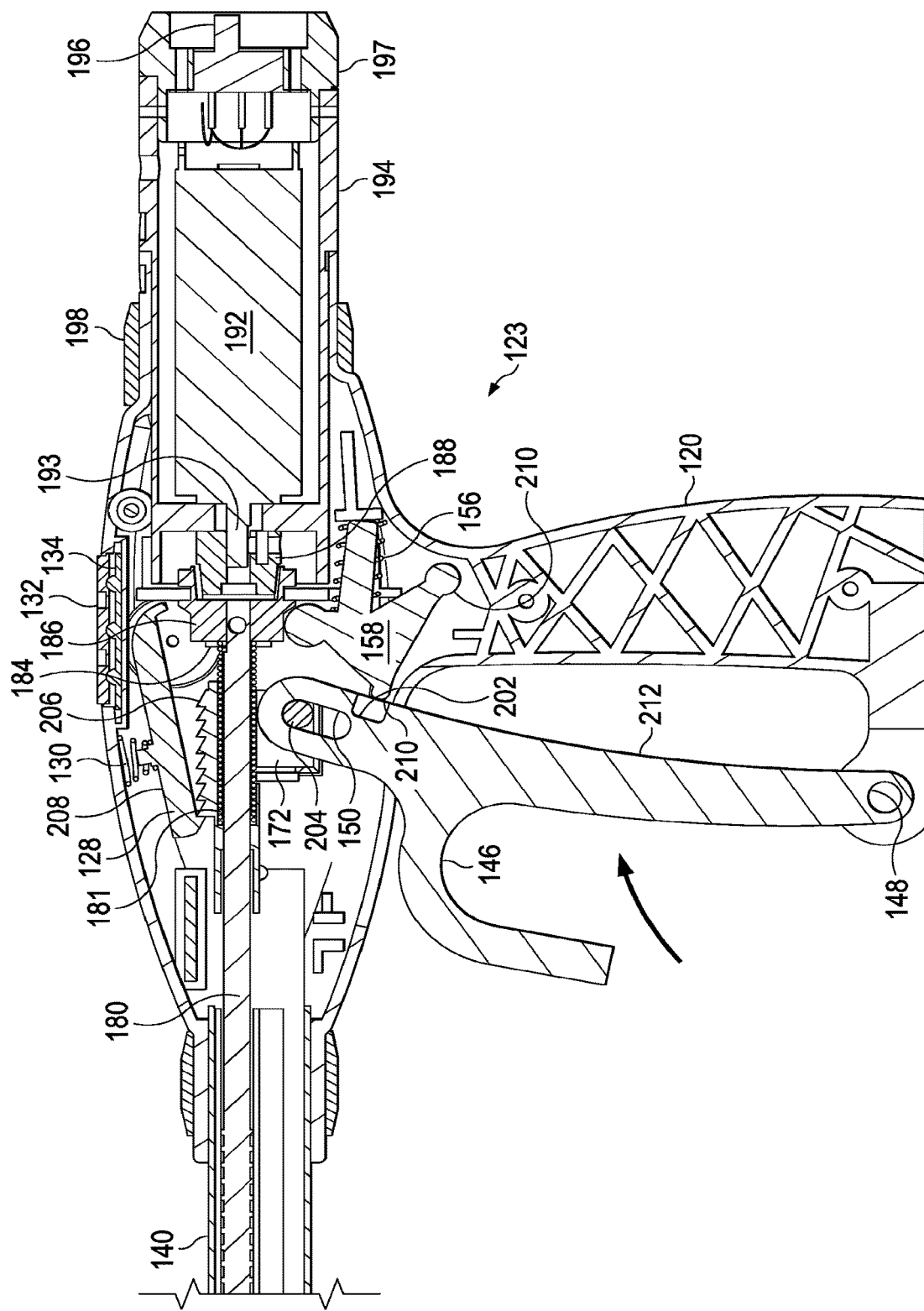
FIG. 5B depicts a cross-sectional side view of the handle portion, taken along section B-B, of the stapling device shown in FIG. 2B in a second position.

FIG. 5A is a cross-sectional side view of the handle portion 123 of the stapling device 100 shown in a first open position (see, for example, FIG. 2A). FIG. 5B is a cross-sectional side view of the handle portion 123 transitioned to a second closed position (see, for example, FIG. 2B). The second mounting feature 150 of the trigger 146 can include an elongated slot such that a trigger pin 204 can move within the second mounting feature 150 in a non-load bearing direction while the trigger 146 applies a load to the platform 142 as the trigger 146 is pulled proximally. As the trigger 146 is urged proximally, the second mounting feature 150 can correspondingly apply a force to the trigger pin 204 that urges the platform 142 proximally. The rack 176 can be rigidly attached to a proximal end of the platform 142 such that as the trigger 146 is urged proximally the teeth 206 of the rack 176 engage the pawl 208 on the pawl arm 128 to prevent distal movement of the rack 176 and platform 142. The rack 176 and platform 142 can be prevented from moving distally until, for example, a left release lever 126 (FIG. 3) or a right release lever 124 (FIG. 3) is pressed to release the pawl 208 from the teeth 206 of the rack 176. A plurality of teeth 206 on the rack 176 can provide for incremental closing of the end effector 121 as the trigger 146 is pulled, which can allow for precise positioning of the end effector 121 on tissue. The clinician can urge the trigger 146 proximally until a desirable compression or position on the tissue is achieved. If the clinician needs to reposition the stapling device 100, the right release lever 124 or left release lever 126 can be actuated to open the stapling device 100 to release the tissue.

The handle portion 123 can include a trigger stop 158 having a trigger stop tip 210. As shown in FIG. 5B, the trigger 146 can be urged proximally until a trigger edge 212 on the trigger 146 touches the trigger stop tip 210, which can prevent further proximal movement of the trigger 146. In one embodiment, when the trigger 146 engages the trigger stop the stapling device 100 is in the fully closed position (see, for example, FIG. 2B). In the fully closed positioned, the endocutter can be used to deploy staples and/or transect tissue.

Figure 5C:
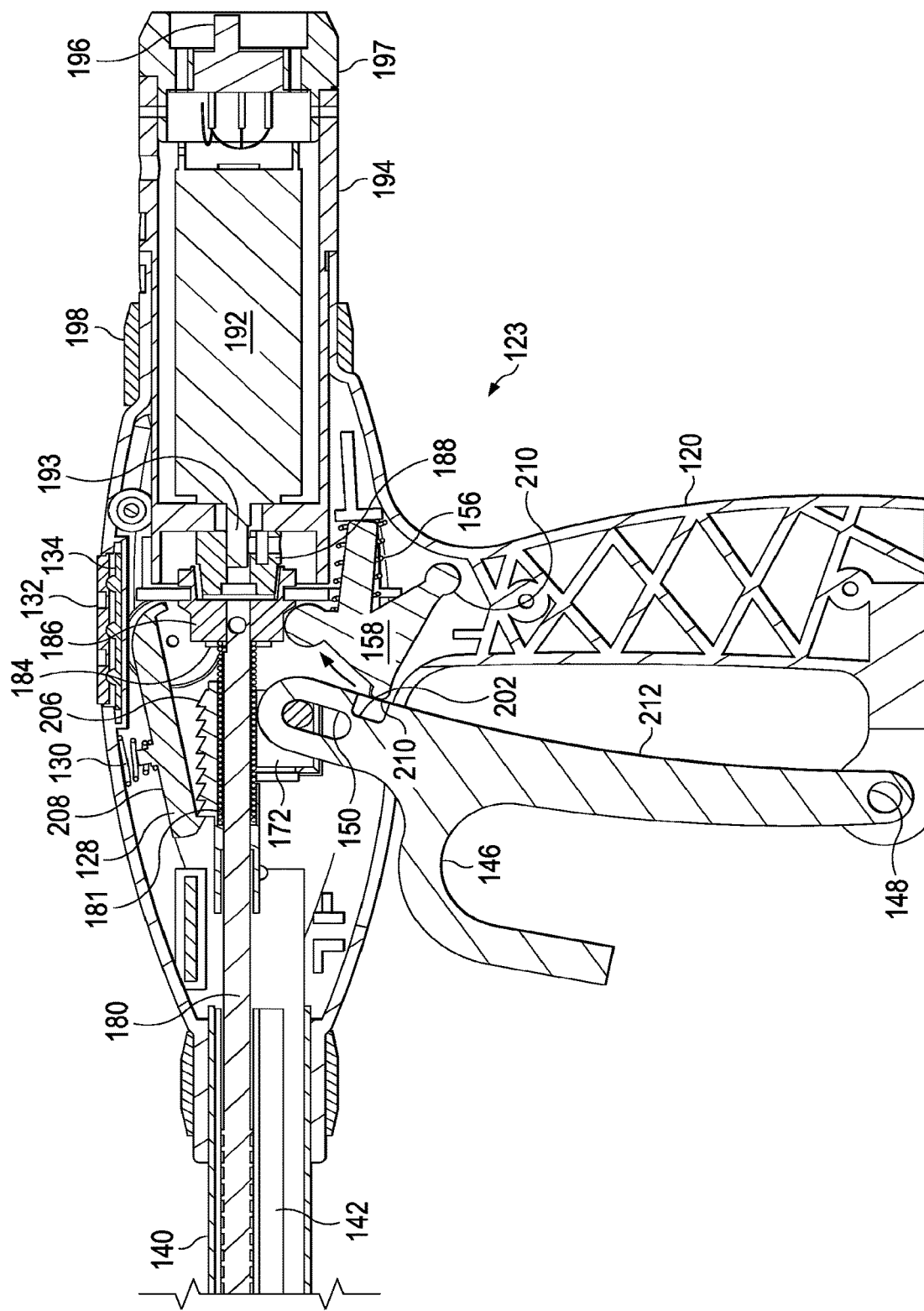
FIG. 5C depicts a cross-sectional side view of the handle portion, taken along section B-B, of the stapling device shown in FIG. 2B in a third position.

Referring to FIG. 5C, once the stapling device 100 is in a closed position it can be transitioned to a third pre-firing position. In one embodiment, the stapling device 100 can be fired only after the trigger stop 158 is moved laterally relative to the trigger 146 such that the trigger stop tip 210 is aligned with a trigger release recess 202. Once the trigger stop 158 is aligned with the trigger release recess 202 the trigger 146 can be urged further proximally such that the trigger stop tip 210 enters the trigger release recess 202. The trigger stop 158 can be urged laterally by a clinician, for example, by compressing the centering spring 152 or centering spring 154, to permit the trigger stop tip 210 to move laterally relative to the trigger edge 212 until the trigger stop tip 210 engages the trigger release recess 202.

Figure 5D:
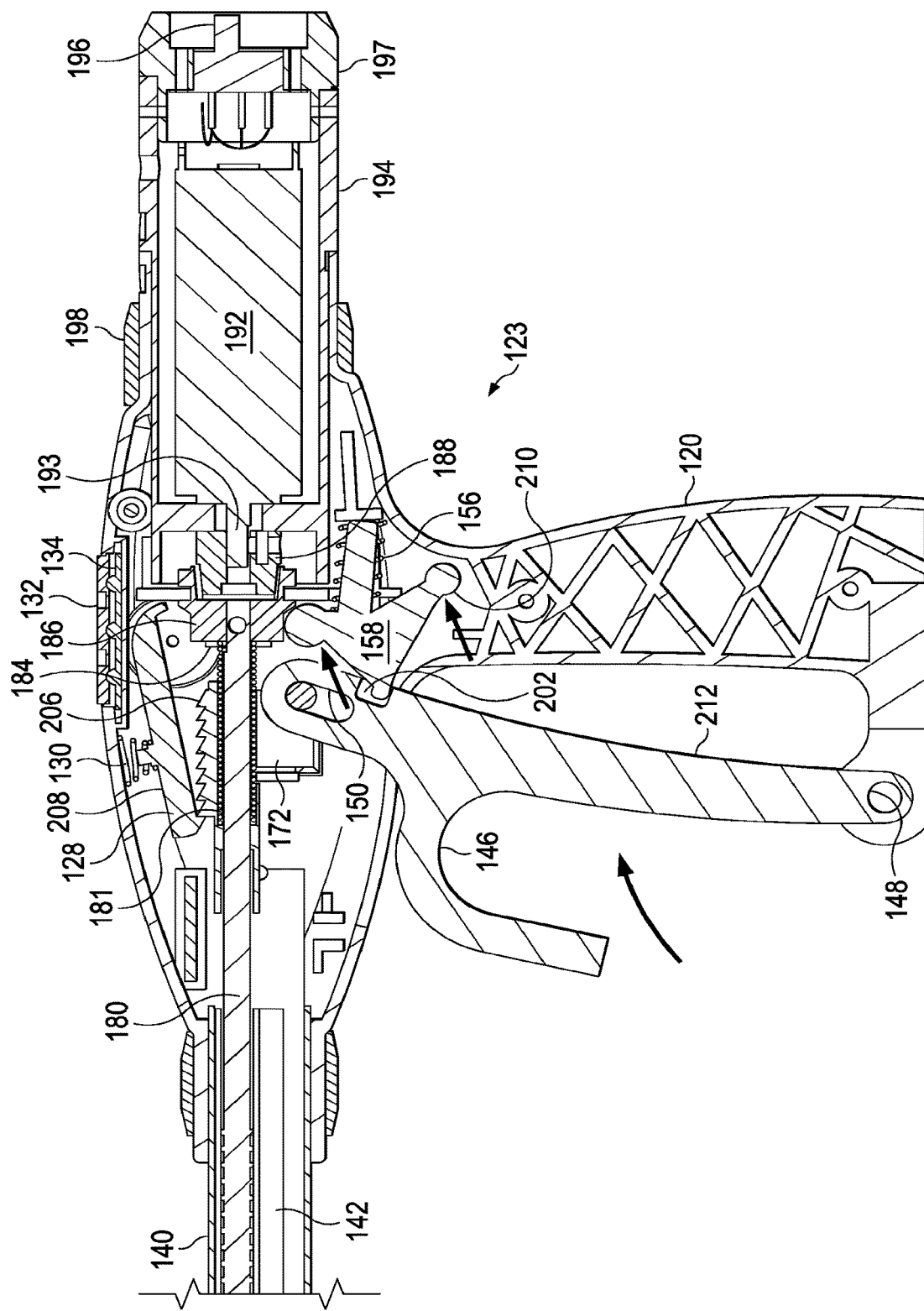
FIG. 5D depicts a cross-sectional side view of the handle portion, taken along section B-B, of the stapling device shown in FIG. 2B in a fourth position.

Referring to FIG. 5D, when the trigger stop tip 210 is aligned with the trigger release recess 202, the trigger 146 can be urged more proximally to a fourth firing position to actuate a switch 172 that engages the electric motor 192 to drive the blade assembly 108. Driving the blade assembly 108 can correspondingly cause the stapling device 100 to provide a staple line while simultaneously cutting tissue. A nut 109 (FIGS. 6 and 7) can be coupled to the blade assembly 108 and can transfer a force to the blade assembly 108 from the rotating member 180 as the rotating member 180 is actuated by the electric motor 192.

Figure 5E:
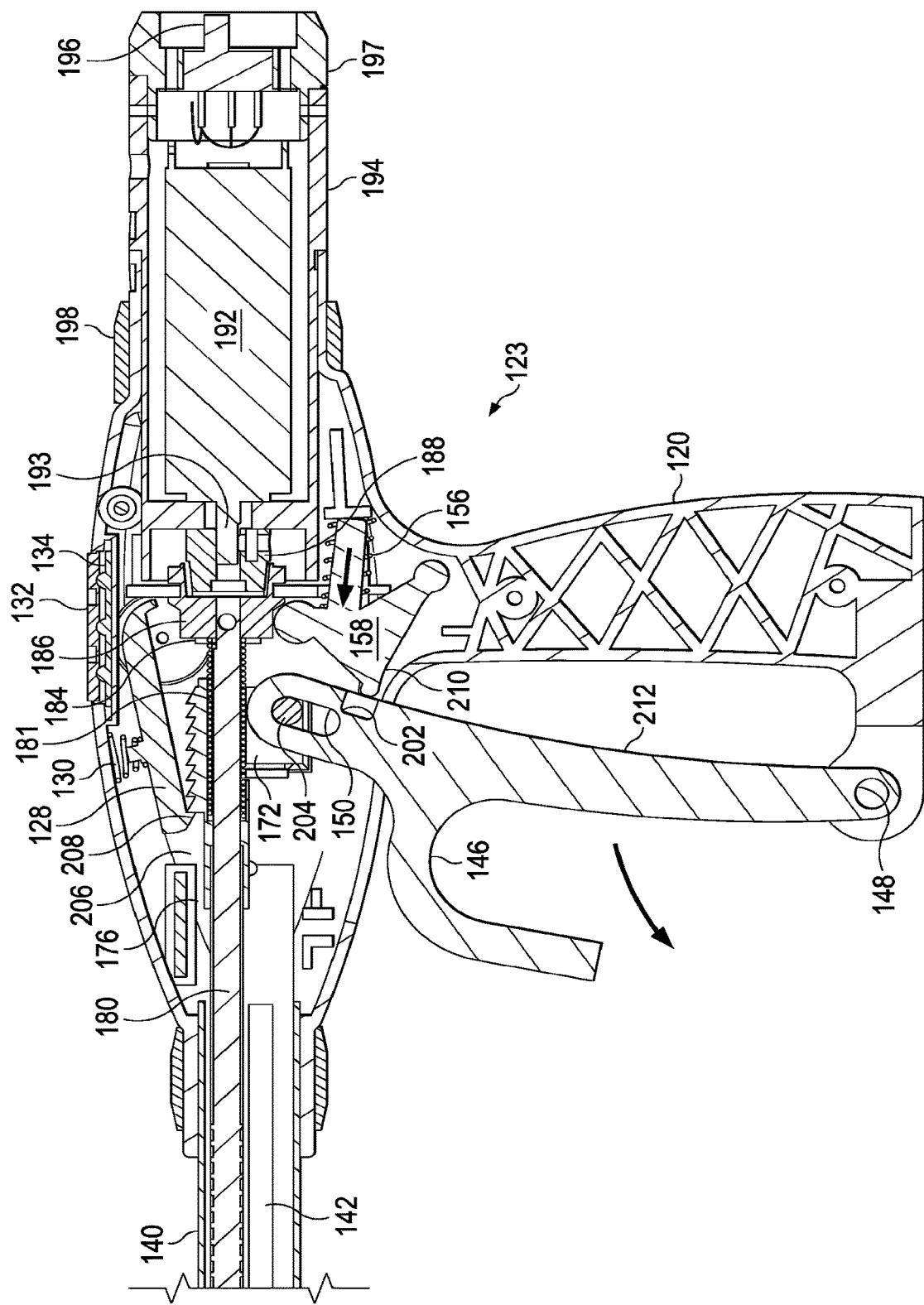
FIG. 5E depicts a cross-sectional side view of the handle portion, taken along section B-B, of the stapling device shown in FIG. 2B in a fifth position.

Referring now to FIG. 5E, when the trigger 146 is released, the reset spring 156 can urge the trigger stop 158 distally such that the switch 172 disengaged the electric motor 192 is turned off. The centering spring 152 and centering spring 154 can then re-center the trigger stop 158 and reset the stapling device 100 such that the electric motor 192 cannot be inadvertently reengaged.

Figure 6:
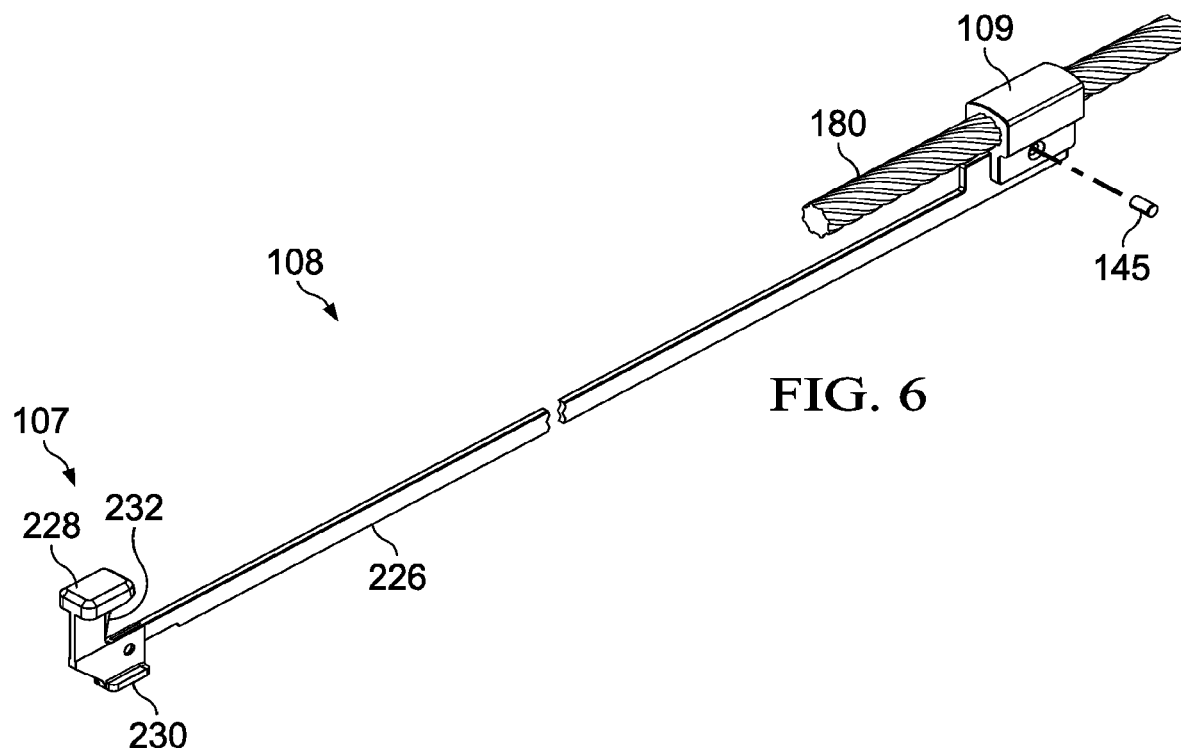
FIG. 6 is a partial perspective view of a blade assembly and a drive mechanism for a surgical device according to one embodiment.
Figure 7:
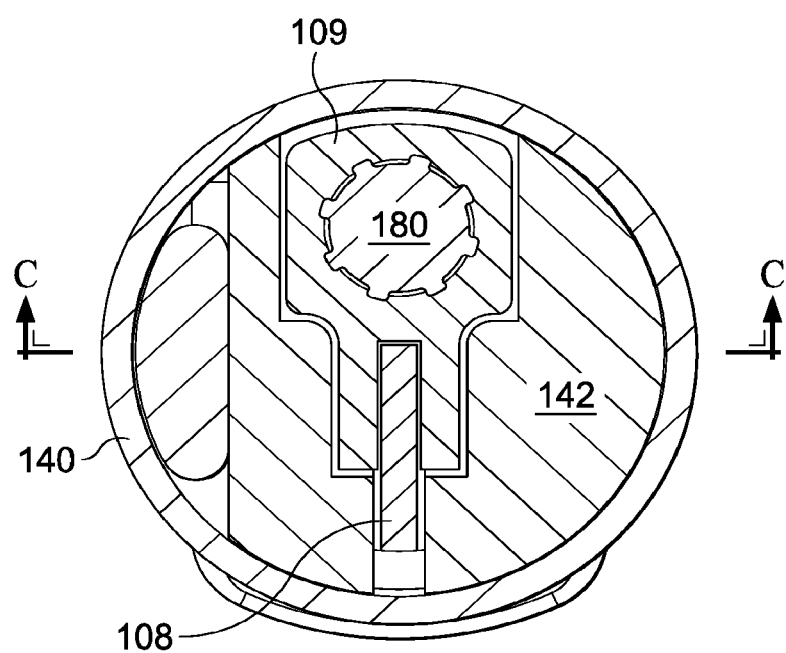
FIG. 7 depicts a cross-sectional view of the elongated support tube shown in FIG. 2B, taken along section C-C, illustrating the relationship between the blade assembly and the drive mechanism shown in FIG. 6, according to one embodiment.

Referring to FIG. 6, shown is a perspective view of the blade assembly 108 illustrating that the nut 109 can be attached to the blade assembly 108 via a pin 145, a spot weld, or can be formed monolithically as a unitary construction with the blade assembly 108. The blade 107 can be affixed to a distal end of the blade assembly 108 and can be urged, for example, from a distal position to a proximal position to cut tissue during staple formation. FIG. 7 illustrates a cross-sectional view of one example of the relationship between the support tube 140, the platform 142, the nut 109, and the rotating member 180. It will be appreciated that any suitable coupling that facilitates the transfer of force from the rotating member 180 to the blade assembly 108 is contemplated.

In embodiments, the blade 107 can be urged proximally to cut tissue while at the same time deploying the staples from the cartridge 110. It may be advantageous for the blade 107, supported by an elongate beam 226, to be positioned at the distal end of the end effector 121 prior to delivering staples and cutting the tissue. The elongate beam 226 may provide additional support to the cartridge frame 116 during positioning and transition of the end effector 121 from the open position to the closed position.

As discussed with reference to FIG. 3A, FIG. 3B, and FIG. 4, the blade 107 can include a top portion 228 that can be sized to slidably move within the anvil blade channel 139 and the blade 107 can include a bottom portion 230 that can be sized to slidably move within the cartridge blade channel 141. In one embodiment, as the blade 107 is urged proximally to cut tissue, the top portion 228 and the bottom portion 230 of the blade 107 can compress the end effector 121 to provide advantageous compression to the tissue.

It will be appreciated that the manually operated embodiments of the stapling device 100 are described by way of example only. For example, the handle of the stapling device 100 can be a control unit from a surgical robot and the stapling device 100 can be actuated remotely using a surgical robot or other electromechanical systems, such as by electric motor, cable and pulley, pneumatic or hydraulic mechanisms.

Figure 8:
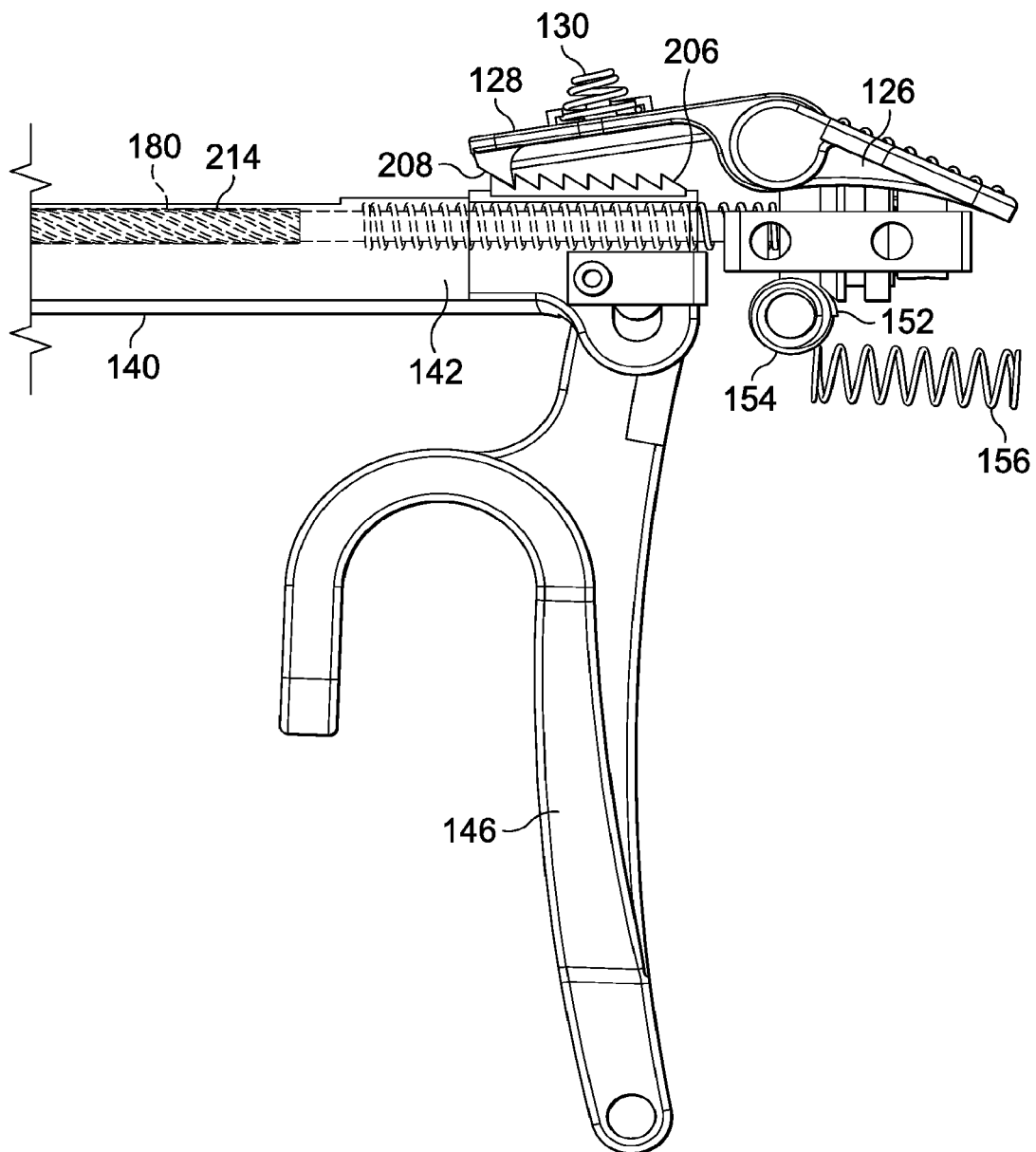
FIG. 8 depicts a partial cross-sectional side view of the handle portion shown in FIG. 2B illustrating the relationship between the blade assembly and the drive mechanism, shown in FIG. 6, according to one embodiment.

FIG. 8 is a cross-sectional side view of selected components of the handle portion 123 of the stapling device 100 in accordance with at least one embodiment. The rotating member 180 can include threaded or spiral cut grooves 214 that can be used to actuate the stapling device 100. As the rotating member 180 is actuated, corresponding threads on the nut 109 can urge the nut 109 in a proximal or distal direction. The nut 109, being coupled to the elongate beam 226 of the blade assembly 108, can advance the blade 107 in a proximal or distal direction.

Figure 9:
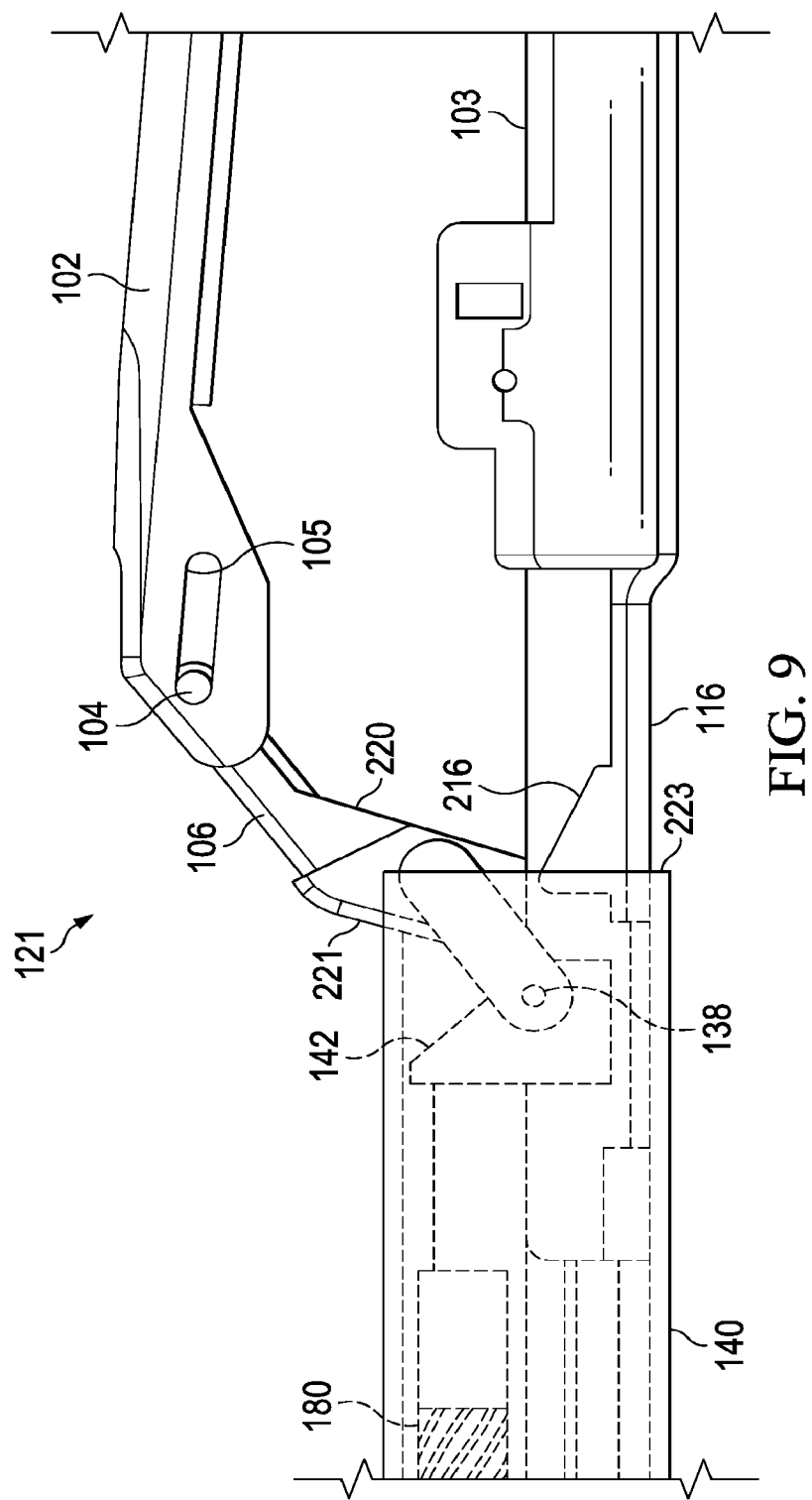
FIG. 9 depicts a side view of a proximal end of the end effector shown in FIG. 2A.

FIG. 9 is a side view of one end of the end effector 121 in accordance with at least one embodiment. In the illustrated version, the cartridge frame 116 is illustrated extending into the support tube 140, which may provide advantageous stiffness and support for the end effector 121. The cartridge frame 116 can include a ramp 216 that can be unitarily formed as a monolithic structure with the cartridge assembly 103, or may be a separate component that can be affixed to the cartridge frame 116. The ramp 216 can be positioned to interfere with a ramp surface 220 of the master link 106. As the platform 142 is advanced distally, the ramp surface 220 can engage the ramp 216 to urge the master link 106 upward to open the end effector 121. The ramp 216 can have any suitable shape and configuration that can cause the master link 106 to open or otherwise space apart the cartridge assembly 103 and the anvil assembly 101. In an alternate embodiment (not shown), the ramp can be replaced with a spring to bias the master link in an open, or up, position.

As the platform 142 is advanced, the first master link pin 104 can engage the distal end of the master link slot 105 to urge the anvil assembly 101 upward or away from the cartridge assembly 103. The master link slot 105 can be an elongated channel that can be sized such that the platform 142 and master link 106 can move proximally and distally along a longitudinal axis to allow the master link 106 to apply an opening and closing force to the anvil frame 102. The master link slot 105 can be sized such that, after the end effector 121 is fully closed and the master link 106 is horizontal within the support tube 140, the master link slot 105 can permit the trigger 146 to be advanced farther proximally to engage the trigger edge 212 with the switch 172.

Still referring to FIG. 9, the master link 106 can include a second surface 221 that can contact a tube edge 223 of the support tube 140 as the trigger 146 is actuated. To close the end effector 121, as the platform 142 is urged proximally, the second surface 221 can be pushed by the tube edge 223 to move the anvil frame 102 towards the cartridge assembly 103. The ramp surface 220 can facilitate opening the stapling device 100 and the second surface 221 can facilitate closing the stapling device 100 for improved action of the stapling device 100 during use. In one embodiment, coupling the first end of the master link 106 to the platform 142 and the second end of the master link 106 to the anvil frame 102 can facilitate actuation of the end effector 121 without requiring actuation of the support tube 140.

As shown in FIG. 9, the master link 106 can be pivotally attached at a first end by the first master link pin 104 at a second end of by the second master link pin 138. The master link 106 can have a linear configuration or, as shown in FIG. 9, the master link can have a first linear portion originating at about the second master link pin 138 and a second linear portion connected to the anvil frame 102 via the first master link pin 104. The first linear portion and the second linear portion can be offset, for example, between 1.5 and 10.0 millimeters, and may be offset by 2.5 millimeters. The included angle between the linear portions and the ramp surface 220 and second surface 221 can be, for example, from 20 degrees to 50 degrees, or 37 degrees. The distance between the first master link pin 104 and the second master link pin 138 can be from 10 mm to 50 mm, from 15 mm to 20 mm, or 18 mm. The length of the second surface 221 can be from 15 mm to 22 mm, from 10 mm to 30 mm, or 18 millimeters from the top of the first linear portion to the top of the second linear portion. The master link slot 105 can have a length of 4 mm to 9 mm, 3 mm to 8 mm, or 6 mm to provide for desirable movement of the first master link pin 104 within the master link slot 105. The height and width of the master link 106 can be from 3 mm to 13 mm, or 6 mm, for example, to provide for strength and rigidity while still fitting within the profile of the end effector 121. The material of the master link 106, in combination with the size of the master link 106, can be selected to ensure the master link 106 can withstand closure loads of, for example, from 10 lbs to 100 lbs. In one embodiment, the width of the master link 106 is 8 mm, the height of the master link 106 is 4.6 mm, and the material of construction for the master link 106 is stainless steel.

Figure 10:
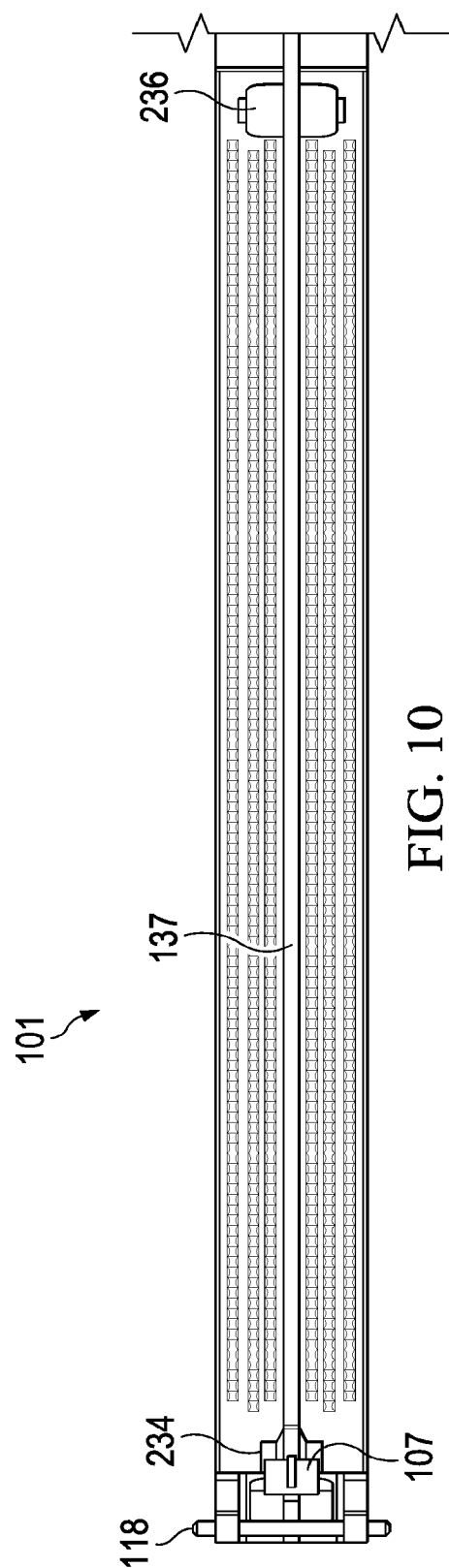
FIG. 10 depicts a partial bottom plan view of an anvil assembly according to one embodiment.

FIG. 10 depicts a bottom plan view of the anvil assembly 101 according to one embodiment. The blade 107 is shown positioned at one end of the anvil frame 102 in a first opening 234. As the anvil assembly 101 is closed against the cartridge assembly 103, the cutting 107 can enter the anvil plate channel 137 to cut tissue between the staples. After reaching the end of its cutting sequence, the blade 107 can enter a second opening 236 that can allow the end effector 121 to be opened. The blade 107 can be guided through the anvil plate channel 137 to keep the blade 107 centered.

Figure 11:
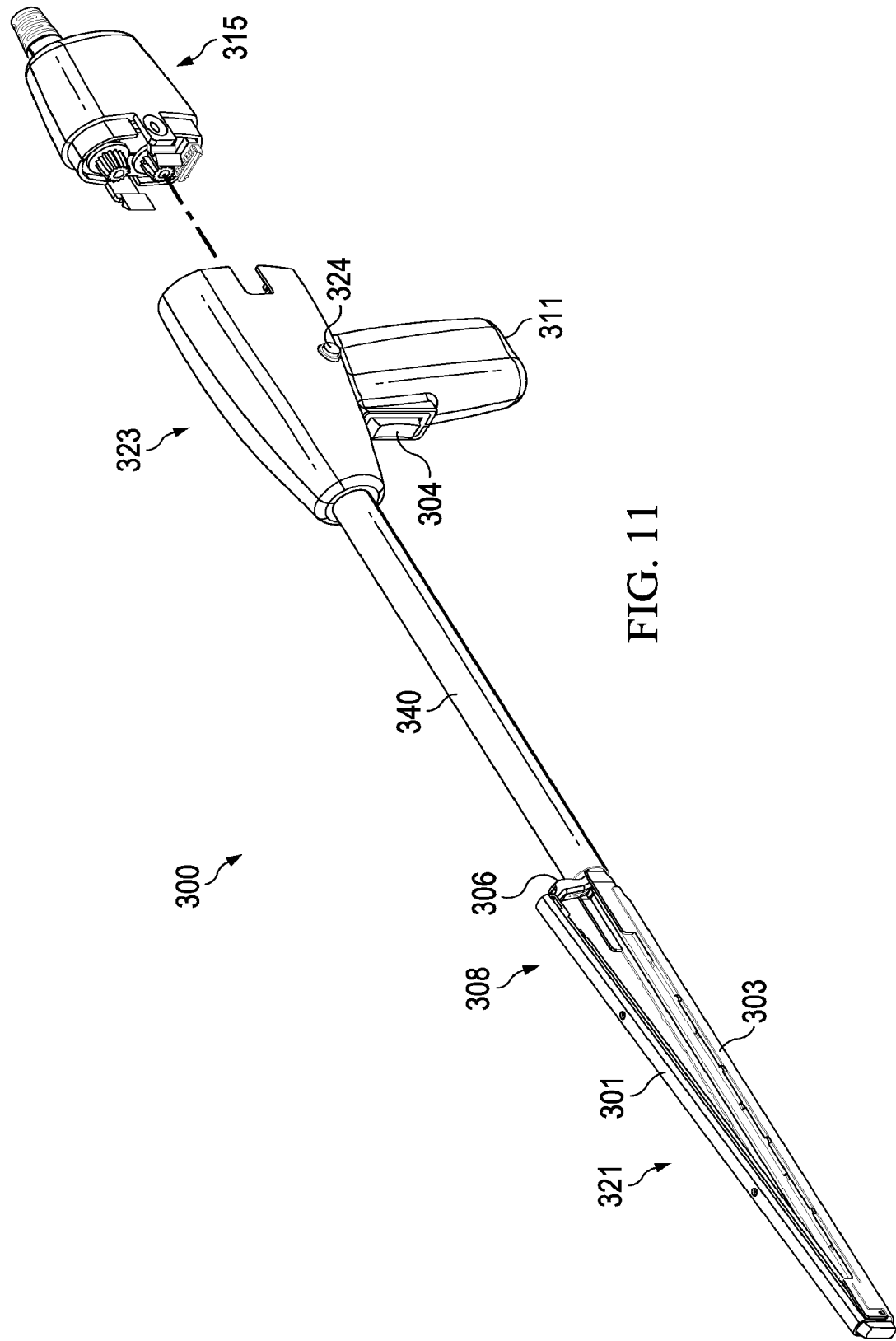
FIG. 11 depicts a perspective view of a stapling device, shown in an open position, having an end effector, an elongated tube, a handle portion, and a motor in accordance with an alternate embodiment.

FIG. 11 is a perspective view of a stapling device 300 in accordance with one embodiment. The stapling device 300 can include an endocutter 308 and a motor assembly 315. The stapling device 300 comprising an end effector 321 including an anvil assembly 301 and a cartridge assembly 303, a support tube 340 and a handle portion 323. The anvil assembly 301 can function as a first jaw of the end effector 321 and the cartridge assembly can function as a second jaw of the end effector 321. The end effector 321 can be connected to the handle portion 123 via a support tube 340. The handle portion 323 can include a handle 311 and a trigger 304 for actuating the stapling device 300.

The handle portion 323 can include a mode button 324 for switching between operational modes. For example, in a first mode, the trigger 304 can be pressed upwards to open the jaws (e.g., the anvil and cartridge) or pressed downward to close the jaws. When the jaws are in a closed position, the mode button 324 can be depressed to transition the stapling device 300 into a firing mode. When in the firing mode, depressing the trigger 304 can fire the stapling device 300 to simultaneously form a staple line comprising of one or a plurality of rows of staples while cutting tissue. In one embodiment, depressing the trigger 304 in the firing mode can deploy a staple line including six rows of staples, where a knife (not shown) can simultaneously cut tissue between a third and a forth row of the staples.

Figure 12:
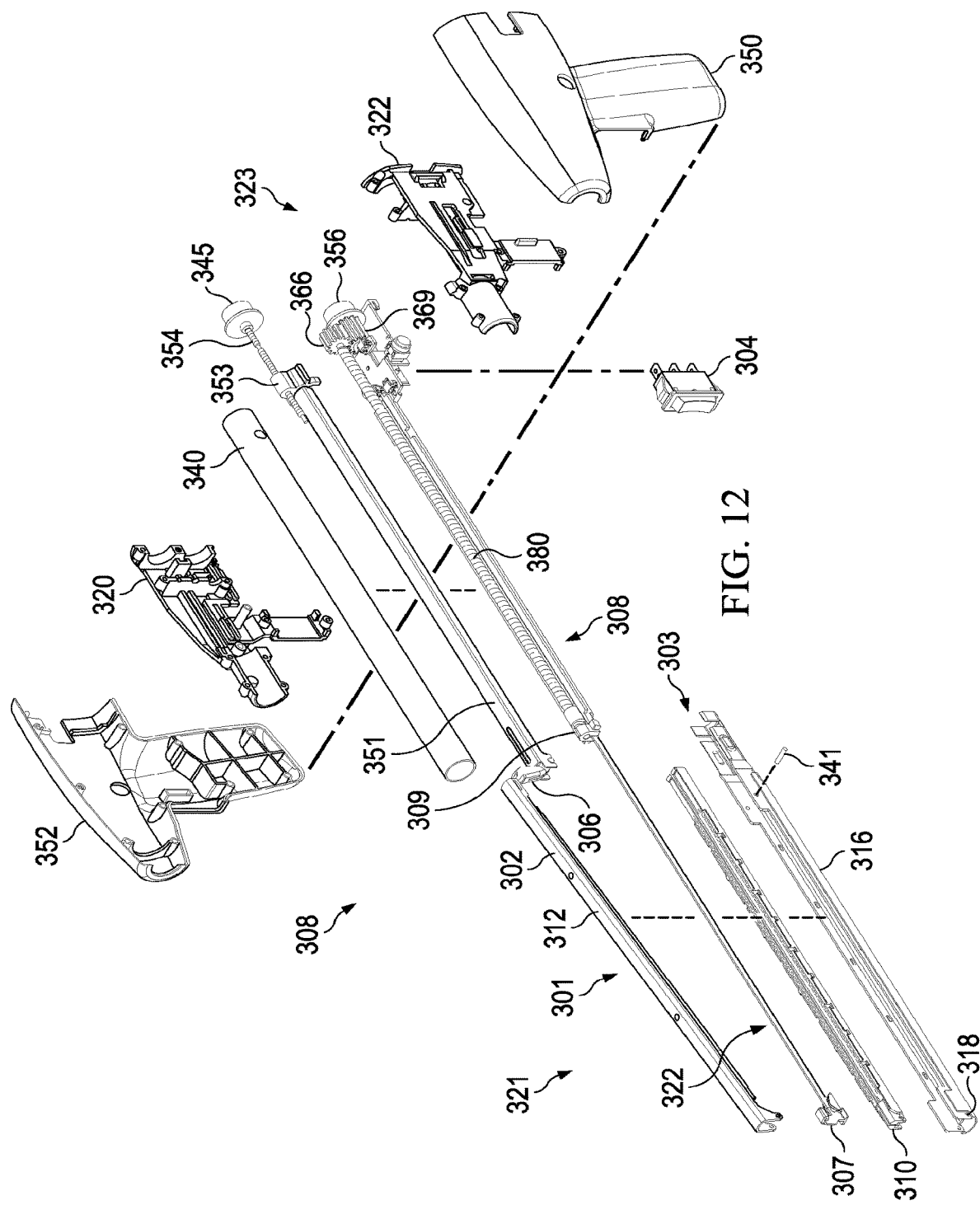
FIG. 12 is a partially exploded perspective view of the end effector, elongated tube, and handle portion of the stapling device shown in FIG. 11.

FIG. 12 depicts an exploded perspective view of the endocutter 308 in accordance with at least one embodiment. The anvil assembly 301 can include an anvil frame 302 and an anvil plate 312. The anvil plate 312 can be welded to the anvil frame 302, or may be otherwise attached such as by gluing, brazing, sintering, machining, 3D printing or the like. A cartridge 310 containing a plurality of staples can be attached to the cartridge frame 316 by a first cartridge pin 341 at a first end and a second cartridge pin 318 at a second end, or alternately the cartridge 310 can be attached to the cartridge frame 116 via snap fit, gluing, or other attachment methods.

In the embodiment illustrated in FIG. 12, the cartridge frame 316 can be insertable at its proximal end into the support tube 340 to align and connect the end effector 321 of the endocutter 308 to the handle portion 323. A blade assembly 322 can include a knife or blade 307 that can be coupled to a rotating member 380 via a bushing.

The handle portion 323 can include a right handle half 320 and a left handle half 322 that can be held together in a clamshell-like fashion. The right handle half 320 and left handle half 322 can be joined by, for example, ultrasonic welding, glue, screws, gripper pins or press-fit pins fit into holes molded into the handle, or other assembly methods. A left handle shell 350 and a right handle shell 352 can be used to provide a pleasing aesthetic look to the exterior of the handle portion 323 by covering the left handle half 322 and the right handle half 320.

A drive screw 354 can be used to drive a control arm 351 via a control arm nut 353. The drive screw 354 can be connected to a second drive gear coupler 345 that can engage the motor assembly 315. The rotating member 380 can be coupled to the motor assembly 315 via a firing drive gear 366 and a second firing drive gear 369, where the second firing drive gear 369 can engage the first drive gear coupler 356 that can be coupled with the motor assembly 315. In one embodiment, the second firing drive gear 369 and the first drive gear coupler 356 can be a single component or feature.

Figure 13:
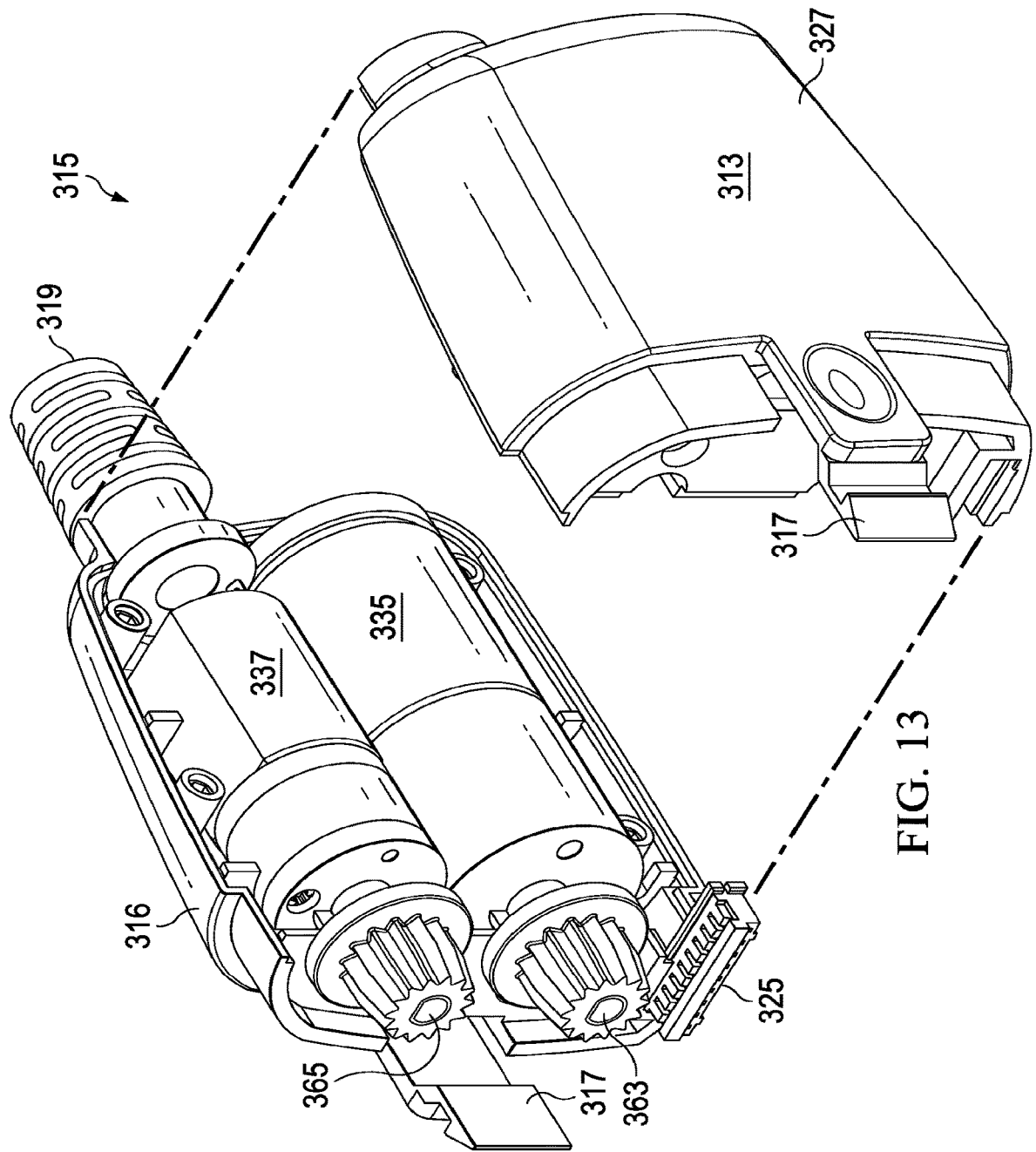
FIG. 13 is a partially exploded perspective view of the motor of the stapling device shown in FIG. 11.

FIG. 13 is a perspective view of the motor assembly 315 in accordance with one embodiment. A first electric motor 335 and a second electric motor 337 can be provided in a motor housing 313. In one embodiment, the first motor gear 363 can be coupled with the first drive gear coupler 356 (FIG. 12) and a second motor gear 365 can be coupled with the second drive gear coupler 345 (FIG. 12). The motor housing 313 can include a left motor housing half 327 and a right motor housing half 316. The motor housing 313 can include snaps 317 to couple the motor assembly 315 with the handle portion 323. A strain relief 319 can be provided to support wiring to the motor assembly 315. A connector 325 can provide for electrically coupling the trigger 304 (FIG. 12) and other electrical components between the motor assembly 315 and the stapling device 300.

FIG. 14A is a side view of the stapling device 300 in accordance with one embodiment showing the end effector 321 in an open position. The end effector 321 can include a first jaw comprising the anvil assembly 301 and a second jaw comprising the cartridge assembly 303. The end effector 321 can include a master link 306 operably coupled with the motor assembly 315.

FIG. 14B is a side view of the stapling device 300 showing the end effector 321 in a closed position. The end effector 321, in its closed position, can be ready for firing, which can include deploying staples and/or cutting tissue. In one embodiment, the end effector 321 can include a blade 307 (FIG. 12) to cut tissue while deploying staples.

FIG. 15 depicts a cross-sectional side view of the handle portion 323 of the stapling device 300 in the open position (e.g., the position shown in FIG. 14A). A second drive gear coupler 345 for opening and closing the end effector 321 can be coupled to the second motor gear 365 (FIG. 13) associated with the second electric motor 337. The second drive gear coupler 345 can rotate the drive screw 354 to open and close the end effector 321 to transition the end effector 321 between an open position to a close position, and vice versa. In FIG. 15, the control arm nut 353 is shown in its distal-most position on the drive screw 354 such that the master link 306 is fully extended and the end effector 321 is in the open position. A control arm distal limit switch 368 can be contacted by the control arm nut 353 in the illustrated position, when the end effector 321 is in the fully open position, to interrupt power to the second electric motor 337. The first drive gear coupler 356 can be coupled to the second motor gear 365 to deploy staples from the stapling device 300 while simultaneously cutting tissue.

FIG. 16 depicts a side view of the end effector 321 of the stapling device 300 shown in the open position. The master link 306 can be attached to a first end of the anvil frame 302 by a first master link pin 320 such that the first master link pin 320 can pivotally and slidably engage master link slot 305. The master link slot 305 can be a channel parallel to the longitudinal axis of the anvil assembly 301, or the master link slot 305 can be angled up or down relative to this longitudinal axis. A second master link pin 338 can be used to pivotally couple the master link 306 to the control arm 351.

Figure 17:
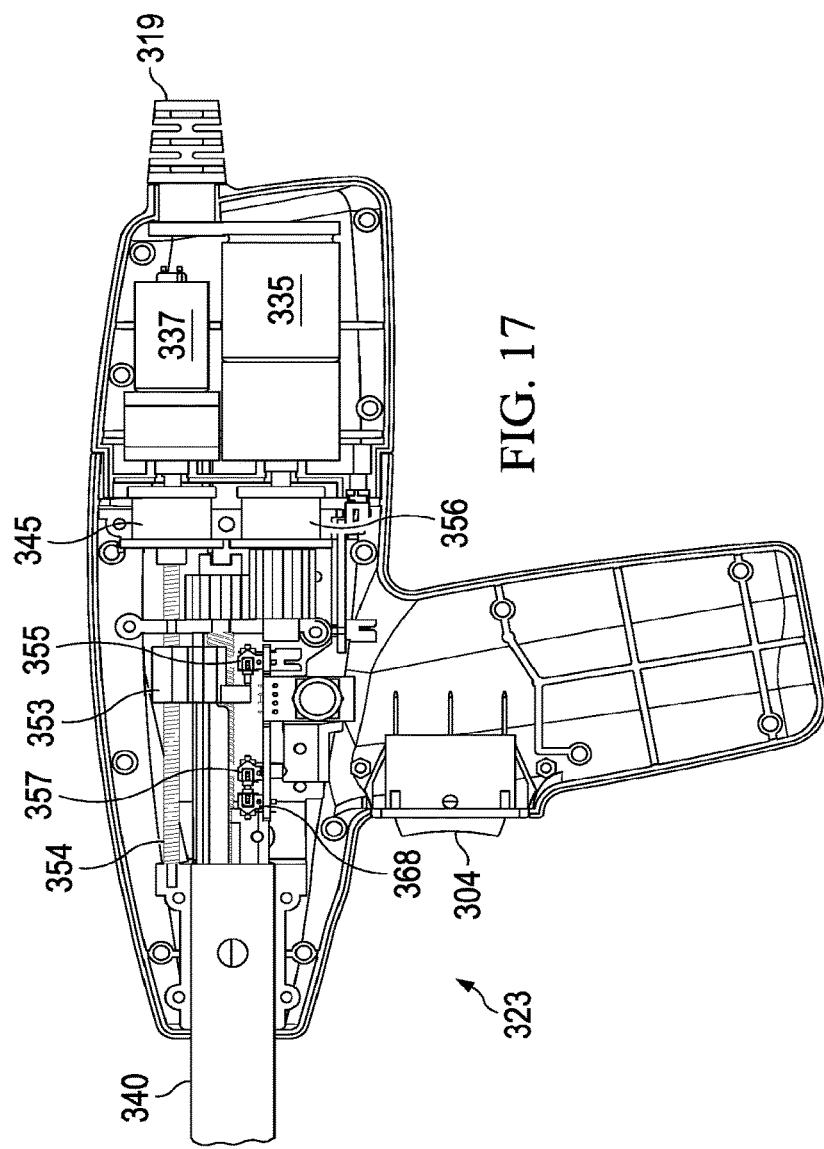
FIG. 17 depicts a side cross-sectional view, taken along section E-E, of the handle portion and the motor shown in FIG. 14B.

FIG. 17 depicts a cross-sectional side view of the handle portion 323 of the stapling device 300 shown in the closed position. The control arm nut 353 is illustrated in its proximal-most position on the drive screw 354 such that the anvil assembly 301 is closed relative to the cartridge assembly 303. In one embodiment, when the end effector 321 is closing, the control arm nut 353 can travel proximally until it contacts a proximal limit switch 355. When the control arm nut 353 contacts the proximal limit switch 355 it can interrupt power to the second electric motor 337. The stapling device 300 can be configured such that it cannot transition into a firing mode until the control arm nut 353 engages the proximal limit switch 355 to ensure that the stapling device 300 is in the closed position before firing.

Figure 18:
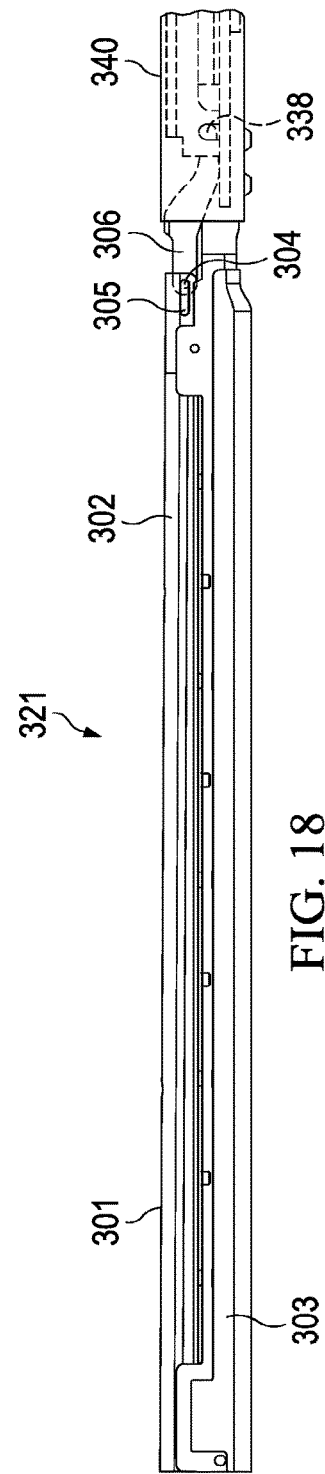
FIG. 18 depicts a side view of the end effector shown in FIG. 14B.

FIG. 18 depicts a side view of the end effector 321 of the stapling device 300 shown in the closed position. The master link 306 is illustrated as inserted partially into the support tube 340 such that the anvil assembly 301 and the cartridge assembly 303 are in a closed position ready for firing.

Figure 19:
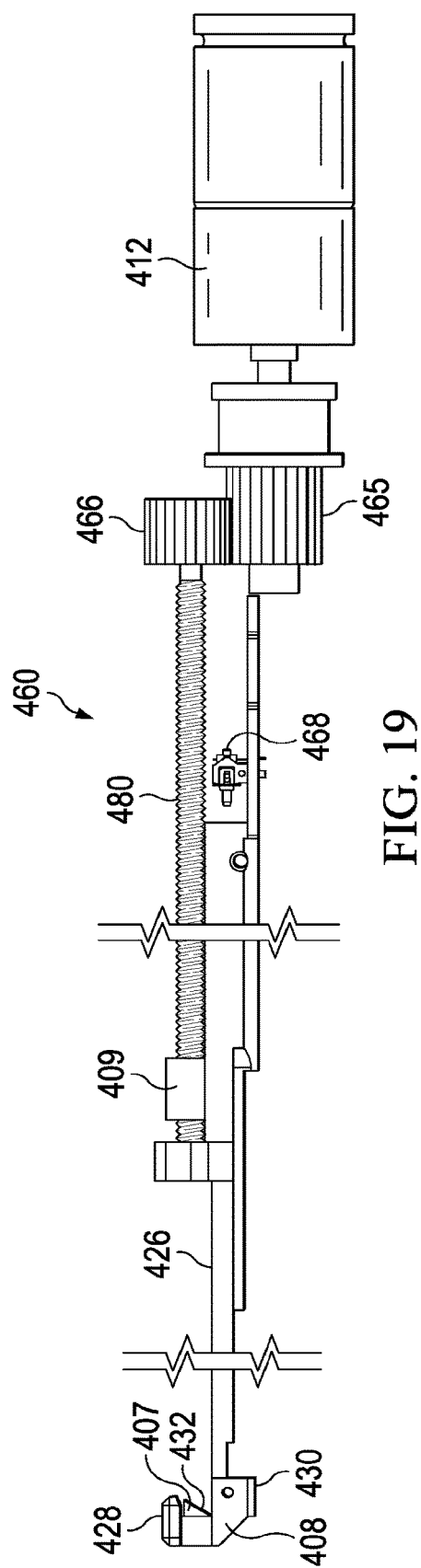
FIG. 19 is a sectioned side view of a blade assembly and a drive assembly for a stapling device according to one embodiment.

FIG. 19 is a side view of a drive assembly 460 for simultaneously stapling and cutting tissue. The drive assembly 460 can include a blade assembly 408 including a blade 407 coupled to a beam 426. The beam 426 can include a nut 409 that can threadedly engage a rotating member 480. The rotating member 480 can be operably coupled with the first electric motor 412 such that rotation of the rotating member 480 urges the nut 409 proximally. During operation, activating the first electric motor 412 can urge the nut 409 proximally such that the beam 426 and blade assembly 408 are correspondingly moved in a proximal direction. As the blade assembly 408 is urged proximally a cutting edge 432 on a blade 407 can transection tissue. The blade 407 can include a top portion 428 and a lower portion 430 that can compress an anvil and a cartridge of an end effector when urged proximally.

Still referring to FIG. 19, when the blade assembly 408 is pulled to its proximal-most position the nut 409 can engage a firing complete limit switch 468. When the nut 409 engages the firing complete limit switch 468 power to first electric motor 412 can be interrupted. It is contemplated that the nut 409 can be attached to the blade assembly 408 or beam 426 in any suitable fashion such as via a pin, a spot weld or other attachment method. Alternatively, the nut 409 can be formed monolithically as a unitary structure with the blade assembly 408 or the beam 426.

Figure 20:
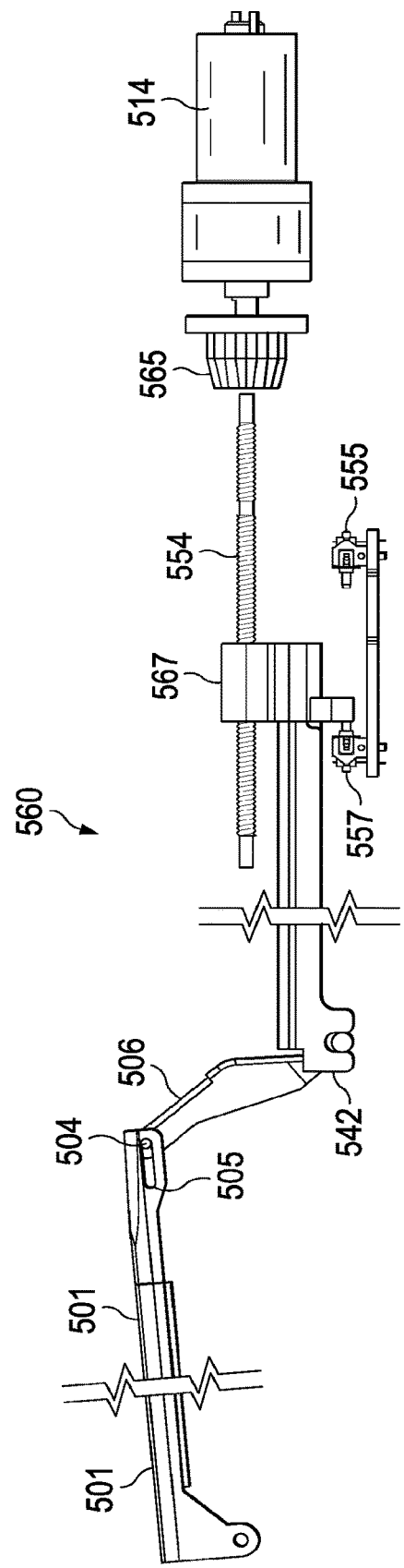
FIG. 20 is a sectioned side view of a blade assembly and a drive assembly for a stapling device according to an alternate embodiment.

FIG. 20 is a side view of a drive assembly 560 for opening and closing an anvil assembly 501 according to one embodiment. Anvil assembly 501 can be moveably coupled with a master link 506, where the master link 506 can be pivotally coupled with a distal end of a platform 542.

In the illustrated embodiment, the master link 506 includes a first master link pin 504 that can engage a master link slot 505 positioned at the proximal end of the anvil assembly 501. The first master link pin 504 can translate within the master link slot 505 to facilitate opening and closing of the anvil assembly 501. A proximal end of the platform 542 can include a drive nut 567 that can threadedly engage a drive screw 554. The drive nut 567 and the drive screw 554 can be coupled such that rotation of the drive screw 554 in a first direction urges the drive nut 567 proximally and rotation of the drive screw 554 in a second direction urges the drive nut 567 distally. A proximal end of the drive screw 554 can be coupled with a second motor gear 565 that is rotationally coupled with a second electric motor 514. During operation, the second electric motor 514 can rotate the drive screw 554 clockwise or counterclockwise to open and close the anvil assembly 501, respectively.

Still referring to FIG. 20, the drive assembly 560 can include a distal limit switch 557 and a proximal limit switch 555. When the anvil assembly 501 is in the fully open position, the drive nut 567 can be in its distal-most position such that it contacts the distal limit switch 557 to interrupt power to the second electric motor 514. When the anvil assembly 501 is in the fully closed position, the drive nut 567 can be in its proximal-most position such that it contacts the proximal limit switch 555 to interrupt power to the second electric motor 514.

Figure 21:
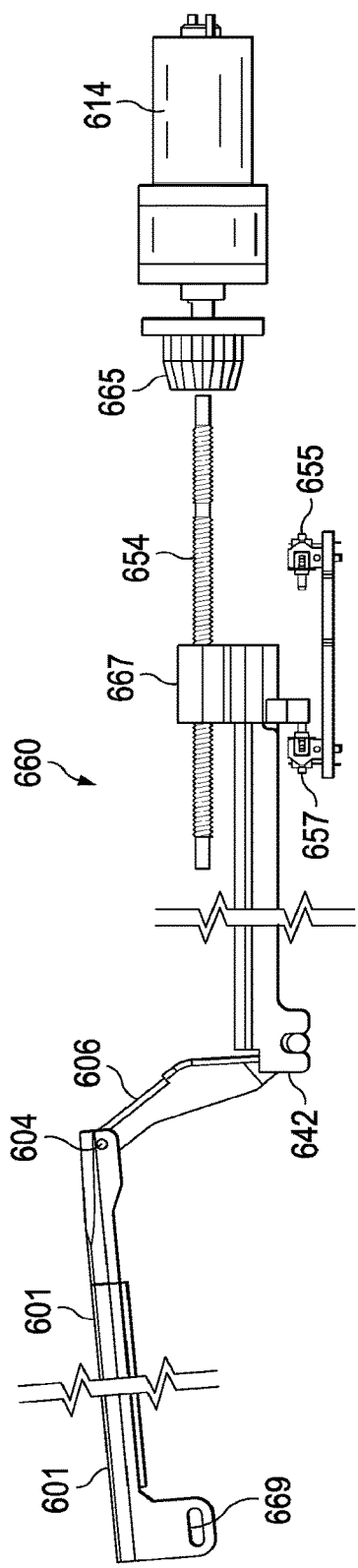
FIG. 21 is a sectioned side view of a blade assembly and a drive assembly for a stapling device according to an alternate embodiment.

FIG. 21 is a side view of a drive assembly 660 for opening and closing an anvil assembly 601 according to an alternate embodiment. Anvil assembly 601 can be moveably coupled with a master link 606, where the master link 606 can be pivotally coupled with a distal end of a platform 642.

In the illustrated embodiment, the anvil assembly 601 can include a distal slot 669 that can engage a pin (not shown) positioned at the distal end of the anvil assembly 601 to allow for movement of the pin within the distal slot 669 to facilitate opening and closing of the drive assembly 660. The proximal end of the anvil assembly 601 can include a fixed pin 604 that can pivotally couple the anvil assembly 601 and the master link 606. A proximal end of the platform 642 can include a drive nut 667 that can threadedly engage a drive screw 654. The drive nut 667 and the drive screw 654 can be coupled such that rotation of the drive screw 654 in a first direction urges the drive nut 667 proximally and rotation of the drive screw 654 in a second direction urges the drive nut 667 distally. A proximal end of the drive screw 654 can be coupled with a second motor gear 665 that is rotationally coupled with a first electric motor 614. During operation, the first electric motor 614 can rotate the drive screw 654 clockwise or counterclockwise to open and close the anvil assembly 601, respectively.

Still referring to FIG. 21, the drive assembly 660 can include a distal limit switch 657 and a proximal limit switch 655. When the anvil assembly 601 is in the fully open position, the drive nut 667 can be in its distal-most position such that it contacts the distal limit switch 657 to interrupt power to the first electric motor 614. When the anvil assembly 601 is in the fully closed position, the drive nut 667 can be in its proximal-most position such that it contacts the proximal limit switch 655 to interrupt power to the first electric motor 614.

Figure 22:
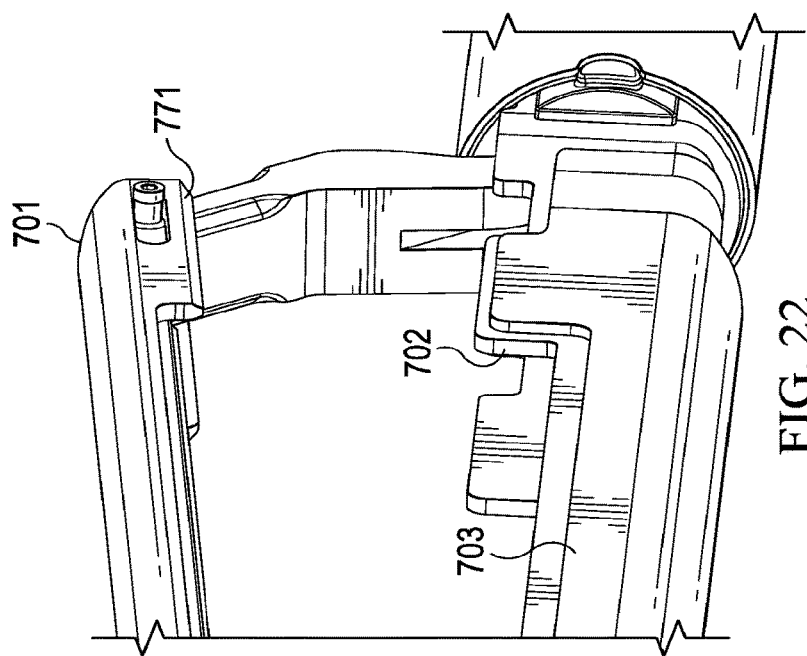
FIG. 22 is a partial perspective view of an anvil assembly having an anvil chamfer according to one embodiment.

During closure of an end effector, the anvil may interfere with the cartridge when closing on tissue because of the anvil's ability to rotate or deflect slightly relative to the longitudinal axis from tissue loads. FIG. 22 is a perspective view of a distal portion of an anvil frame 701 according to one embodiment. The anvil frame 701 can include a bevel feature, such as an anvil chamfer 771, that can guide the anvil frame into a channel 702 in a cartridge assembly 703 to help ensure alignment during closure. Tissue between the jaws may be thicker on one side than the other of the end effector, where the anvil chamfer 771 may assist with alignment if non-uniform tissue causes slight miss-alignment before closing the jaws of the end effector. One or a plurality of bevels can act as a lead-in feature that can work to align the end effector to help ensure that staples are properly deployed in varying tissue thicknesses.

Figure 23:
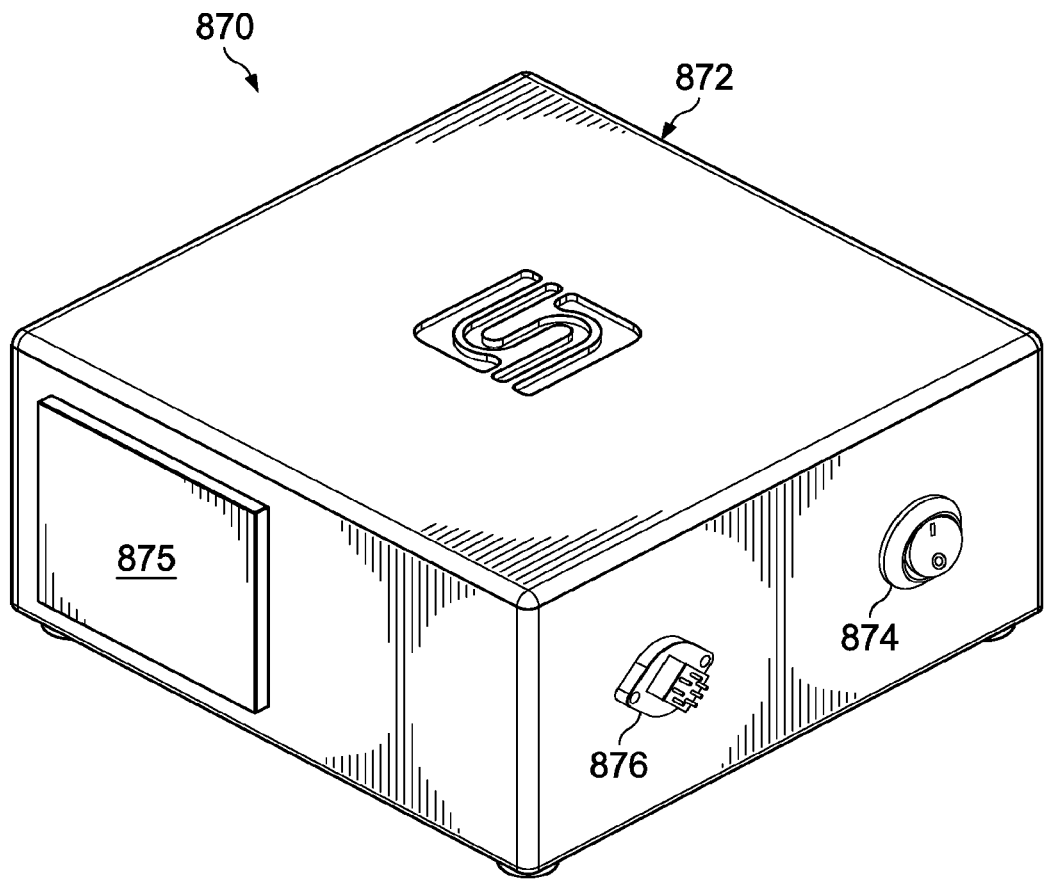
FIG. 23 is a perspective view of a motor controller according to one embodiment.

FIG. 23 is a perspective view of a motor controller 870 according to one embodiment. The motor controller 870 can include a controller housing 872 having an on/off switch 874, a display 875 and a device cable connector 876. The on/off switch 874 may provide for wall power, such as 110 Volt or 220 Volt AC power from a wall outlet, or may provide for battery power to the motor controller 870. The device cable connector 876 may connect multiple wires from the motor assembly of a stapling device to the motor controller 870. For example, the device cable connector 876 may provide positive and negative voltage wires to a first electric motor (e.g. first electric motor 335 shown in FIG. 13), positive and negative voltage wires to a second electric motor 337 (e.g., second electric motor 337 shown in FIG. 13), wires to a trigger (e.g., trigger 304 shown in FIG. 12), positive and negative sense wires to each of a firing complete limit switch 368 (FIG. 15), a proximal limit switch 555 (FIG. 20) and a distal limit switch 557 (FIG. 20), as well as any other wires useful for an endocutter.

Figure 24:
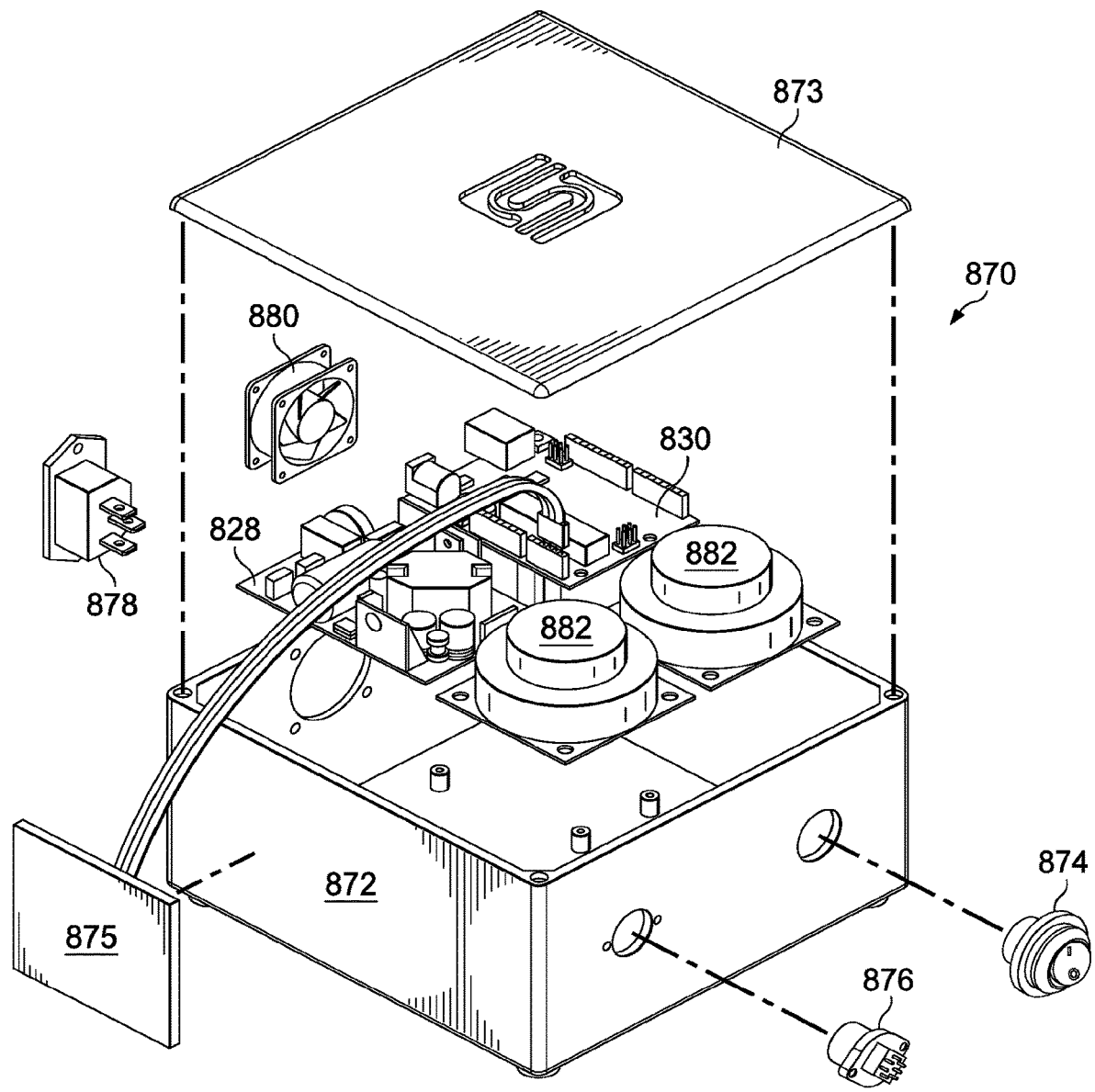
FIG. 24 is an exploded perspective view of the motor controller shown in FIG. 23.

FIG. 24 is an exploded perspective view of the motor controller 870 according to one embodiment. A lid 873, which can be part of the controller housing 872, can contain the components inside the controller housing 872. In the embodiment illustrated in FIG. 24, wall power can be brought into the controller housing 872 via an electrical inlet 878. A fan 880 may also be included to cool the interior of the controller housing 872. A pair of speakers 882 can be provided to inform the user of the stapling device conditions, such as, for example, jaws open, jaws closed, firing complete, ready to fire or other useful information. The display 875 can be used to provide visual directions, data, error conditions, instrument identification, or other useful data.

A motor controller board 828 can provide electrical power to the first electric motor 335 (FIG. 13) or the second electric motor 337 (FIG. 13) when appropriate. The motor controller board 828 can be directed by a processor board 830 to turn on or off the first electric motor 335 or the second electric motor 337. The processor board 830 can contain a processor, such as an ARM processor or other processor, useful in controlling a stapling device. For example, the processor board 830 can contain software that reads the condition of the limit switches 555, 557, 368 (FIGS. 15 and 20) and the trigger 304 (FIG. 12) and can control the motor controller board 828 to, for example, open and close the jaws, fire the system, or perform other useful functions.

In one example embodiment, the ARM processor can be used to communicate with an endocutter (for example, stapling device 100 shown in FIGS. 2A and 2B). For example, the stapling device 100 may include an EEPROM or other memory retaining device that can be encoded with a serial number during manufacturing. The memory can be used to provide information to the motor controller. For example, the processor can be capable of measuring and recording opening and closing motor amperage during activation on the manufacturing line; firing motor amperage during activation on the manufacturing line; opening and closing motor amperage in clinical use; firing motor amperage during activation in clinical use, or other data useful to the manufacturer or operator. This data can also be relayed to the motor controller 870 and stored. Such information can also be displayed during firing to the user by way of a connection of the motor controller 870 to a screen or display that can be incorporated into the stapling device 100, in the motor controller 870, or the data may be transmittable to a monitor used by a laparoscopic camera in a minimally invasive procedure.

Figure 25:
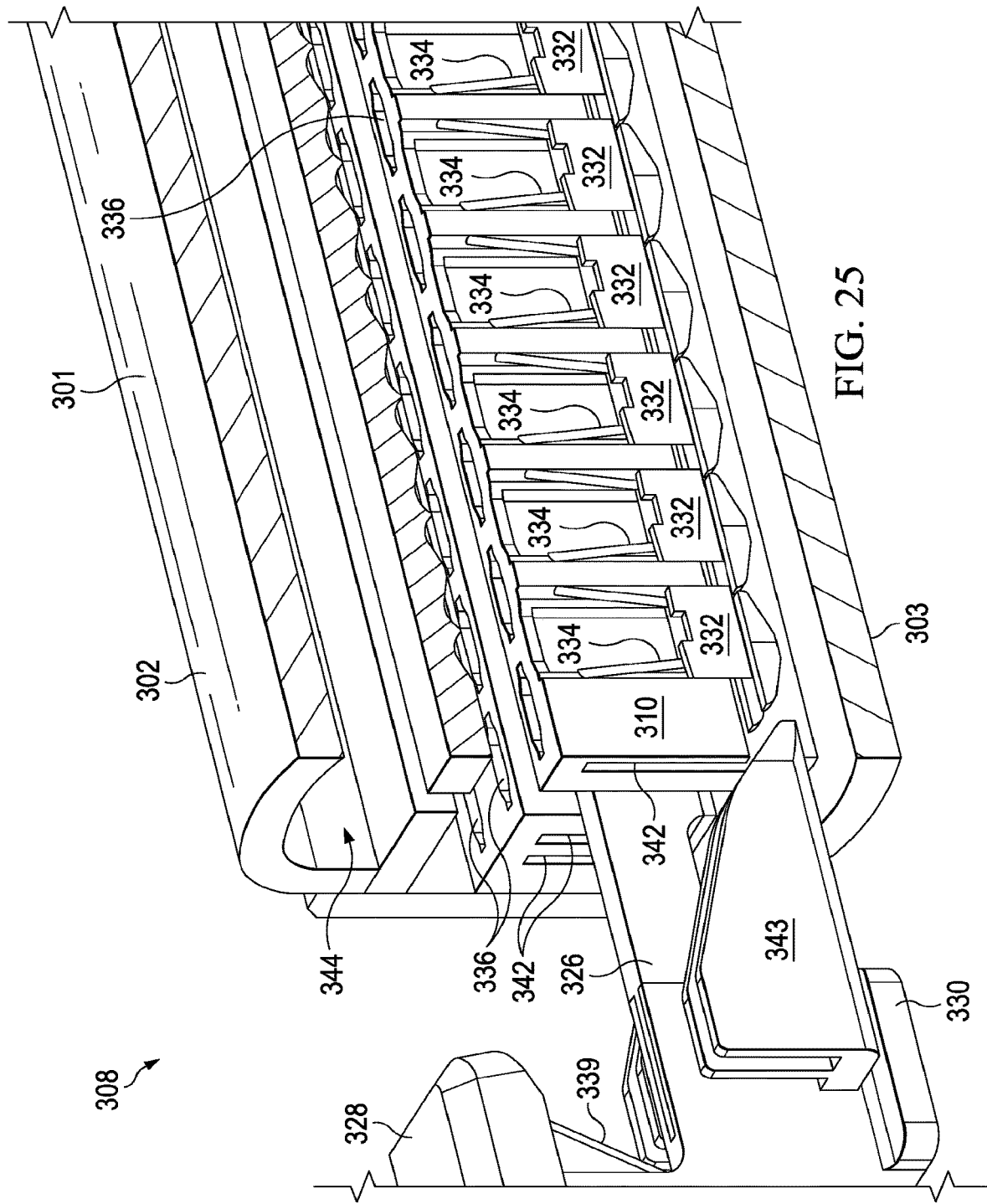
FIG. 25 is a partial cross-sectional perspective view of an end effector for a stapling device showing a blade assembly in relationship with a cartridge assembly having a plurality of drivers and staples.

FIG. 25 depicts a sectioned perspective view of a portion of the end effector 321 of the stapling device 300 shown in FIG. 11. A plurality of staple drivers 332 can be positioned in a cartridge 310 beneath a plurality of staples 334 in a plurality of staple pockets 336. The anvil frame 302 can include an anvil channel 344 that can accept a top portion 328 of blade 307. A staple driver ramp 343 can slide or otherwise move past a plurality of driver ramp slots 342. As the stapling device 300 is fired, the staple driver ramp 343 can engage the staple drivers 332 to drive the staples 334 into the anvil assembly 301. Behind each staple formed, the cutting edge 339 of the blade 307 can transect the tissue retained between the anvil assembly 301 and the cartridge assembly 303. Staple driver 332 heights can range from 1.5 mm to 4.5 mm, for example, and staple 334 lengths can range from 3.0 mm to 5.0 mm, for example. In certain embodiments, relatively tall drivers and short staples can be used for thin tissue and relatively short drivers can be used with long staples for thick tissue.

FIG. 26A is a cross-sectional side view of an end effector 321 of a stapling device 300 according to one embodiment. In the illustrated embodiment, an anvil plate 312 is flat and a cartridge 310 includes three staple driver 332 heights in sections 390, 391, and 392, that are sized to drive equal length staples 334. Providing section 390 (e.g., 2.2 mm driver height to form a 1.2 mm formed staple), section 391 (e.g., 2.7 mm driver height to form a 1.7 mm formed staple), and section 392 (e.g., 3.2 mm driver height to form a 2.2 mm formed staple) can allow for variable tissue thickness within the stapling device 300 during use. A taller driver height can create a staple through a thinner tissue thickness while a shorter driver height can provide a staple appropriate for thicker tissue. The cartridge 310 clamping surface can be angled relative to the anvil, such as from 0.1 degrees to 0.35 degrees, or 0.25 degrees, to provide uniform compression on the stomach, which has non-uniform tissue thickness.

FIG. 26B is a cross-sectional side view of the end effector 321 assembly of the stapling device 300 according to an alternate embodiment. In the illustrated version, the anvil plate 312 is flat and the cartridge 310 can include three staple driver 332 heights in sections 390, 391, and 392 that can drive three or more different length staples 334.

FIG. 26C is a cross-sectional side view of the end effector 321 of the stapling device 300 according to an alternate embodiment. In the illustrated version, the anvil plate 312 can be angled and the cartridge 310 can include identical staple driver 332 heights. In one embodiment, the cartridge 310 can include two different staple 334 lengths, where longer leg length staples (e.g., 4.4 mm) can be provided in a proximal portion of the cartridge 310 and shorter leg length staples (e.g., 3.8 mm) can be provided in a distal portion of the cartridge 310. In another embodiment, equal length staples can used along the entire length of the cartridge 310. In other embodiments, different staple lengths can be used in different rows or within a row at different locations along the length of the stapling device 300 to accommodate tissue thickness. Row to row variations can account for variation in tissue thickness on a patient-to-patient basis. Changing staple height within a row can account for the change in tissue thickness that can occur from one end of the stomach to the other. Providing an anvil plate 312 that is angled may be advantageous when stapling different thickness tissue to provide uniform tissue compression from the distal-most portion to the proximal-most portion of the cartridge 310 as the stapling device 300 is fired.

FIG. 26D is a cross-sectional side view of the end effector 321 of the stapling device 300 according to an alternate embodiment. In the illustrated embodiment, the anvil plate 312 is angled and the cartridge 310 includes a single staple driver 332 height to drive variable length staples 334. Any suitable number of different staple heights can be combined with the anvil plate 312 having a slope to provide desirable tissue compression and a staple line with high integrity. For example, as illustrated in FIG. 26D, the cartridge can include three different staple heights positioned along thirds of the cartridge 310.

FIG. 26E is a cross-sectional side view of the end effector 321 of the stapling device 300 according to an alternate embodiment. In the illustrated version, the anvil plate 312 is angled and the cartridge 310 can include staples having a uniform length. Any suitable combination of anvil plate angle, driver height, and staple heights is contemplated.

Figure 27:
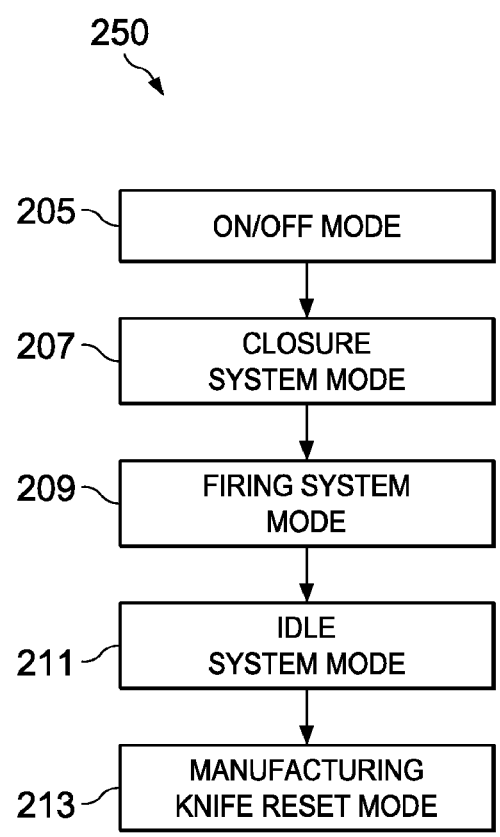
FIG. 27 is a flow chart depicting a method of operating a stapling device according to one embodiment.

FIG. 27 depicts a Method 250 of operating the end-effector portion of an endocutter (for example, stapling device 300) according to one embodiment. Method 251 may provide for safe and effective activation and use of the stapling device. Steps illustrated in FIG. 27 may be implemented in software on the processor board 830 (FIG. 24), in firmware, using a programmable gate array, or by other suitable methods for implementing logic control. The Method 251 includes an On/Off Mode 205, a Closure System Mode 207, a Firing System Mode 209, an Idle System Mode 211 and a Manufacturing Knife Reset Mode 213.

The On/Off Mode 205 can include delivering or eliminating power to the stapling device 100. The Closure System Mode 207 can provide for opening and closing of the end effector, jaws, or anvil and/or anvil and cartridge of a stapling device to provide for placement and adjustment of the endocutter on tissue. The Firing System Mode 209 can include safety and detection steps to provide for complete and effective firing of the staples. The Idle System Mode 211 can communicate function and options to the user, as well as waiting for user direction. For example, the Idle System Mode 211 can include use of a programmable memory, such as an EEPROM provided in the connector or handle that communicates information about the instrument to the controller. The Manufacturing Knife Reset Mode 213 may be useful during the testing and manufacturing of an endocutter to verify functionality during manufacturing and to position components properly for use.

The Firing System Mode 209 can include feedback to the operator regarding exceeding limits, such as compression limits, motor drive limits, tissue thickness limits or other limits useful to the operator. For example, motor current may be monitored by the controller, and when a predetermined motor current level is reached, the controller may provide feedback to the operator that the motor is reaching its load limit such that the operator can make a decision to alter the procedure or perform some other action.

In one embodiment, an endocutter or stapling device system in accordance with embodiments described herein may have a unique serial number or other identifier to allow the operator to record the particular serial number of the instrument used in a patient's record. When an instrument is plugged into the controller, such as motor controller 870, the controller may communicate with the memory and provide the serial number on a display of the controller. The memory may also be used to record information regarding the use of the instrument. For example, an event log may be recorded into the memory from the controller that records motor load, number of openings or closings of the instrument, number of firings of the instrument, error codes or other useful information onto the memory for later review.

Figure 28:
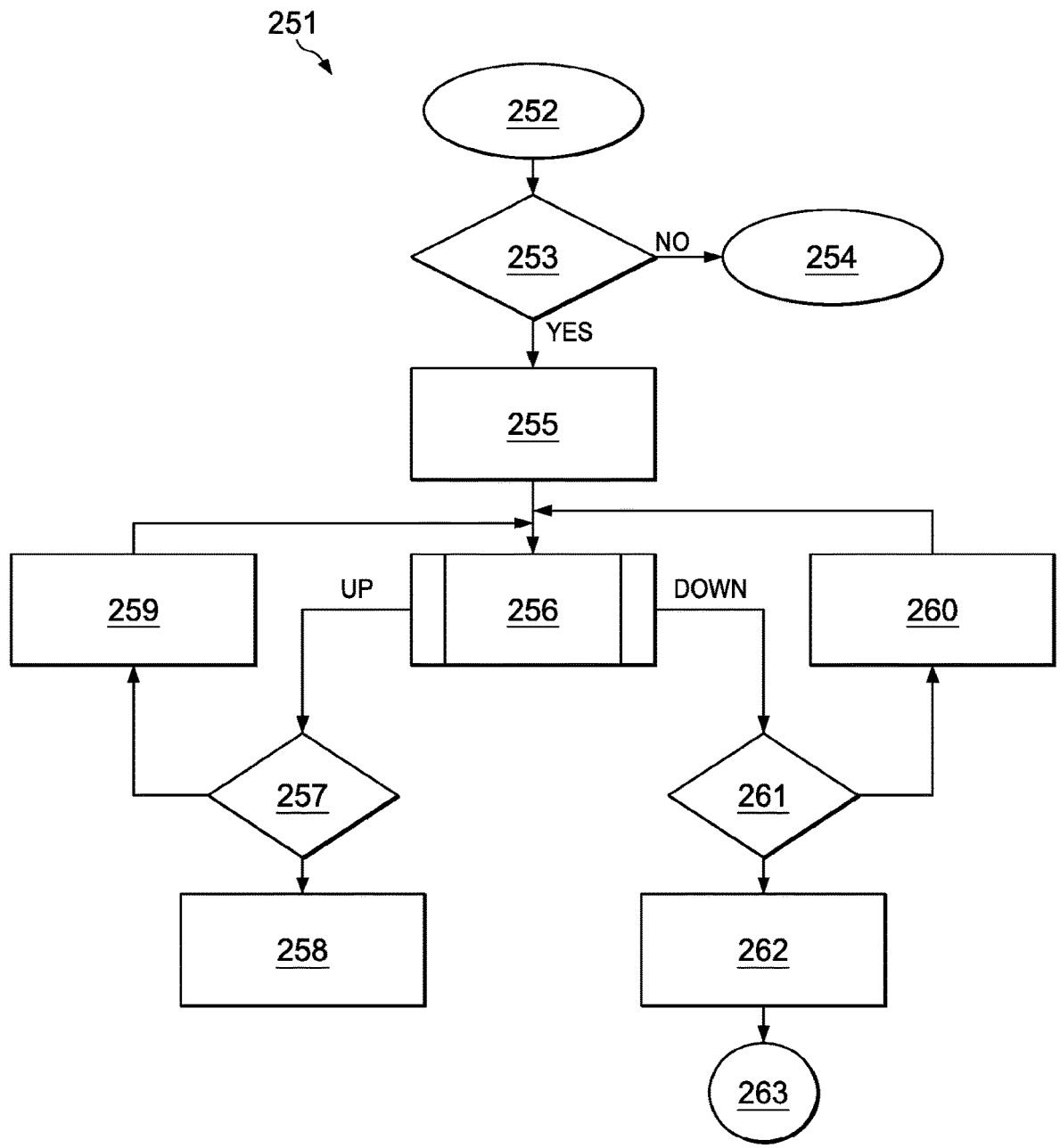
FIG. 28 is a partial flow chart depicting a method of operating a stapling device according to one embodiment.

FIG. 28 is a flow chart illustrating a Method 251 according to one embodiment. Method 251 can include a System Ready State 252 leading to a Closure Switch Active/All Other Switches Inactive Decision 253. Switches may include, for example, mode button 324, proximal limit switch 555, distal limit switch 557, or other useful switches. If the closure switch is active and any other switch is also active, then the system can enter an Error State 254. If no switches other than the closure open switch are active, then the system can enter a Closure System Mode 255. From the Closure System Mode 255, the Method 251 can then perform a Trigger Read 256, and determines whether the trigger is in a trigger up or trigger down state. If the Trigger Read 256 returns a trigger up condition, a Closure-Open Switch Activated Decision 257 can occur. If the Closure-Open Switch Activated Decision 257 is NO, a Motor Opens Device Condition 259 can occur and then another Trigger Read 256 can occur. If the Closure-Open Switch Activated Decision 257 is YES, then a Device Open Condition 258 can occur.

If, during a Trigger Read 256, a trigger down condition is detected, then a Closure Closed Switch Activated Decision 261 can be made. If the Closure Closed Switch Activated Decision 261 is NO, then a Motor Closes Device 260 condition can occur, and another Trigger Read 256 can follow. If the Closure Closed Switch Activated Decision 261 is YES, then a Device Closed Condition 262 can occur. Many conditions, such as, for example, the Device Closed Condition 262, can provide feedback to the operator regarding the device, such as by blinking an LED light, providing an audible sound, or other feedback type. For example, audio files may be created and provided at times during the Method 251 to provide information to the user regarding system states, conditions, errors, or functionality of the stapling device 100. The Method 251 in FIG. 25 can continue at Link 263 to FIG. 29.

Figure 29:
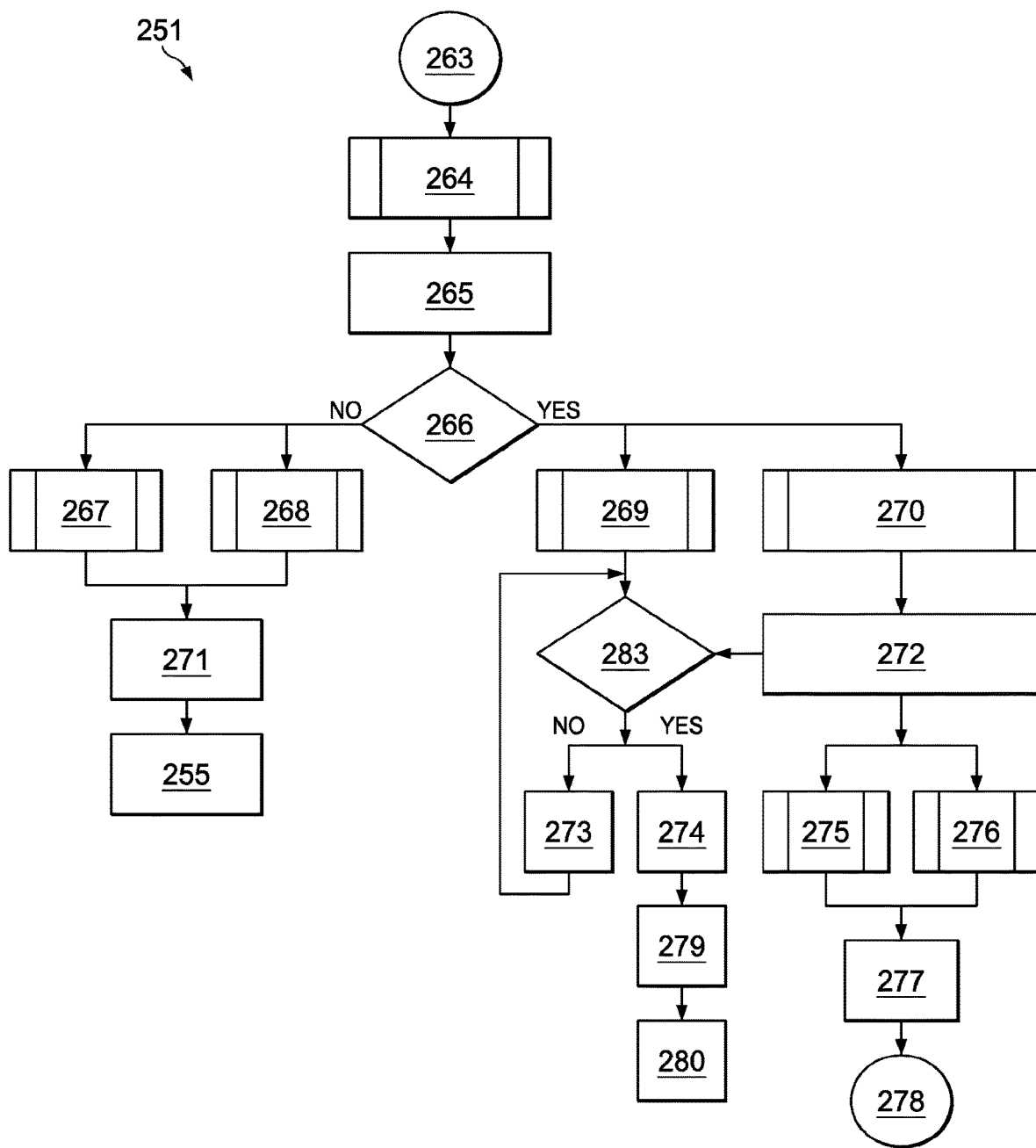
FIG. 29 is a partial flow chart depicting the method of operating a stapling device continuing the method of FIG. 28.

FIG. 29 is a flow chart illustrating the Method 251, starting at the Link 263 that links the portion of the Method 251 from FIG. 28 to the portion of the Method 251 illustrated in FIG. 29. When the Method 251 is in the Device Closed Condition 262, the Method 251 can utilize a Safety Switch 264 to make sure that the operator intends to fire the endocutter before a Firing System Mode 265 is enabled. A suitable Safety Switch 264 may be, for example, mode button 324 shown in FIG. 11. If the Firing System Mode 265 is enabled, then a Firing Started Decision 266 can be made. If the Firing Started Decision 266 is NO, then both a Safety Switch 268 active condition and a Trigger Up 267 condition are both met before a Closure System Mode 271 can be entered. If the Firing Started Decision 266 is YES, then a Trigger Down Condition 269 can precede a Firing Limit Switch Activated Decision 283. If the Firing Started Decision 266 is YES, then a Trigger Down Double-Click 270 can precede an Activate Firing Motor Condition 272. During the Activate Firing Motor Condition 272, the endocutter can fire and resect tissue until a Firing Limit Switch Activated Decision 283 determines that the firing limit switch is active.

If the Firing Limit Switch Activated Decision 283 is YES, then a Firing Motor Stops Condition 274 can be entered, the firing motor stops, and the Method 251 can enter a Firing Completion Mode 279 and then enter an Idle System Mode 280. If the Firing Limit Switch Activated Decision 283 is NO then Firing Motor Continues Condition 273 can occur until the firing limit switch activates, such as, for example, proximal limit switch 555. The Idle System Mode 280 is further described below with reference to FIG. 30.

Figure 30:
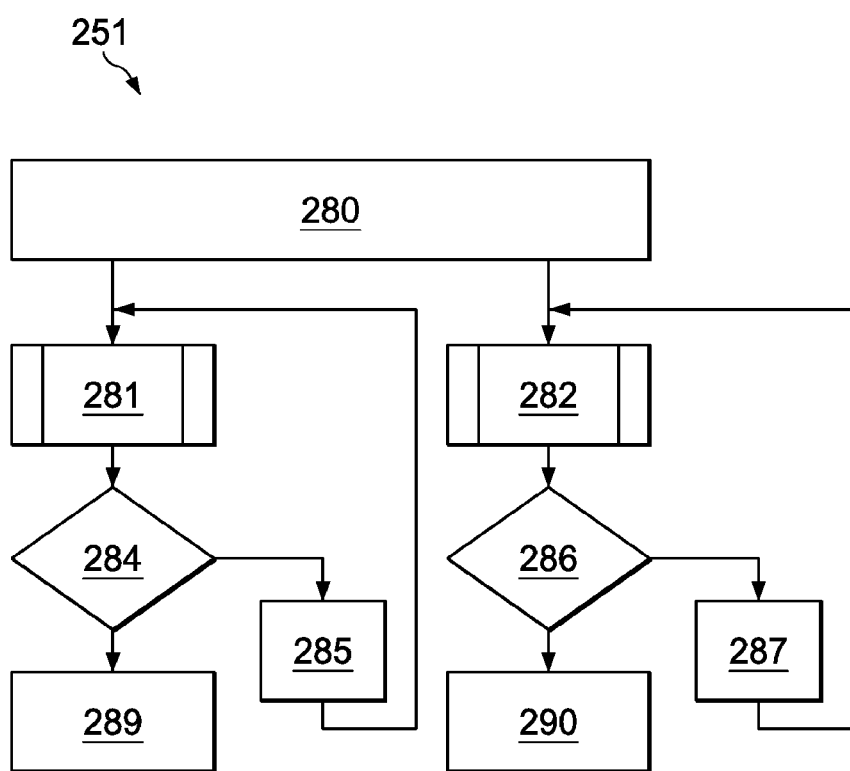
FIG. 30 is a partial flow chart depicting the method of operating a stapling device continuing the method of FIG. 29.

FIG. 30 is a flow chart illustrating the Method 251, beginning at the Idle System Mode 280. The system can idle until a Trigger Up Condition 281 or a Trigger Down Condition 282 occurs. A Trigger Up Condition 281 can prompt a Closure-Open Switch Activated Decision 284. If the Closure-Open Switch Activated Decision 284 is YES, the closure motor is stopped and a Device Open Condition 289 can occur. If the Closure-Open Switch Activated Decision 284 is NO, then the motor can continue to open the endocutter until the trigger is released or the closure open switch is activated. A Trigger Down Condition 282 can prompt a Closure-Closed Switch Activated Decision 286. If the Closure-Closed Switch Activated Decision 286 is YES, the losure motor can be stopped and a Device Closed Condition 290 can occur. If the Closure-Closed Switch Activated Decision 286 is NO, then the motor can continue to close the endocutter until the trigger is released or the closure closed switch is activated.

Figure 31:
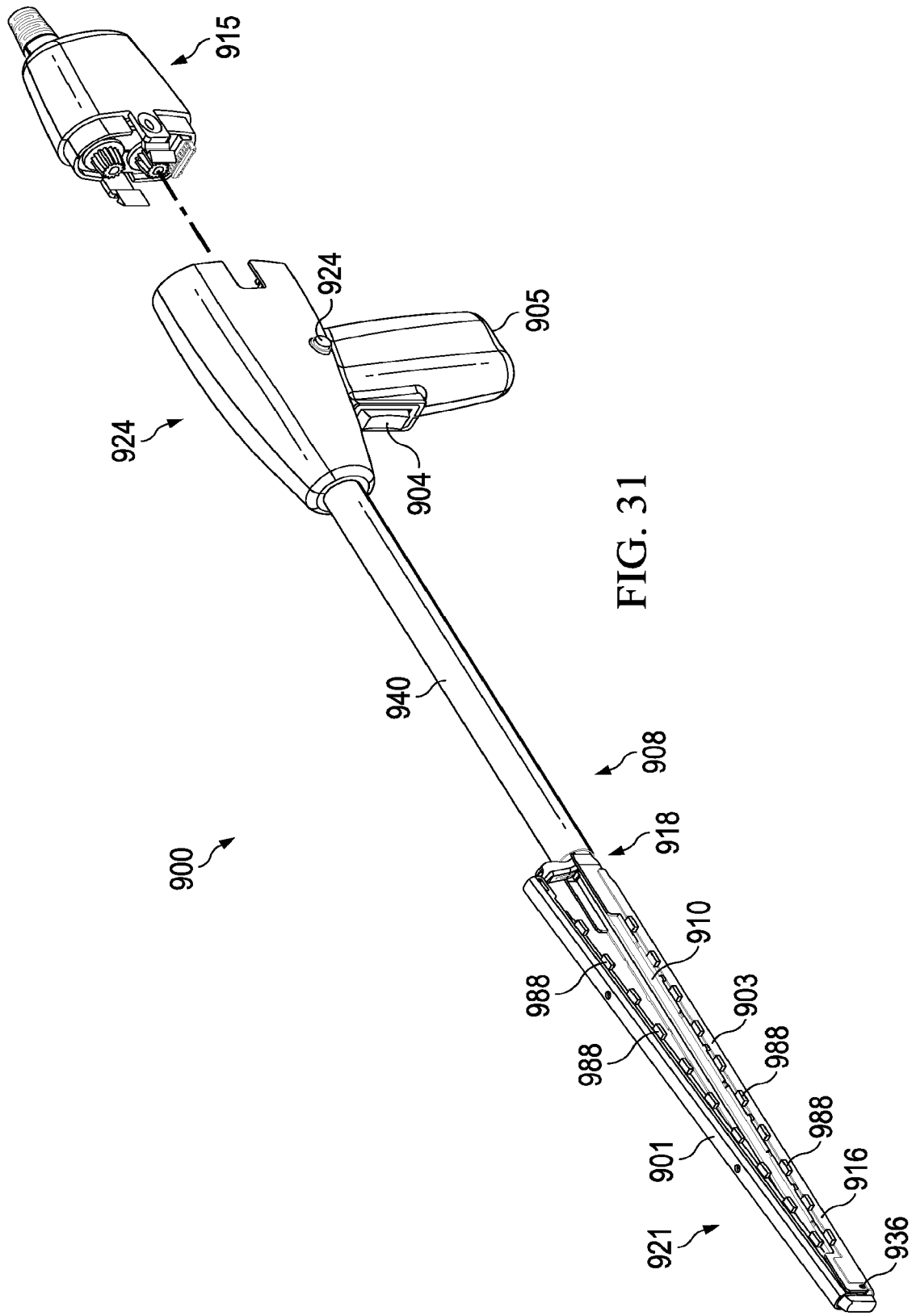
FIG. 31 depicts a perspective view of a stapling device, shown in an open position, having an end effector, an elongated tube, a handle portion, and a motor in accordance with an one embodiment.

FIG. 31 is a perspective view of a stapling device 900 in accordance with one embodiment. The stapling device 900 can include an endocutter 908 and a motor assembly 915. The endocutter 908 can include an end effector 921 including an anvil assembly 901 and a cartridge assembly 903, or a first jaw and a second jaw respectively, for the clamping, stapling, and/or resection of tissue. The end effector 321 can be connected to a handle portion 923 via a support tube 940. The handle portion 923 can include a handle 905 including a trigger 904 for actuating the stapling device 900. The handle portion 923 can include a mode button 924 for switching between operational modes. For example, in a first mode, the trigger 904 can be pressed upwards to open the jaws or pressed downwards to close the jaws. After the jaws are closed, the mode button 924 can be depressed, changing the trigger 904 function from and open/closed mode to a firing mode. When in firing mode, depressing the trigger 904 can fire the stapling device 900 to simultaneously form a staple line while cutting tissue between the staple line.

As illustrated in FIG. 31, the stapling device 900 can include a buttress assembly comprising, in part, a plurality of cord supports 988 positioned on the cartridge assembly 903 and the anvil assembly 901 to provide for the attachment of a buttress material 991 (FIG. 32) to the stapling device 900. The cord supports 988 may be useful for attaching the buttress material 991 before or during surgery. The buttress material 991 can be used to add support and purchase to the staple line to provide improved sealing to the cut tissue as the staples are formed. The buttress material 991 may be formed from absorbable or non-absorbable material for either temporary or permanent applications. The cord supports 988 can be used to hold the buttress material 991 on the stapling device 900 until after the staple line is formed, at which point a cord 387 (FIG. 32) can be released to allow the buttress material 991 to separate from the cord supports 988 and the stapling device 900. The cord supports 988 can be built into the anvil assembly 901 or cartridge assembly 903 such that the buttress material 991 can be attached to the stapling device 900 prior to or during a procedure by, for example, threading a suture material or cord 987 through loops 999 in the buttress material 991 and over or around the cord supports 988.

Figure 32:
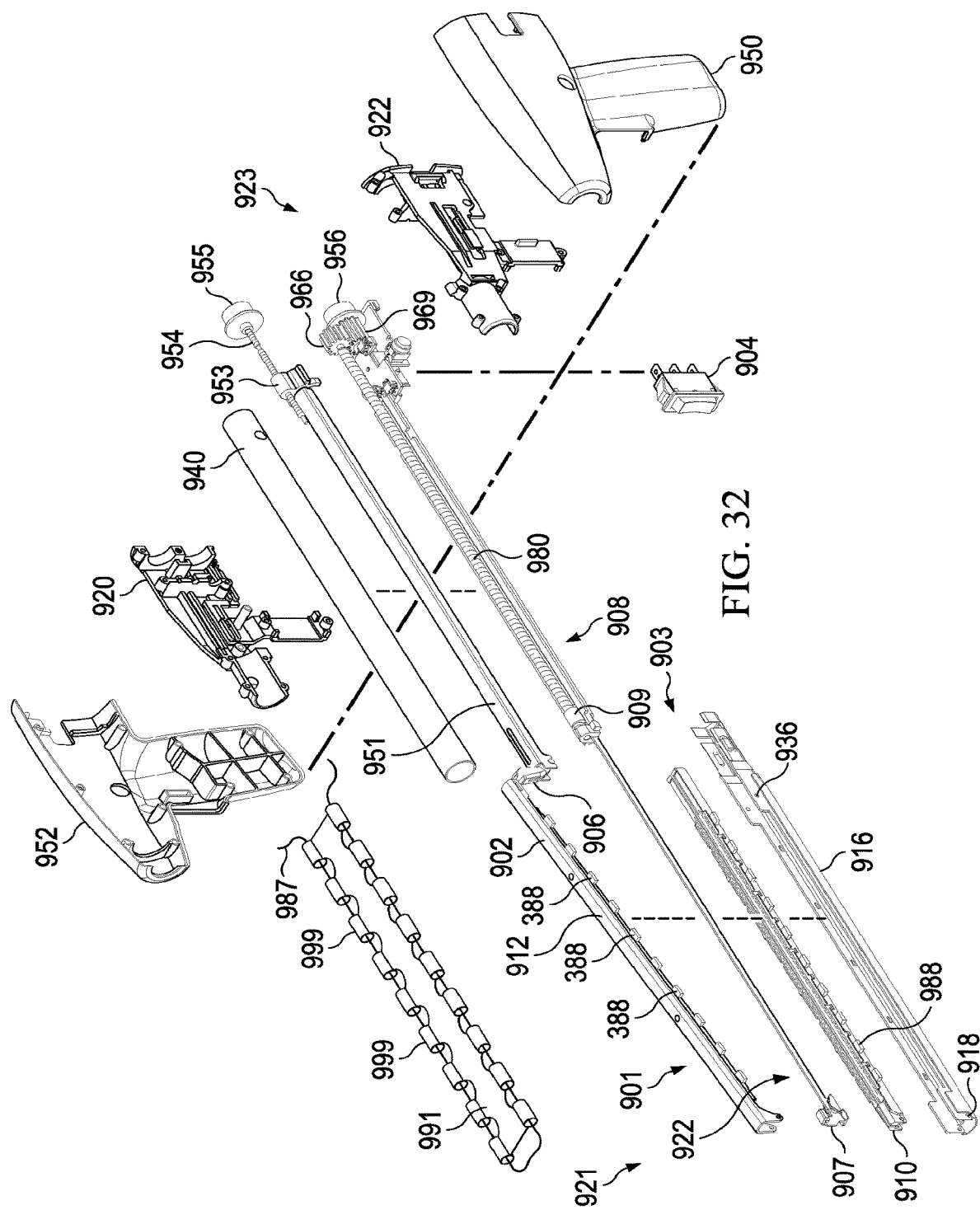
FIG. 32 depicts a partial exploded perspective view of the stapling device of FIG. 31 shown with a buttress.

FIG. 32 depicts an exploded perspective view of the stapling device 900 in accordance with one embodiment. The anvil assembly 901 can include an anvil frame 902 and an anvil plate 912. The cartridge assembly 903 can include a cartridge frame 916 and a cartridge 910. The cartridge 910 may be attached to the cartridge frame 916 by a first cartridge pin 936 at a first end and a second cartridge pin 918 at a second end, or alternately the cartridge 910 may be attached to the cartridge frame 916 via snap fit, gluing, or other attachment methods.

In the embodiment illustrated in FIG. 32, the cartridge frame 916 can be insertable at its proximal end into a support tube 940 to align and connect the end effector 921 of the stapling device 900 to a handle portion 923 of the stapling device 900. A blade assembly 922 can include a blade 907 coupled to a rotating member 980 via a nut 909.

The handle portion 923 can include a right handle half 920 and a left handle half 922 that can be held together in a clamshell-like fashion. The right handle half 920 and left handle half 922 can be joined by, for example, ultrasonic welding, glued, screwed together with self-tapping screws, gripper pins or press-fit pins into holes molded into the handle or other assembly method. A left handle shell 950 and a right handle shell 952 can be used to provide a pleasing aesthetic look to the exterior of the handle portion 923 by covering the left handle half 922 and the right handle half 920.

A drive screw 954 can be used to drive a control arm 951 via a control arm nut 953. The drive screw 954 can be connected to a drive gear coupler 955 that can engage the motor assembly 915 (FIG. 31). The rotating member 980 is illustrated as coupled to a drive gear coupler 956 via a first firing drive gear 966 and a second firing drive gear 969. The drive gear coupler 956 can be coupled with the motor assembly 915.

As illustrated in FIG. 32, the cord supports 988 can be attached to the cartridge 910, or to the cartridge frame 916 as illustrated in FIG. 31. The cord supports 388 can include lateral projections, hoops, tabs, hooks, loops, or other suitable structure to retain the buttress material 991. The buttress material 991 can have the cord 987 integrated into the buttress material 991 to provide support and to hold the buttress material 991 onto the cartridge 910. For example, the cord supports may be tubular shaped, having a "C" shaped cross-section (not shown), such that the cord supports are not completely closed. The open "C" shape can allow for the attachment of the buttress material to the end effector by pulling the cord over the tubular shape and allowing the cord to slip into the opening of the "C" to hold the buttress material in place. Cord supports 988 can be provided on the anvil frame 902 or on the anvil plate 112. The cord 987 can be, for example, suture material, wire cable, wire strand, individual wire, rope, monofilament, thread or other suitable material.

FIG. 33A is a side view of the stapling device 900 in accordance with one embodiment having an open end effector 921. The end effector 921 can include the anvil assembly 901, the cartridge assembly 903, and the master link 906. The end effector 921 is illustrated before installation of the buttress material 991. It will be appreciated that the buttress material 991 can be provided already attached to the end effector 921 from the supplier, or the buttress material 991 can be placed on the end effector 921, in the open position, during the surgical procedure. For example, the buttress material 991 can be provided in a sterile package and can be opened in the sterile field during the surgical procedure. The clinician can then apply the buttress material 991 to the anvil or cartridge with the stapling device 900 in the fully open position and thread or loop the cord 987 on or through the cord supports 988 to hold the buttress material 991 in place. Once the buttress material 991 has been attached to the end effector 921, as shown in FIG. 33A, the stapling device 900 can be closed such that the end effector 921 can fit through a trocar into the operative site.

FIGS. 34A and 34B illustrate the buttress material 991 shown with the cord 987 engaged with the plurality of loops 999. The apertures 984 defined by the buttress material 991 can be spaced between the loops 999 and can be sized and positioned to correspond with the cord supports 988 on the end effector 921. It will be appreciated that the buttress material 991 can have any suitable size and shape to engage with and selectively retain the cord 987 or any other suitable buttress material retention mechanism or structure. The cord 987 can be a single suture threaded through the loops 999, or the use of multiple cords or sutures to secure the buttress material is also contemplated.

Figure 36:
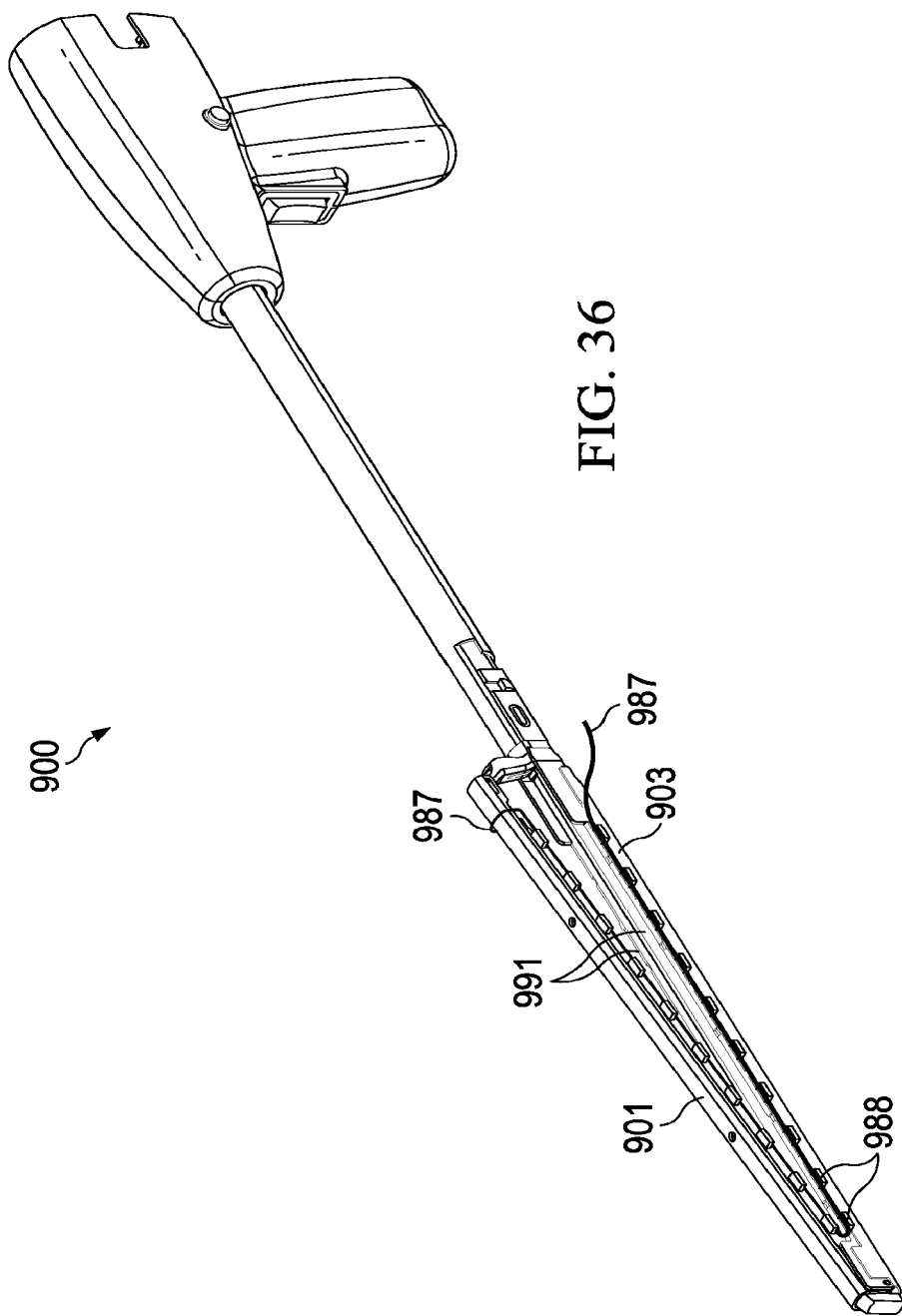
FIG. 36 depicts a perspective view of the stapling device of FIG. 31, shown with the buttress of FIG. 32 attached, according to one embodiment.

FIG. 35A illustrates the anvil assembly 901 shown with a plurality of cord supports 988 prior to attachment of the buttress material 991. FIG. 35B illustrates the anvil assembly 901 with the buttress material 991 attached to the cord supports 988 with the cord 987 according to one embodiment. FIG. 36 illustrates a perspective view of the stapling device 900 with the buttress material 991 attached to the anvil assembly 901 and the cartridge assembly 903 with the cord 987.

As illustrated in FIG. 37, the stapling device 1000 can include a buttress 1088 having an adhesive that can be positioned on the cartridge assembly 1003 and the anvil assembly 1001. The buttress 1088 can include a buttress material 1091 and one or a plurality of adhesive portions 1090 that can be used to couple the buttress material 1091 to the anvil assembly 1001 or cartridge assembly 1003. The buttress 1088 can be used to add support and purchase to the staple line to provide improved sealing to the transected tissue as the staples are formed. The buttress material 1091 can be formed from absorbable or non-absorbable material for either temporary or permanent applications. The adhesive portions 1090 can be used to hold the buttress material 1091 on the stapling device 1000 until after the staple line is formed, at which point the staple line can retain all or a portion of the buttress material 1091 on the tissue.

Figure 38A:
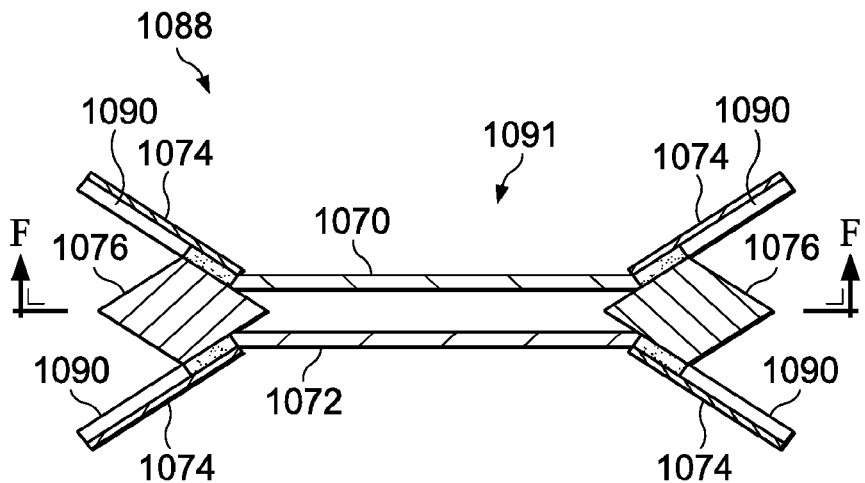
FIG. 38A is a cross-sectional view of the adhesive-type buttress, taken along section F-F, shown in FIG. 37.

In one embodiment, as shown in FIGS. 38A-38E, the buttress material 1091 can be two-ply such that it includes an anvil buttress portion 1070 and a cartridge buttress portion 1072. As shown in FIG. 38A, the buttress 1088 can include a pair of removable portions 1076 that can couple the anvil buttress portion 1070 to the cartridge buttress portion 1072 prior to use. The removable portions 1076 can be adhesively attached to the buttress 1088, or can be attached with frangible portions or the like.

Figure 38B:
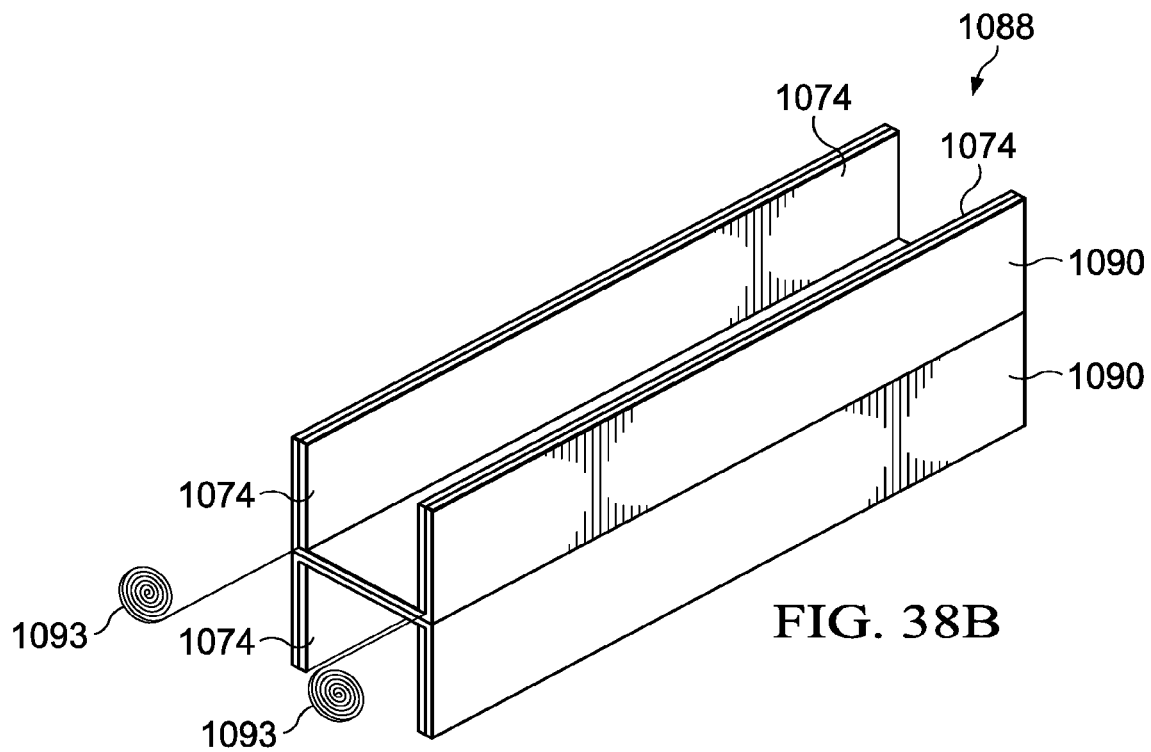
FIG. 38B is a perspective view of the adhesive-type buttress, shown in FIG. 37, with a removable portion removed.

In one embodiment, the removable portions 1076 are pliable such that by pushing laterally inward on each of the removable portions 1076 the adhesive portions 1090 can pivot radially inward to contact the sides of the end effector 1021 (see, for example, FIGS. 38B-38C). In one method of use, the buttress 1088 can be positioned in the end effector 1021, a backing material 1074 can be removed to expose the adhesive portions 1090, the removable portions 1076 can be urged inward such that the adhesive portions 1090 are adhesively coupled with the end effector 1021, and the removable portions 1076 can then be removed such that the anvil buttress portion 1070 is separated from the cartridge buttress portion 1072.

In an alternate embodiment, after the buttress 1088 has been placed in the end effector in the closed position, the removable portions 1076 can be removed to allow adhesive portions 1090 to flex such that each adhesive portion 1090 can engage a side of the end effector 1021 for attachment.

Figure 38E:
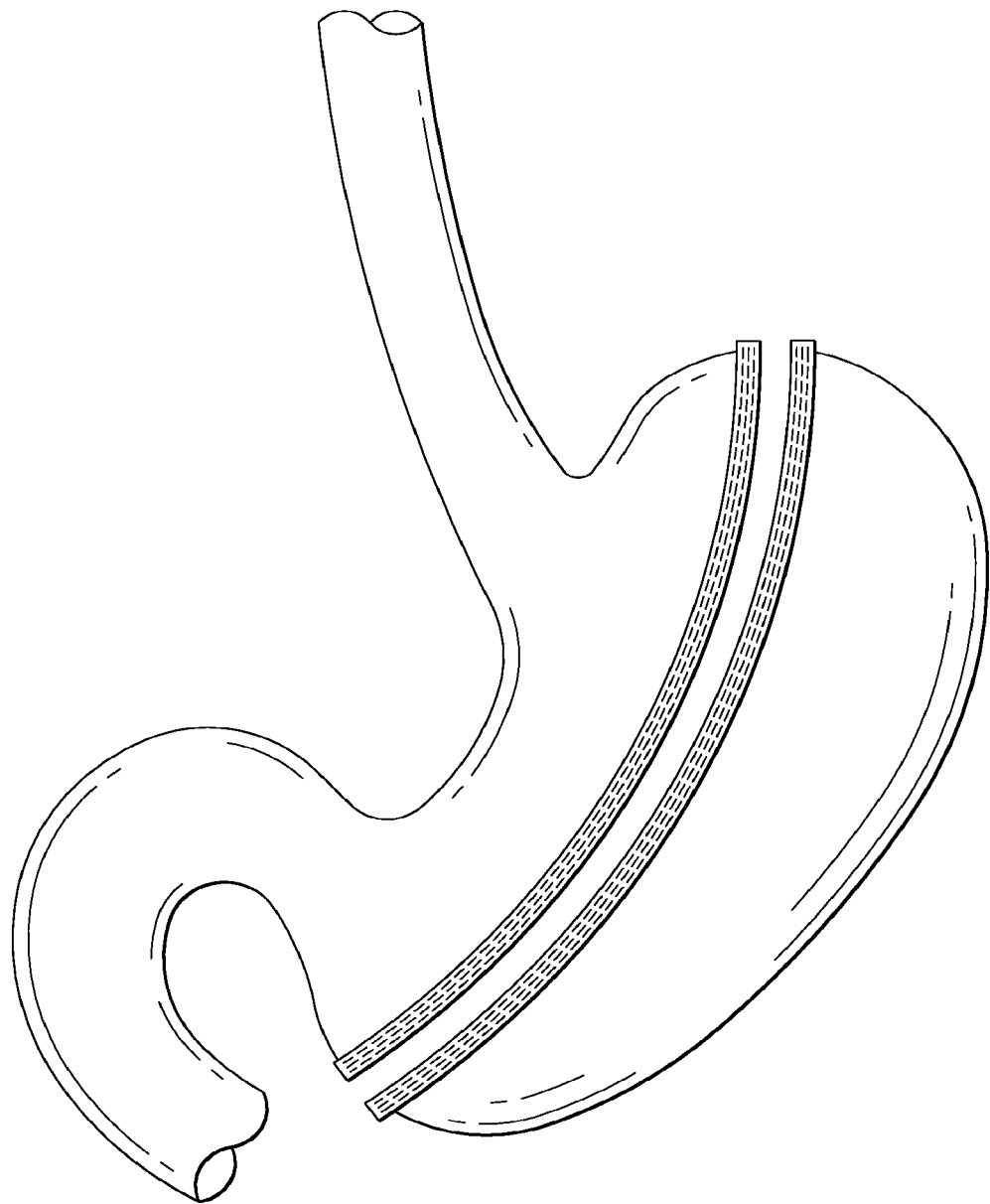
FIG. 38E depicts a front view of a stomach shown resected with a staple line, coupled with a buttress material, forming a sleeve gastrectomy.

Referring to FIGS. 38A-38C, the buttress material 1091 can include four adhesive portions 1090 that can flank the buttress material 1091. With reference to FIG. 38D, the anvil buttress portion 1070 and the cartridge buttress portion 1072 can be sized such that each covers all or a portion of an anvil face 1012 and a cartridge face 1014, respectively, of the end effector 1021. The adhesive portions 1090 can be sized such that each can be folded to adhere to the sides of the anvil assembly 1001 or the cartridge assembly 1003 as shown in FIG. 38D. Prior to use, each of the adhesive portions 1090 can include the backing material 1074. For ease of removal, the backing material 1074 can be coupled with one or more removal threads 1093 (FIG. 38B) that, when pulled, can remove the backing material 1074 from the adhesive portions 1090. As shown in FIG. 38E, when the stomach is resected, a portion of the staple line can form a sleeve gastrectomy in cooperation with the buttress material.

Varying pocket depth may improve the ability to achieve a minimum acceptable level of compression without over-compressing tissue. Varying pocket depth may also mitigate the risk associated with the malformation of staples which can occur when there is a tissue thickness and staple height mismatch.

Figure 39A:
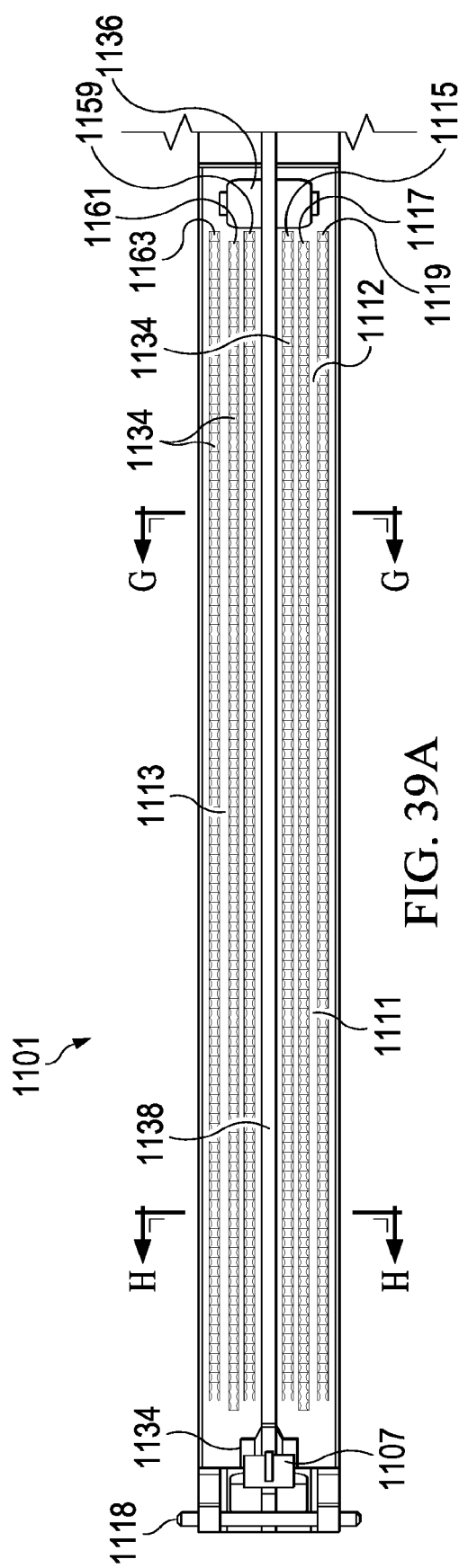
FIG. 39A is a bottom view of an anvil assembly for an end effector of a stapling device in accordance with one embodiment.

FIG. 39A is a bottom view of an anvil assembly 1101 in accordance with one embodiment. In FIG. 39A, an anvil plate 1112 is illustrated with six rows of anvil pockets including first pocket row 1115, second pocket row 1117, third pocket row 1119, fourth pocket row 1159, fifth pocket row 1161, and sixth pocket row 1163. The staple pockets 1134 in the anvil plate 1112 can be shaped to receive and shape the tips of staples as the staples are driven into the anvil plate 1112. When the staples engage with the anvil plate 1112, the tips of each staple can be directed until each has a substantially B-shaped configuration (see, for example, FIGS. 42A-42C). The staple pockets 1134 can be machined into the anvil plate 1112, eroded into the anvil plate 1112 using an EDM process, created using a precise electrochemical machining (PEM) process, formed using a sintering process, molded using a metal injection molding process, or otherwise manufactured.

The anvil plate 1112 can be divided into a left anvil half 1111 and a right anvil half 1113 separated by a knife channel 1138. It will be appreciated that any suitable number of pocket rows having any suitable size, shape, and orientation are contemplated. In the illustrated example of FIG. 39A, the first pocket row 1115 and the second pocket row 1117 are spaced more closely together than the third pocket row 1119. Similarly, the fourth pocket row 1159 and the fifth pocket row 1161 are spaced more closely together than the sixth pocket row 1163. It is understood that any spacing may be used between the rows, and that the spacing on the left anvil half 1111 may differ from the spacing on the right anvil half 1113. In the illustrated example, the pocket rows are shown having a staggered relationship, which may be beneficial in maintaining the integrity of the staple line. It is understood that any desirable stagger or spacing may be used with any suitable number of staple rows. In the illustrated embodiment, each of the staple rows is parallel to a longitudinal axis of the anvil assembly 1101, and extends from a proximal end to distal end of the anvil assembly 1101, but one or more rows may be offset and have any suitable length.

Spacing between rows of staples can be, for example, from 0.030 inches to 0.060 inches, or 0.044 inches. Staple rows can be staggered relative to each other in an overlapping fashion such that the middle of the staple in one row is between two staples in an adjacent row. A non-symmetrical stagger (not shown) of the staple rows on the left anvil half 1111 and the right anvil half 1113 may be useful in some procedures, such as in a sleeve gastrectomy procedure, where tissue is removed along one side of a cut and a gastric sleeve is formed on the other side of the cut. The integrity of the portion of the staple line along the newly formed sleeve may be more critical and, as such, may include additional staple rows, a different orientation of staples, or be otherwise configured. In one embodiment (not shown), one half of an anvil has three staple rows and the other half includes two staple rows.

Figure 39B:
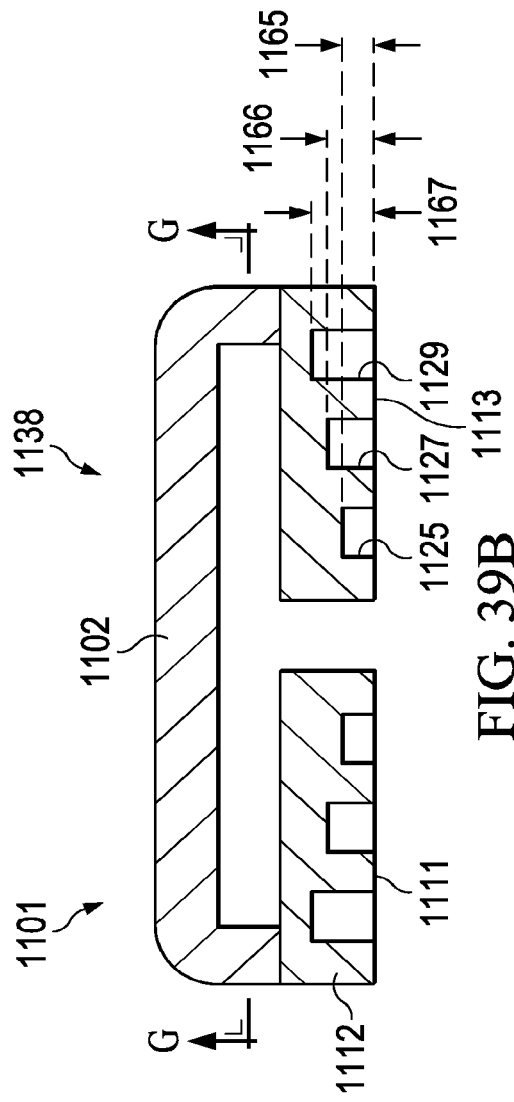
FIG. 39B is a cross-sectional view of the anvil assembly illustrated in FIG. 39A, taken along section G-G, in accordance with one embodiment.

FIG. 39B is a cross-sectional view of the anvil assembly 1101 illustrated in FIG. 39A at section G-G. As illustrated, each of the pocket rows, in addition to having variable sizing and position relative to other pocket rows, can include variable pocket depths that can result in different staple formation. For example, a first pocket 1125 from fourth pocket row 1159 can have a first depth 1165. A second pocket 1127 from fifth pocket row 1161 can have a second pocket depth 1166. A third pocket 1129 from sixth pocket row 1163 can have a third pocket depth 167. In the illustrated embodiment, the first pocket 1125 depth is shallower than the second pocket 1127 depth, and the second pocket 1127 depth is shallower than the third pocket 1129 depth. Varying the pocket depth by row may be advantageous because it can allow tissue farther from the knife channel 1138 to expand more than tissue closer to the knife channel 1138 when the procedure is complete. It should be understood, however, that any depth of the pockets and relationship between the rows of pockets is contemplated.

Figure 39C:
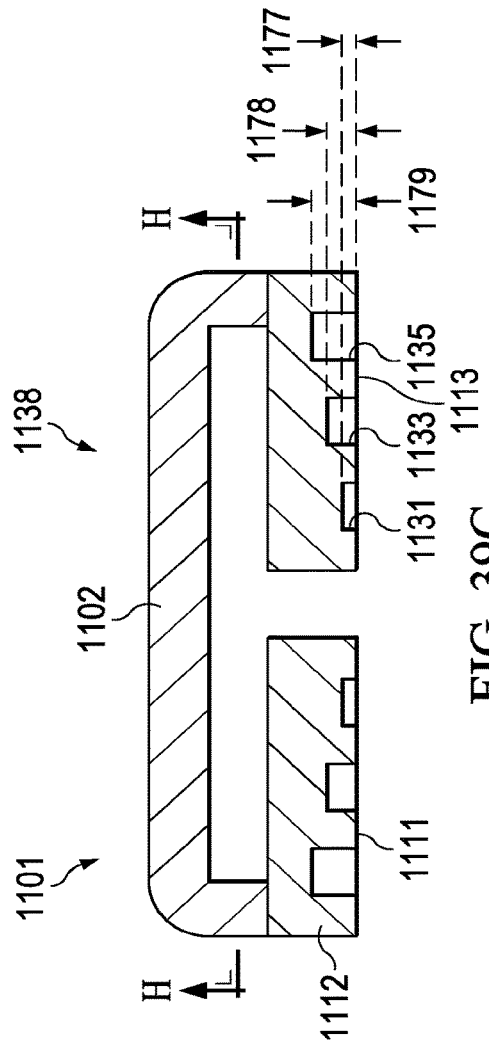
FIG. 39C is a cross-sectional view of the anvil assembly illustrated in FIG. 39A, taken along section H-H, in accordance with one embodiment.

FIG. 39C is a cross-sectional view of the anvil assembly 1101 illustrated in FIG. 35 at section H-H in accordance with one embodiment. As illustrated, the depths of the pockets associated with each row can also vary along the length of the anvil assembly 1101. As illustrated, a fourth pocket 1131 from fourth pocket row 1159 has a fourth pocket depth 1177, a fifth pocket 1133 from fifth pocket row 1161 has a fifth pocket depth 1178, and a sixth pocket 1135 from sixth pocket row 1163 has a sixth pocket depth 1179. In the illustrated embodiment, the fourth pocket 1131 depth is shallower than the fifth pocket 1133 depth, and the fifth pocket 1133 depth is shallower than the sixth pocket 1135 depth. Also, as illustrated the fourth pocket 1131 is shallower than the first pocket 1125, the fifth pocket 1133 is shallower than the second pocket 1127, and the sixth pocket 1135 is shallower than the third pocket 1129. A single staple row can include any desirable pocket depth to form staples of any suitable shape or size. Pocket size can vary from larger at the proximal end of the anvil assembly 1101 to smaller at the distal end of the anvil assembly 1101, or vice versa. It will be appreciated that differently sized staples can be used in accordance with various pocket depths and pocket rows to create a desirable tissue effect.

It may be advantageous to provide a stapling device with an anvil assembly 1101 that can accommodate a broad cross-section of the human population. In one example embodiment, the depth of the second pocket row 1117 and the fifth pocket row 1161 can have a depth that corresponds to the median thickness of the stomach for the derived human population. The first pocket row 1115 and the fourth pocket row 1159 can have a shallower depth that can correspond to the 25th percentile of stomach thickness for the human population. The third pocket row 1119 and the sixth pocket row 1163 can have a depth that can correspond to the 75th percentile of stomach thickness for the human population. Varying pocket depth in this way to provide varying staple height in the rows may eliminate cartridge selection issues such that a universally applicable cartridge can be provided. Varying pocket depth along the length or width of the staple line may account for variations in the human population. It will be appreciated that such embodiments can be combined with any suitable cartridge having any suitable size and shape of staples and any suitable shape and size of staple drivers.

Figure 40:
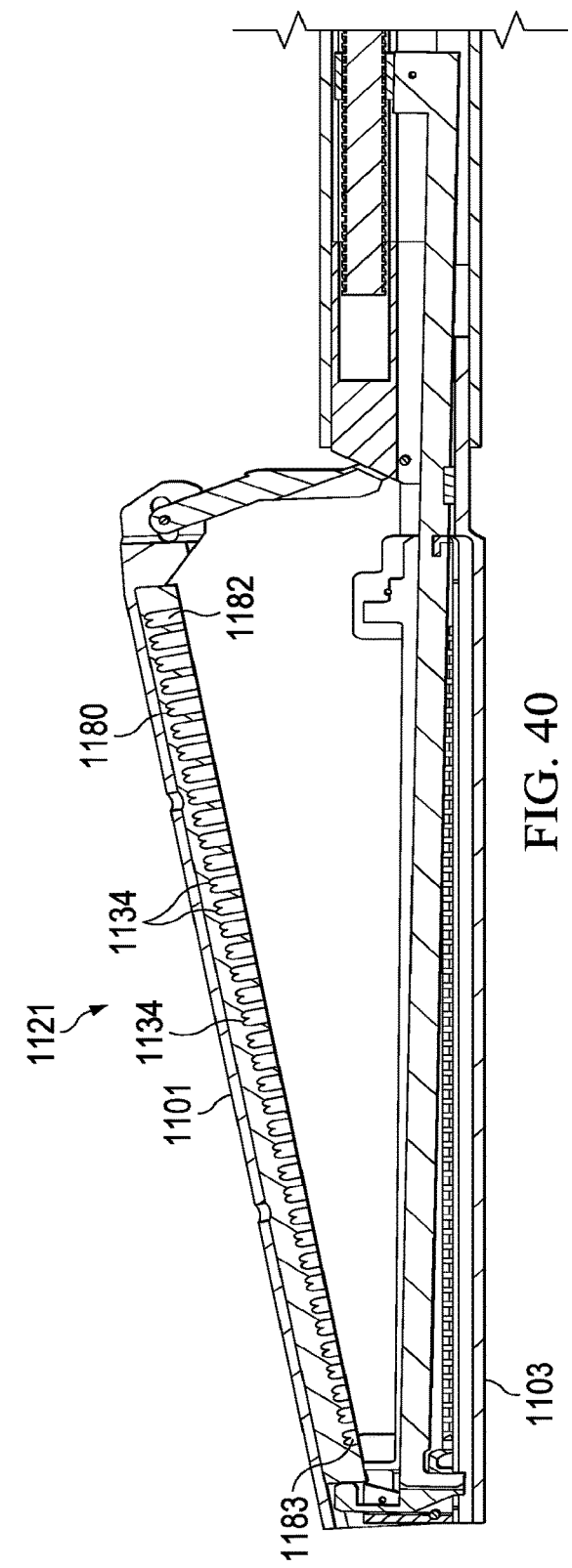
FIG. 40 is a side cross-sectional view of an end effector having an anvil plate with with varying pocket depths according to one embodiment.

FIG. 40 depicts a side cross-sectional view the end effector 1121 shown in an open position. In FIG. 40, a row 1180 of staple pockets 1134 is illustrated in sectioned view extending from a most proximal staple pocket 1182 to a most distal staple pocket 1183. The depths of the staple pockets 1134 can vary continuously in depth from the most proximal staple pocket 1182, the deepest pocket, to the most distal staple pocket 1183, the shallowest pocket. As disclosed previously, the depths may vary continuously along the length of the staple row or vary discretely at one or more points along the length of the anvil assembly 1101. It is contemplated that depths of the staple pockets 1134 may vary only along the length of the anvil assembly 1101, only axially across the width of the anvil assembly 1101, or both along the length and the width of anvil assembly 1101. It is further contemplated that the pocket depth variation along a row closer to the knife channel 1138 can vary at a different scale or rate than another row positioned farther from the knife channel 1138.

Figure 41:
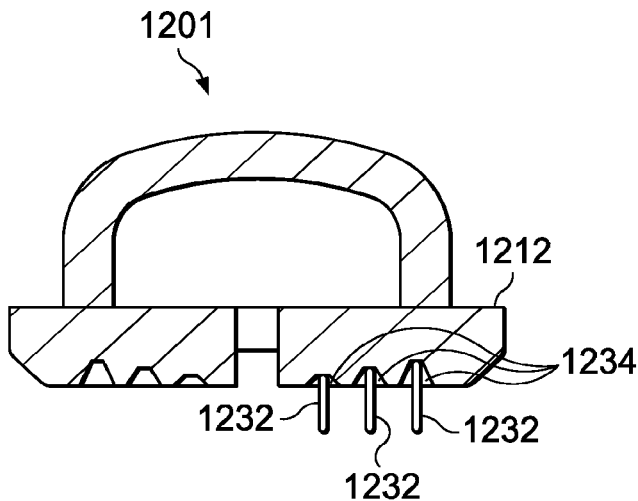
FIG. 41 is an axial cross-sectional view of an anvil assembly with an anvil plate, shown with a plurality of staples, in accordance with one embodiment.
Figure 42A:
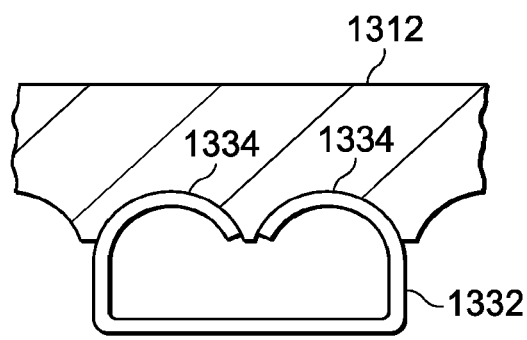
FIG. 42A is a side view of a staple formed by the anvil plate of FIG. 40.
Figure 42B:
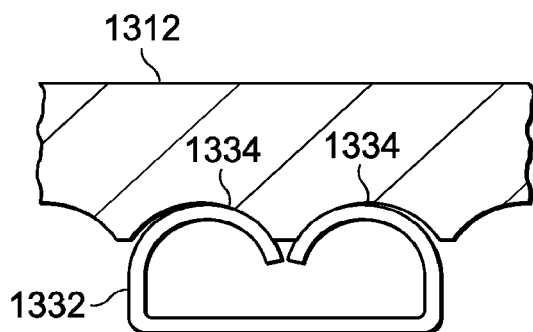
FIG. 42B is a side view of a staple formed by the anvil of FIG. 40.
Figure 42C:
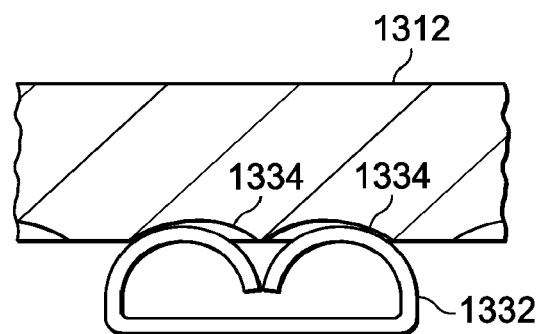
FIG. 42C is a side view of a staple formed by the anvil of FIG. 40.

FIG. 41 is an axial cross-sectional view of an anvil assembly 1201 having an anvil plate 1212 in accordance with one embodiment. The anvil plate 1212 can include a plurality of anvil pockets 1234 having any suitable shape. For example, the anvil plate 1212 can define a frustoconical cavity for each of the anvil pockets 1234, as illustrated, or the anvil pockets can have any shape such as curved, bowl-shaped, or the like. FIGS. 42A-42C illustrate embodiments of formed staples 1332 that can be formed by an anvil plate 1312 having pockets 1334 with different depths.

Figure 43A:
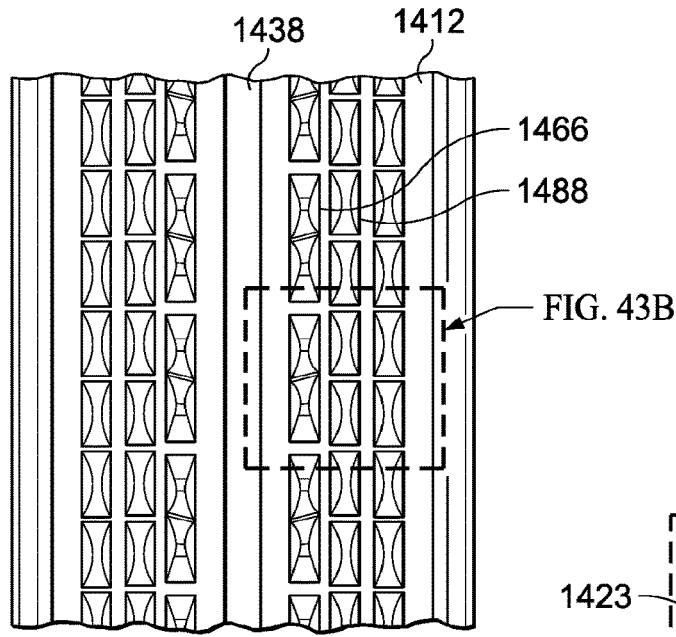
FIG. 43A is a partial bottom plan view of an anvil assembly having a plurality of anvil pockets in accordance with one embodiment.
Figure 43B:
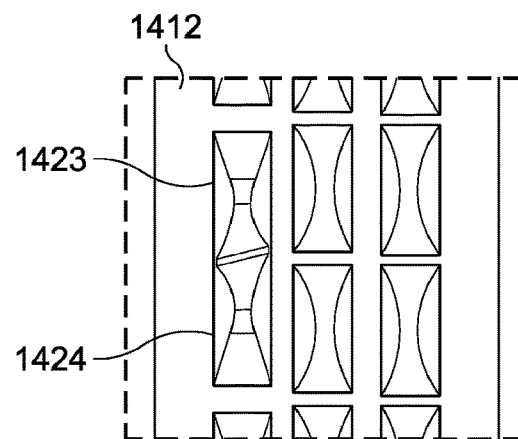
FIG. 43B is a more detailed view of a section of the anvil assembly shown in FIG. 43A.
Figure 43C:
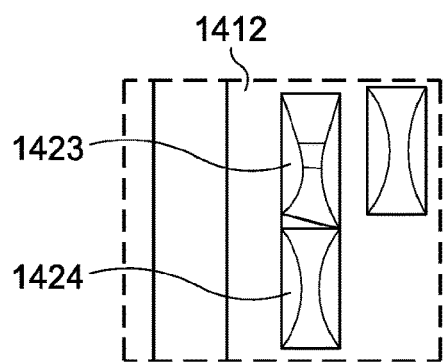
FIG. 43C is an partial bottom plan view of an anvil for an end effector in having a plurality of anvil pockets in accordance with an alternate embodiment.
Figure 44:
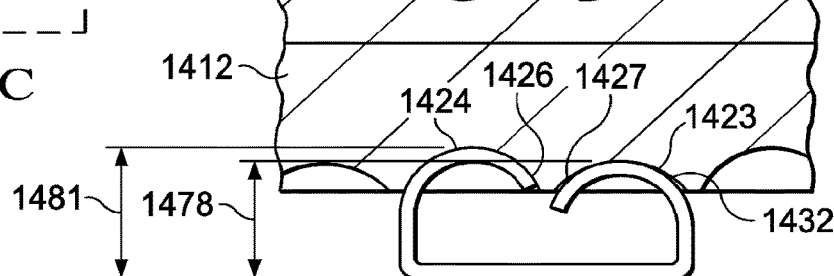
FIG. 44 is a side view of a staple formed by an anvil assembly in accordance with one embodiment.

With reference to FIGS. 43A-46, a stapling device can be configured to provide asymmetrical staples to achieve a desired tissue effect. Referring to FIGS. 43A and 43B, an anvil plate 1412 can include a first pocket 1466 having a first shape and a second pocket 1488 having a second shape. As illustrated in FIG. 43C, the first pocket can include a first cavity 1423 to receive the first tip 1426 of a staple 1332 (see, for example, FIG. 44) and a second cavity 1424 to accept a second tip 1427 of the staple, where the first cavity 1423 has a different geometry than the second cavity 1424. The first cavity 1423 can have a first depth 1478 and the second cavity 1424 can have a second depth 1481, where the first depth 1478 can be shallower than the second depth 1481. As illustrated in FIG. 44, the formed staple 1432 can be asymmetrical, which may be advantageous for providing uniform compression or maintaining the integrity of a staple line. Pockets having any suitable cavities with any suitable geometry, angels, or sizing are contemplated.

Figure 45:
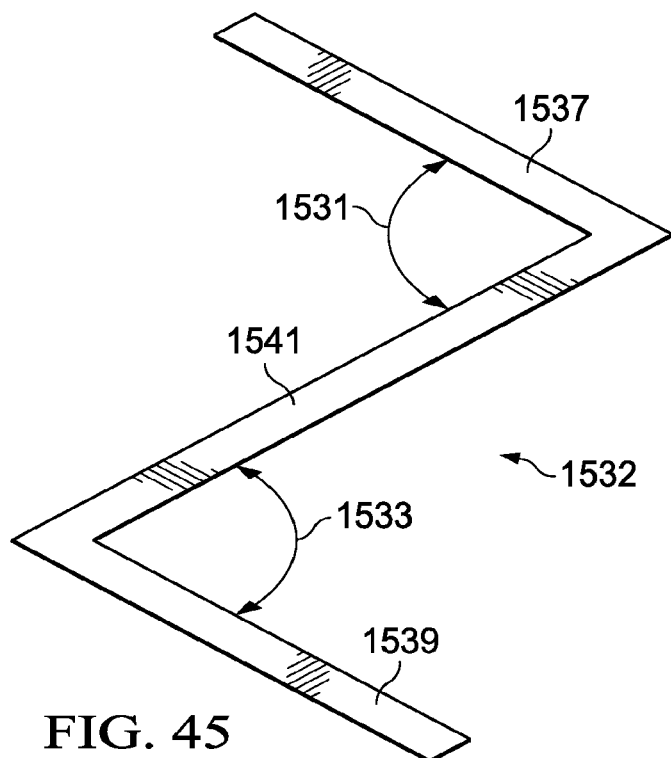
FIG. 45 is a top view of a staple formed by an anvil assembly in accordance with an alternate embodiment.
Figure 46:
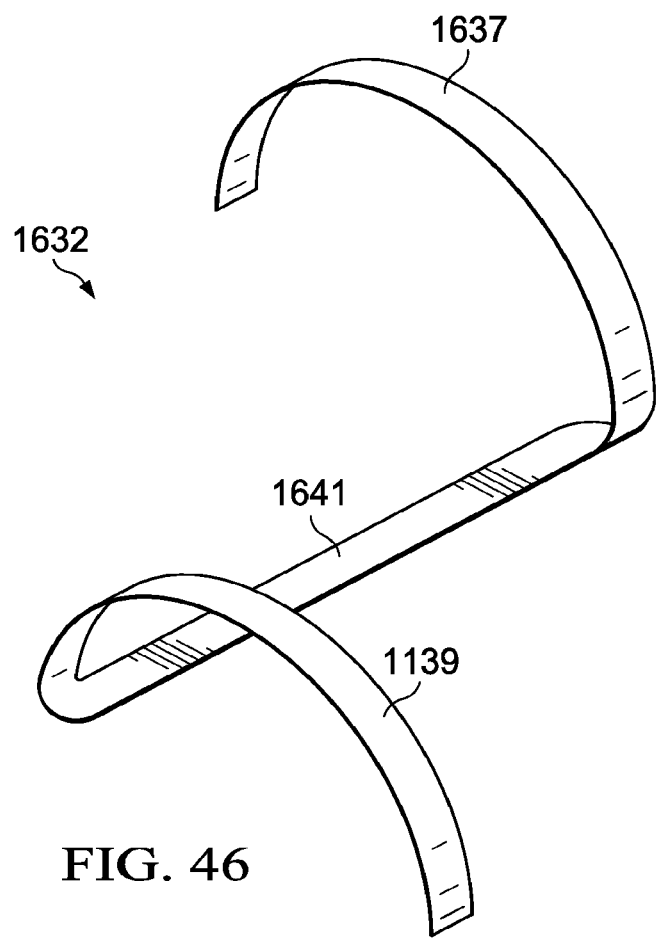
FIG. 46 is a perspective view of a staple formed by an anvil assembly in accordance with an alternate embodiment.

Referring to FIGS. 45 and 46, altering the geometry of the pockets can produce staples that are two-dimensional, along a single plane, or three-dimensional, where the formed staple legs lie in different planes. For example, along the length of the anvil, the pocket shapes may produce varying amounts of offset in the staple legs making three-dimensional staples of varying offset in the axial direction. In another example, the pocket shapes may produce varying amounts of offset in one row versus another row of a multi-row endocutter. A three-dimensional staple provided along the cut tissue edge may provide better hemostasis with a larger compressive zone.

FIG. 45 is a top view of a formed staple 1532 produced by an endocutter in accordance with one embodiment. The formed staple 1532 is illustrated as a three-dimensional formed staple with a first formed staple leg 1537 offset from a staple base 1541 at an angle 1531, while a second formed staple leg 1539 is offset in the other direction from the staple base 1541 at an angle 1533. These opposed angle offsets can create a three-dimensional staple having tissue compression characteristics that may be beneficial. FIG. 46 is a perspective view of the formed staple 1632 produced by an endocutter in accordance with one embodiment having a three-dimensional shape.

Figure 47:
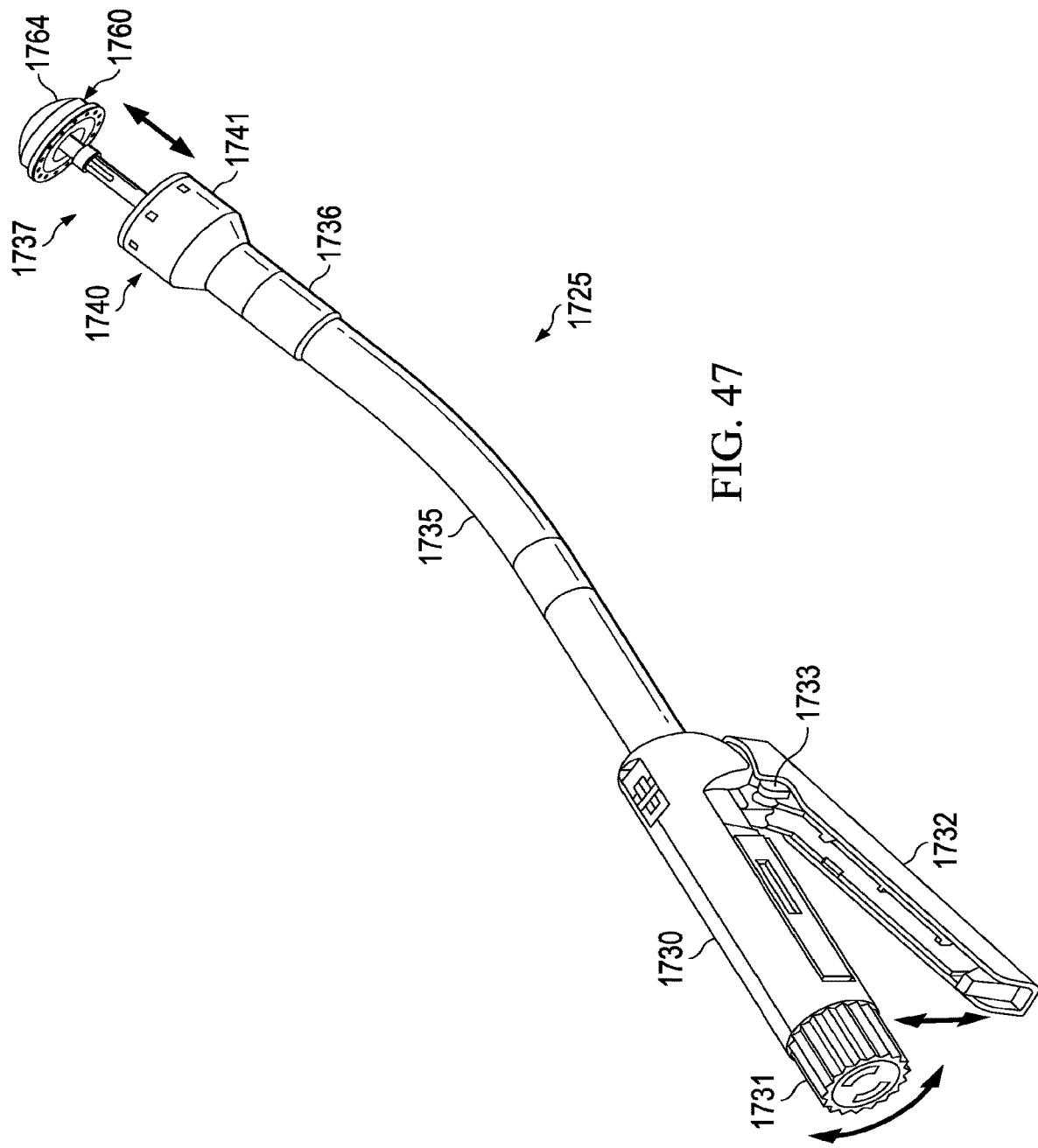
FIG. 47 is a perspective view of a stapler in accordance with one embodiment having a circular anvil.

FIG. 47 is a perspective view of a surgical stapling instrument 1725 in accordance with one embodiment having a circular anvil assembly 1760. The surgical stapling instrument 1725 is illustrated as another type of stapling instrument that may advantageously utilize the embodiments described herein. Other instruments that may advantageously utilize the embodiments described herein include linear staplers, linear cutters, endocutters or other surgical stapling and cutting instruments.

The anvil assembly 1760 can include a first circular anvil pocket row, and a second circular anvil pocket row. In a circular stapler, typically there are concentric circles of staple lines. It may be advantageous to provide the innermost circular row having a shallower or deeper staple pocket depth than the pocket depths on circular staple rows outside the inner-most circular row. It may also be useful to provide varying pocket depths within a row as a function of position in the row. It may further be useful to provide staples manufactured from different materials in an inner-row versus an outer row when there are two or more rows of staples in the circular configuration.

The surgical stapling instrument 1725 can include a handle 1730 for the surgeon to grasp, a shaft 1735 extending distally from the handle 1730, and a distal stapling end effector 1737 for the end-to-end anastomosis of cylindrical tissue. A firing trigger 1732 can be pivotably connected to the handle 1730. Firing trigger 1732 is shown in the open position extending from the handle 1730 and can be moveable to a closed position adjacent to the handle 1730. The shaft 1735 can be slightly curved for anatomical placement of the stapling end effector 1737 into hard to reach lower anatomical positions. The stapling end effector 1737 can have a fixed stapling head assembly 1740 and the anvil assembly 1760 can be moveably connected to an anvil closure knob 1731. Rotation of the anvil closure knob 1731 can move the anvil assembly 1760 from the spaced away position to a position adjacent to the stapling head assembly.

The anvil assembly 1760 can be detachably connected to the stapling head assembly 1740 and can be easily removed from the surgical stapling instrument 1725 in the full open position. A firing trigger 1732 can be moveable from an open position to a closed position to staple and cut two sections of colon or bowel together within the stapling end effector 1737. A safety latch 1733 is shown in the locked position to lock the firing trigger 1732 in the open position to prevent accidental firing.

Although examples have been illustrated referencing an endocutter in the figures above, it is contemplated that the concepts presented herein may also be useful on other staplers, including, but not limited to, linear cutters, linear staplers, circular staplers, endocutters or other instruments incorporating staples.

It is further contemplated to have different pocket shapes in the different rows laterally, longitudinally in different segments or both laterally and longitudinally. For example, a stronger staple that resists deformation may be provided in the lateral most position by varying the pocket shape as well as the pocket depth, to provide a bow tie or rectangular shaped staple leg after forming the staple in the pocket. Pocket depths and pocket shapes may both be varied as described herein either individually or in combination.

Pocket depth may range, for example, from about 0.010 inches to about 0.050 inches. In one embodiment, an inner row near the cut line may have a pocket depth of about 0.012 inches, a middle row may have a pocket depth of about 0.022 inches, and an outer row may have a pocket depth of about 0.032 inches. In another embodiment, where pocket depths vary along the length of a staple line, pocket depths may vary from, for example, 0.012 inches at the shallowest pocket depth to 0.052 inches at the deepest pocket depth. Useful pocket depths may range, for example, from about 0.010 inches to about 0.060 inches.

Any suitable staple may be used having any suitable materials. The material composition of the staple may be changed as a function of location as described herein. Using alloys with a higher concentration of vanadium and aluminum may make each staple more resistant to deformation and increase spring back, where this material can be used in the outermost rows, for example, to provide the most mechanical strength and the tallest staple to allow for improved blood flow to tissue. Using pure titanium on the innermost row, for example, may provide for the least amount of springback, which may be better for hemostasis.

In one embodiment, an alloy of titanium with vanadium 6% and aluminum 4% can be used for an outer row of staples, an alloy of titanium with vanadium 4% and aluminum 2.5% can be used in a middle row of staples, and pure titanium can be used for an inner row of staples to vary springback for each row and improve the staple line outcome. As described herein, varying one or more of staple anvil pocket depth, pocket shape, or staple composition as a function of location laterally or longitudinally may provide for improved outcomes when using surgical staplers.

In one embodiment, a rectangular deeper pocket shape that produces an overformed staple with a tight bend radius using a stronger material may be provided in the lateral position (furthest from cut edge.) An offset pocket shape, with a shallower pocket using a weaker staple material, may be used adjacent to the cut edge for improved hemostasis. In a six-row stapler, the middle row may use a combination of the lateral row and cut edge row to blend such characteristics.

In various embodiments disclosed herein, a single component can be replaced by multiple components and multiple components can be replaced by a single component to perform a given function or functions. Except where such substitution would not be operative, such substitution is within the intended scope of the embodiments. For example, staple leg heights, staple material of manufacture, anvil pocket depths, anvil pocket shapes and anvil pocket asymmetry may all be varied in any combination.

The foregoing description of embodiments and examples has been presented for purposes of illustration and description. It is not intended to be exhaustive or limiting to the forms described. Numerous modifications are possible in light of the above teachings. Some of those modifications have been discussed, and others will be understood by those skilled in the art. The embodiments were chosen and described in order to best illustrate principles of various embodiments as are suited to particular uses contemplated. The scope is, of course, not limited to the examples set forth herein, but can be employed in any number of applications and equivalent devices by those of ordinary skill in the art. Rather it is hereby intended the scope of the invention to be defined by the claims appended hereto.

What is claimed is:

1. An end effector for use by a surgeon to staple an anatomical structure of a patient during a minimally invasive procedure, the anatomical structure having a first outer side and a second outer side, the end effector comprising:
    (a) a first jaw having a distal end, a proximal end, a longitudinal axis, and an anvil, the anvil comprising an anvil face positionable on the first outer side of the anatomical structure, the anvil further comprising a plurality of pocket rows, each pocket row comprising a plurality of staple pockets, wherein the plurality of pocket rows includes at least one pocket row whose plurality of staple pockets comprises a depth that differs from the depth of the plurality of staple pockets of at least one other pocket row;

(b) a second jaw having a distal end, a proximal end, a longitudinal axis, and a cartridge operably configured to house a plurality of staples, the cartridge having a cartridge face positionable on the second outer side of the anatomical structure;
(c) a first coupling that couples the distal end of the first jaw to the distal end of the second jaw; and
(d) a second coupling including a monolithic rigid link, the monolithic rigid link being inflexible, the monolithic rigid link having a first end and a second end, and wherein, when the end effector is in both a first open position and a second closed position, the first end of the monolithic rigid link is movably and fixedly connected to the first jaw, and the second end of the monolithic rigid link is movably and fixedly connected to the second jaw,
wherein the monolithic rigid link includes a first portion offset and angled from a second portion, the monolithic rigid link further including a ramp surface;
wherein the end effector has a distal end and a proximal end, and a distance between the distal end and the proximal end is fixed; and
wherein a staple configuration in which a staple of the plurality of staples is formed is based on the depth of a corresponding staple pocket.

2. The end effector of claim 1, wherein the distal end of the first jaw and the proximal end of the first jaw are aligned with the longitudinal axis of the first jaw.

3. The end effector of claim 1, wherein the first coupling is a distal coupling and comprises a pin having a pin axis, the pin axis being transverse to the longitudinal axis of the first jaw and the longitudinal axis of the second jaw, wherein the pin pivotally couples the first end of the first jaw to the first end of the second jaw.

4. The end effector of claim 1, wherein the second coupling comprises a slot defined by the first jaw or the second jaw that retains the monolithic rigid link such that the monolithic rigid link is slidable within the slot.

5. The end effector of claim 4, wherein the slot has a length of from 3 millimeters to 8 millimeters.

6. The end effector of claim 1, further comprising the plurality of staples at least partially retained by the cartridge of the second jaw.

7. The end effector of claim 6, wherein the plurality of staples retained at least partially by the cartridge are aligned along the longitudinal axis of the second jaw between the first coupling and the second coupling.

8. The end effector of claim 1, further comprising a blade having a cutting surface and at least one lateral arm configured to translate along a longitudinal axis of the end effector.

9. The end effector of claim 8, further comprising a channel defined by the first jaw or the second jaw to retain the at least one lateral arm of the blade.

10. The end effector of claim 8, wherein the blade is transitioned from a first position at a distal end of the end effector to a second position at a proximal end of the end effector such that the anatomical structure is resected.

11. An end effector comprising:
(a) a first jaw having a distal end, a proximal end, an anvil having an anvil face, and a first channel, the anvil further comprising a plurality of pocket rows, each pocket row comprising a plurality of staple pockets, wherein the plurality of pocket rows includes at least one pocket row whose plurality of staple pockets comprises a depth that differs from the depth of the plurality of staple pockets of at least one other pocket row;
(b) a second jaw having a distal end, a proximal end, a cartridge having a cartridge face, and a second channel;
(c) a first coupling that couples the distal end of the first jaw to the distal end of the second jaw;
(d) a second coupling including a monolithic rigid link, the monolithic rigid link being inflexible, and the monolithic rigid link having a first end and a second end, and wherein, when the end effector is in both a first open position and a second closed position, the first end of the monolithic rigid link is movably and fixedly connected to the first jaw, and the second end of the monolithic rigid link is movably and fixedly connected to the second jaw, wherein the monolithic rigid link includes a first portion offset and angled from a second portion, the monolithic rigid link further including a ramp surface; and
(e) an I-shaped blade, the I-shaped blade comprising;
  (i) a blade portion having a cutting edge;
  (ii) at least one upper lateral arm, wherein the at least one upper lateral arm is slidably positioned in the first channel; and
  (iii) at least one lower lateral arm, wherein the at least one lower lateral arm is slidably positioned in the second channel,
wherein the end effector has a distal end and a proximal end, and a distance between the distal end and the proximal end is fixed; and
wherein a staple configuration in which a staple of a plurality of staples retained by the cartridge is formed is based on the depth of a corresponding staple pocket.

12. The end effector of claim 11, wherein the cartridge comprises a plurality of staples.

13. The end effector of claim 12, wherein the at least one lower lateral arm is operably configured to urge each of the plurality of staples from the cartridge when the I-shaped blade is actuated from a first position at a distal end of the end effector to a second position at a proximal end of the end effector.

14. A surgical instrument to staple and resect an anatomical structure of a patient, the surgical instrument comprising:
(a) an end effector, the end effector comprising;
  (i) a first jaw having a first end, a second end, a longitudinal axis, and an anvil, the anvil comprising an anvil face positionable on a first outer side of the anatomical structure, the anvil further comprising a plurality of pocket rows, each pocket row comprising a plurality of staple pockets, wherein the plurality of pocket rows includes at least one pocket row whose plurality of staple pockets comprises a depth that differs from the depth of the plurality of staple pockets of at least one other pocket row;
  (ii) a second jaw having a first end, a second end, a longitudinal axis, and a cartridge operably configured to house a plurality of staples, the cartridge having a cartridge face positionable on a second outer side of the anatomical structure;
  (iii) a first coupling that couples the first end of the first jaw to the first end of the second jaw; and
  (iv) a second coupling including a one-piece rigid link, the one-piece rigid link being inflexible, and the one-piece rigid link having a first end and a second end, and wherein, when the end effector is in both a first open position and a second closed position, the first end of the one-piece rigid link is movably and fixedly connected to the first jaw, wherein the one-piece rigid link includes a first portion offset and angled from a second portion, the one-piece rigid link further including a ramp surface, (b) an elongate tube, the elongate tube having a proximal end and a distal end, wherein the distal end is coupled with the end effector and wherein the second end of the rigid link is movably and fixedly connected to the elongate tube;

(c) a handle, the handle having a proximal end and a distal end, wherein the distal end of the handle is coupled with the proximal end of the elongate tube; and (d) a drive assembly comprising a motor to actuate the end effector, wherein the end effector has a distal end and a proximal end, and a distance between the distal end and the proximal end is fixed; and wherein a staple configuration in which a staple of the plurality of staples is formed is based on the depth of a corresponding staple pocket.

15. The surgical instrument of claim 14, wherein the distal end of the first jaw and the proximal end of the first jaw are aligned with the longitudinal axis of the first jaw.

16. The surgical instrument of claim 14, wherein the first coupling is a distal coupling and comprises a pin having a pin axis, the pin axis being transverse to the longitudinal axis of the first jaw and the longitudinal axis of the second jaw, wherein the pin pivotally couples the first end of the first jaw to the first end of the second jaw.

17. The surgical instrument of claim 14, wherein the second coupling comprises a slot defined by the first jaw or the second jaw that retains the one-piece rigid link such that the one-piece rigid link is slidable within the slot.

18. The surgical instrument of claim 17, wherein the slot has a length of from 3 millimeters to 8 millimeters.

19. The surgical instrument of claim 14, further comprising the plurality of staples at least partially retained by the cartridge of the second jaw.

20. The surgical instrument of claim 19, wherein the plurality of staples retained at least partially by the cartridge are positioned between the first coupling and the second coupling.

21. The surgical instrument of claim 14, further comprising a blade having a cutting surface and at least one lateral arm.

22. The surgical instrument of claim 21, further comprising a channel defined by the first jaw or the second jaw to retain the at least one lateral arm of the blade.

23. The surgical instrument of claim 21, wherein the blade is transitioned from a first position at a distal end of the end effector to a second position at a proximal end of the end effector such that the anatomical structure is resected.

24. A surgical instrument to staple and resect an anatomical structure of a patient, the surgical instrument comprising:
(a) an end effector, the end effector comprising;
  (i) a first jaw having a first end, a second end, an anvil having an anvil face, and a first channel; the anvil further comprising a plurality of pocket rows, each pocket row comprising a plurality of staple pockets, wherein the plurality of pocket rows includes at least one pocket row whose plurality of staple pockets comprises a depth that differs from the depth of the plurality of staple pockets of at least one other pocket row;
  (ii) a second jaw having a first end, a second end, a cartridge having a cartridge face, and a second channel;
  (iii) a first coupling that couples the first end of the first jaw to the first end of the second jaw;
  (iv) a second coupling including a one-piece rigid link, the one-piece rigid link being inflexible and having a first end and a second end, wherein, when the end effector is in both a first open position and a second closed position, the first end of the one-piece rigid link is movably and fixedly connected to the first jaw, wherein the one-piece rigid link includes a first portion offset and angled from a second portion, the one-piece rigid link further including a ramp surface; and
  (v) an I-shaped blade, the I-shaped blade comprising a blade portion having a cutting edge, at least one upper lateral arm, wherein the at least one upper lateral arm is slidably positioned in the first channel, and at least one lower lateral arm, wherein the at least one lower lateral arm is slidably positioned in the second channel; and (b) an elongate tube, the elongate tube having a proximal end and a distal end, wherein the distal end is coupled with the end effector and wherein the second end of the rigid link is movably and fixedly connected to the elongate tube;

(c) a handle, the handle having a proximal end and a distal end, wherein the distal end of the handle is coupled with the proximal end of the elongate tube; and (d) a drive assembly comprising a motor to actuate the end effector, wherein the end effector has a distal end and a proximal end, and a distance between the distal end and the proximal end is fixed; and wherein a staple configuration in which a staple of the plurality of staples is formed is based on the depth of a corresponding staple pocket.

25. The surgical instrument of claim 24, wherein the cartridge comprises a plurality of staples.

26. The surgical instrument of claim 25, wherein the at least one lower lateral arm is operably configured to urge each of the plurality of staples from the cartridge when the I-shaped blade is actuated from a first position at a distal end of the end effector to a second position at a proximal end of the end effector.

27. An end effector for use by a surgeon to staple an anatomical structure of a patient during a minimally invasive procedure, the anatomical structure having a first outer side and a second outer side, the end effector comprising:
(a) a first jaw having a first end, a second end, a longitudinal axis, and an anvil, the anvil comprising an anvil face positionable on the first outer side of the anatomical structure, the anvil further comprising a plurality of pocket rows, each pocket row comprising a plurality of staple pockets, wherein the plurality of pocket rows includes at least one pocket row whose plurality of staple pockets comprises a depth that differs from the depth of the plurality of staple pockets of at least one other pocket row;
(b) a second jaw having a first end, a second end, a longitudinal axis, and a cartridge housing a plurality of staples, the cartridge having a cartridge face positionable on the second outer side of the anatomical structure;
(c) a first coupling that couples the first end of the first jaw to the first end of the second jaw;
(d) a second coupling including a rigid link and a slot, the rigid link being inflexible and having a first end and a second end, wherein, when the end effector is in both a first open position and a second closed position, the first end of the rigid link is movably and fixedly connected to the first jaw and the second end of the rigid link is movably and fixedly connected to the second jaw, and wherein said slot is defined in an end of the first jaw such that the slot retains the rigid link such that the rigid link is slidable within the slot, wherein the rigid link includes a first portion offset and angled from a second portion, the rigid link further including a ramp surface; and (e) a buttress, the buttress comprising;
  (i) a first buttress member, the first buttress member being positioned adjacent the anvil face such that the first buttress member covers a portion of the anvil face; and
  (ii) a second buttress member, the second buttress member being positioned adjacent the cartridge face such that the second buttress member covers a portion of the cartridge face, wherein the end effector has a distal end and a proximal end, and a distance between the distal end and the proximal end is fixed;

wherein a staple configuration in which a staple of a plurality of staples is formed is based on the depth of a corresponding staple pocket.

28. The end effector of claim 27, wherein the distal end of the first jaw and the proximal end of the first jaw are aligned with the longitudinal axis of the first jaw.

29. The end effector of claim 27, wherein the first buttress member comprises an adhesive for attachment to the anvil face and the second buttress member comprises an adhesive for attachment to the cartridge face.

30. The end effector of claim 27, wherein the first buttress member comprises an adhesive portion for attachment to a side of the first jaw and the second buttress member comprises an adhesive portion for attachment to a side of the second jaw.

31. The end effector of claim 27, wherein the first buttress member and the second buttress member are formed from a bioabsorbable material.

32. The end effector of claim 27, wherein the first jaw comprises a plurality of supports that are spaced apart along a length of the first jaw.

33. The end effector of claim 32, wherein the first buttress member or the second buttress member defines a plurality of apertures sized to receive a cord.

34. The end effector of claim 33, wherein the cord is threaded through the plurality of apertures in the first buttress member or the second buttress member to retain the first buttress member adjacent the anvil face and the second buttress member adjacent the cartridge face.

35. The end effector of claim 34, wherein the first buttress member and the second buttress member have a planar configuration.

36. The end effector of claim 27, further comprising a blade that is transitioned from a first position at a distal end of the end effector to a second position at a proximal end of the end effector such that the first buttress member and the second buttress member are cut.

37. An end effector for use by a surgeon to staple an anatomical structure of a patient during a minimally invasive procedure, the end effector comprising:

(a) an anvil comprising a first end, a second end, and an anvil face; the anvil further comprising a plurality of pocket rows, each pocket row comprising a plurality of staple pockets, wherein the plurality of pocket rows includes at least one pocket row whose plurality of staple pockets comprises a depth that differs from the depth of the plurality of staple pockets of at least one other pocket row;

(b) a cartridge comprising a first end, a second end, and a cartridge face, the cartridge housing a plurality of staples, wherein the first end of the anvil is coupled with the first end of the cartridge and the second end of the anvil is coupled to the second end of the cartridge;

(c) a one-piece rigid link, the one-piece rigid link being inflexible, and wherein the one-piece rigid link having a first end and a second end, and wherein, when the end effector is in both a first open position and a second closed position, the first end of the one-piece rigid link is movably and fixedly connected to the cartridge, and the second end of the rigid link is movably and fixedly connected to the anvil, wherein the one-piece rigid link includes a first portion offset and angled from a second portion, the one-piece rigid link further including a ramp surface; and (d) a buttress, the buttress comprising;
  (i) a first buttress member, the first buttress member being coupled with the anvil face such that the first buttress member covers a portion of the anvil face; and
  (ii) a second buttress member, the second buttress member being coupled with the cartridge face such that the second buttress member covers a portion of the anvil face, wherein the end effector has a distal end and a proximal end, and a distance between the distal end and the proximal end is fixed;

wherein a staple configuration in which a staple of the plurality of staples is formed is based on the depth of a corresponding staple pocket.

38. The end effector of claim 37, further comprising a blade having a cutting surface configured to cut the first buttress member and the second buttress member.

39. The end effector of claim 38, wherein the blade is transitioned from a first position at a distal end of the end effector to a second position at a proximal end of the end effector to cut the first buttress member and the second buttress member.

40. The end effector of claim 37, wherein the distal end of the anvil and the proximal end of the anvil are aligned with the longitudinal axis of the anvil.

41. The end effector of claim 37, wherein the first buttress member comprises an adhesive for attachment to the anvil face and the second buttress member comprises an adhesive for attachment to the cartridge face.

42. The end effector of claim 37, wherein each of the plurality of staples is operably configured to puncture the first buttress member and the second buttress member.

43. The end effector of claim 37, wherein the first buttress member and the second buttress member are formed from a bioabsorbable material.

44. The end effector of claim 37, wherein the anvil comprises a plurality of supports that are spaced apart along a length of the anvil.

45. The end effector of claim 44, wherein the first buttress member or the second buttress member define a plurality of apertures sized to receive a cord.

46. The end effector of claim 45, wherein the cord is threaded through the plurality of apertures in the first buttress member or the second buttress member to retain the first buttress member adjacent the anvil face or the second buttress member adjacent the cartridge face.

47. An end effector for use by a surgeon to staple an anatomical structure of a patient during a minimally invasive procedure, the end effector comprising:
  (a) an anvil that includes a first end, a second end, and an anvil face positionable on a first outer side of the anatomical structure; the anvil further comprising a plurality of pocket rows, each pocket row comprising a plurality of staple pockets, wherein the plurality of pocket rows includes at least one pocket row whose plurality of staple pockets comprises a depth that differs from the depth of the plurality of staple pockets of at least one other pocket row;
  (b) a cartridge housing a plurality of staples, the cartridge comprising a first end, a second end, and a cartridge face positionable on a second outer side of the anatomical structure, wherein the first end of the cartridge is coupled with the first end of the anvil and the second end of the cartridge is coupled with the second end of the anvil;
  (c) a monolithic rigid link, the monolithic rigid link being inflexible and having a first end and a second end, and wherein, when the end effector is in both a first open position and a second closed position, the first end of the monolithic rigid link is movably and fixedly connected to the cartridge, and the second end of the rigid link is movably and fixedly connected to the anvil, wherein the monolithic rigid link includes a first portion offset and angled from a second portion, the monolithic rigid link further including a ramp surface;
  (d) a blade, the blade comprising a cutting surface, wherein the blade is engageable with the anvil and the cartridge; and
  (e) a buttress, the buttress being a planar section of material coupled with the anvil face or the cartridge face,
  wherein the end effector has a distal end and a proximal end, and a distance between the distal end and the proximal end is fixed; and
  wherein a staple configuration in which a staple of the plurality of staples is formed is based on the depth of a corresponding staple pocket.

48. The end effector of claim 47, wherein the blade is transitioned from a first position at a distal end of the end effector to a second position at a proximal end of the end effector to cut the buttress.

49. The end effector of claim 47, wherein the distal end of the anvil and the proximal end of the anvil are aligned with the longitudinal axis of the anvil.

50. The end effector of claim 47, wherein the buttress comprises an adhesive for attachment to the anvil face or the cartridge face.

51. The end effector of claim 47, wherein each of the plurality of staples is operably configured to puncture the buttress.

52. The end effector of claim 47, wherein the buttress is formed from a bioabsorbable material.

53. The end effector of claim 47, wherein the anvil comprises a plurality of supports that are spaced apart along a length of the anvil.

54. The end effector of claim 53, wherein the buttress defines a plurality of apertures sized to receive a cord.

55. The end effector of claim 54, wherein the cord is threaded through the plurality of apertures in the buttress to retain the buttress adjacent the anvil face or the cartridge face.

56. An end effector comprising:
  (a) a first jaw having a first end, a second end, an anvil having an anvil face, and a first channel, the anvil further comprising a plurality of pocket rows, each pocket row comprising a plurality of staple pockets, wherein the plurality of pocket rows includes at least one pocket row whose plurality of staple pockets comprises a depth that differs from the depth of the plurality of staple pockets of at least one other pocket row;
  (b) a second jaw having a first end, a second end, a cartridge having a cartridge face, and a second channel;
  (c) a first coupling that couples the first end of the first jaw to the first end of the second jaw;
  (d) a second coupling including a monolithic rigid link and a slot, the monolithic rigid link being inflexible and having a first end and a second end, wherein, when the end effector is in both a first open position and a second closed position, the first end of the monolithic rigid link is movably and fixedly connected to the first jaw and the second end of the monolithic rigid link is movably and fixedly connected to the second jaw, and wherein the slot is defined in an end of the first jaw such that the slot retains the rigid link such that the rigid link is slidable within the slot, wherein the monolithic rigid link includes a first portion offset and angled from a second portion, the monolithic rigid link further including a ramp surface;
  (e) an I-shaped blade, the I-shaped blade comprising;
    (i) a blade portion having a cutting edge;
    (ii) at least one upper lateral arm, wherein the at least one upper lateral arm is slidably positioned in the first channel; and
    (iii) at least one lower lateral arm, wherein the at least one lower lateral arm is slidably positioned in the second channel; and
  (f) a buttress, the buttress being a planar section of material coupled with the anvil face or the cartridge face,
  wherein the end effector has a distal end and a proximal end, and a distance between the distal end and the proximal end is fixed; and
  wherein a staple configuration in which a staple of the plurality of staples is formed is based on the depth of a corresponding staple pocket.

* * * * *